United States Patent [19]
Saul et al.

[11] Patent Number: 5,851,488
[45] Date of Patent: Dec. 22, 1998

[54] APPARATUS FOR AUTOMATIC ELECTRO-OPTICAL CHEMICAL ASSAY DETERMINATION

[75] Inventors: Tom Saul, El Granada; Henry L. Schwartz, Menlo Park; Todd Guion, Felton; Hans O. Ribi, Hillsborough, all of Calif.

[73] Assignee: Biocircuits Corporation, Sunnyvale, Calif.

[21] Appl. No.: 608,693

[22] Filed: Feb. 29, 1996

[51] Int. Cl.⁶ .................................................. G01N 21/64
[52] U.S. Cl. .......................................... 422/67; 422/82.08
[58] Field of Search ................................. 422/67, 82.08, 422/100; 436/172

[56] References Cited

U.S. PATENT DOCUMENTS

| | | |
|---|---|---|
| 3,882,028 | 5/1975 | Zolner ........................................ 250/361 |
| 4,448,547 | 5/1984 | Wickersheim ........................... 374/131 |
| 4,560,286 | 12/1985 | Wickersheim ........................... 374/131 |
| 4,792,666 | 12/1988 | Cherry et al. ............................ 235/466 |
| 4,847,523 | 7/1989 | Schneider ................................. 307/490 |
| 4,849,172 | 7/1989 | Yafuso et al. ............................... 422/55 |
| 4,861,727 | 8/1989 | Hauenstein et al. ..................... 436/136 |
| 5,001,417 | 3/1991 | Pumphrey et al. ..................... 324/71.5 |
| 5,130,258 | 7/1992 | Makino et al. .......................... 436/169 |
| 5,134,359 | 7/1992 | Durley, III et al. .................... 324/71.1 |
| 5,266,271 | 11/1993 | Bankert et al. ....................... 422/82.07 |
| 5,294,799 | 3/1994 | Aslund et al. ........................ 250/458.1 |
| 5,374,395 | 12/1994 | Robinson et al. ......................... 422/64 |
| 5,399,486 | 3/1995 | Cathey et al. ............................ 435/7.9 |
| 5,418,371 | 5/1995 | Aslund et al. ........................ 250/458.1 |

Primary Examiner—Jeffrey Snay
Attorney, Agent, or Firm—Cooley Godward LLP

[57] ABSTRACT

An electro-optical instrument for measuring a quantitative physical parameter of a sample in a diagnostic cartridge is provided.

22 Claims, 48 Drawing Sheets

BARCODE FORMAT

| CARTR. TYPE | LOT NUMBER | EXPIRATION DATE | 0 0 0 | CHECKSUM |
|---|---|---|---|---|
| T4 COEFFICIENT 1 = $a_1$ | | T4 COEFFICIENT 2 = $b_1$ | REF ZONE HIGH | |
| T4 COEFFICIENT 3 = $c_1$ | | T4 COEFFICIENT 4 = $d_1$ | REF ZONE LOW | |
| TU COEFFICIENT 1 = $a_2$ | | TU COEFFICIENT 2 = $b_2$ | FTI COEFFICIENT | |
| | | | 0 0 0 | CHECKSUM |

PARAMETRY PHYSIC

T4 & TU COEFFICIENTS USES THE MANTISSA SCHEME:

| MANTISSA | S | EXP |
|---|---|---|

WHERE THE S (SIGN) BIT REPRESENTS:
0 => MANTISSA POSITIVE EXPONENT POSITIVE
1 => MANTISSA NEGATIVE EXPONENT POSITIVE
2 => MANTISSA POSITIVE EXPONENT NEGATIVE
3 => MANTISSA NEGATIVE EXPONENT NEGATIVE

REF ZONE HIGH, LOW, AND FTI COEFFICIENTS: USES THE MANTISSA SCHEME:

| MANTISSA | S | EXP |
|---|---|---|

T4 CORRELATION COEFFICIENTS: $\quad T4 \quad y = \dfrac{a_1 - d_1}{1 + \left(\dfrac{x}{c_1}\right)^{b_1}} + d$ TU CORRELATION COEFFICIENTS: $\quad y = a_2 + b_2 x$

*FIG. 6*

| MODEL NO. | LENGTH (mm) | DIAMETER (mm) | INPUT VOLTAGE (Vs) | LAMP CURRENT (IL) | LAMP VOLTAGE (VAC) | INTEN-SITY (LUMEN) | MAX. CURRENT |
|---|---|---|---|---|---|---|---|
| BF959UV1/2 | 60 | 9.0 | 250 | 5±1mA | 135 | $\frac{300\mu W}{cm^2}$ | 10mA |

| SHORTED ELECTRODES /2 | |
|---|---|
| LEADS | OHMS |
| 1 & 2<br>3 & 4 | 0<br>0 |
| 1 & 2 TO<br>3 & 4 | INFINITE |

ALL MECHANICAL DIMENSION TOLERANCES ARE (10.mm) .008 UNLESS OTHERWISE SPECIFIED

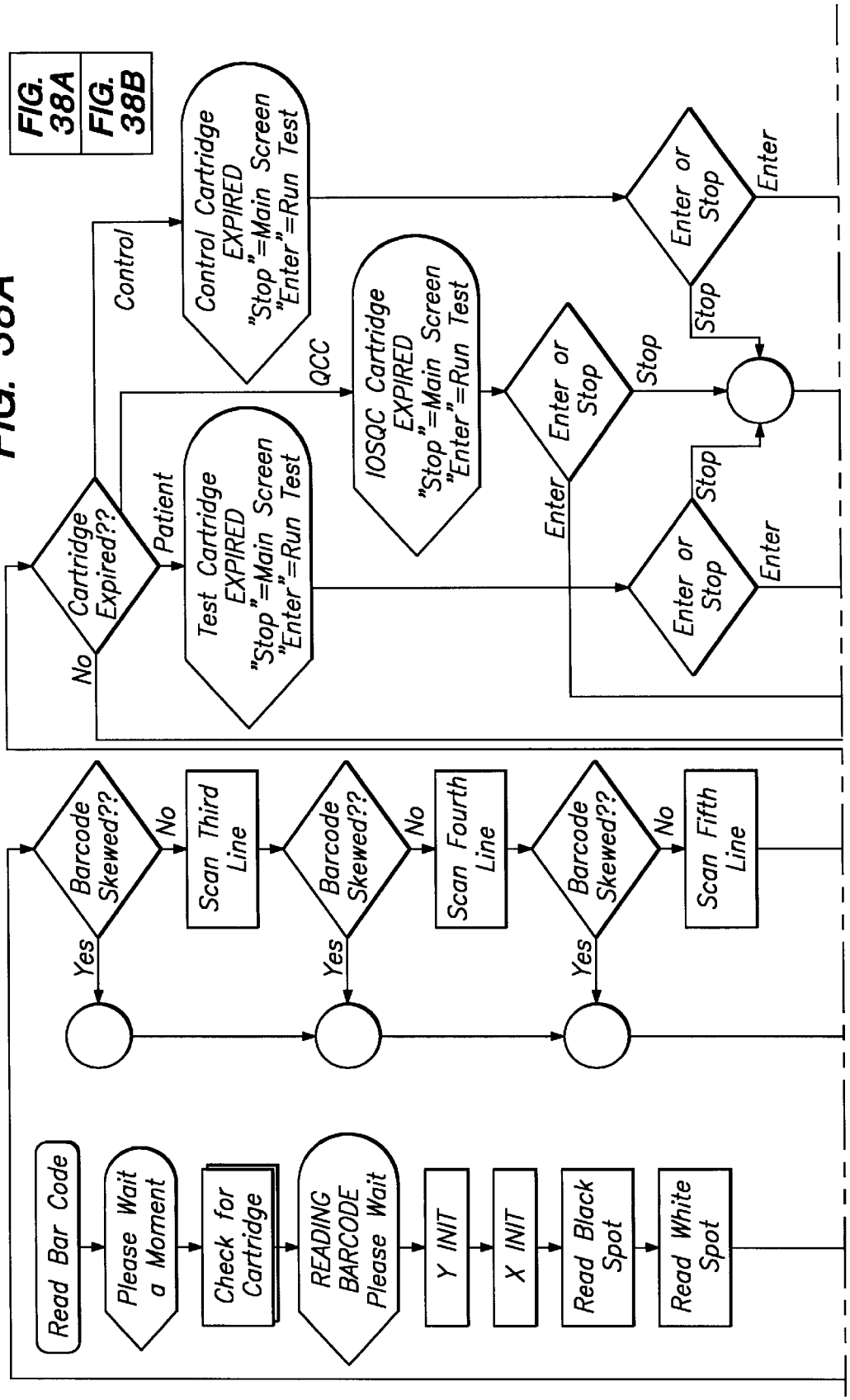

APPARATUS FOR AUTOMATIC ELECTRO-OPTICAL CHEMICAL ASSAY DETERMINATION

FIELD OF THE INVENTION

The invention relates to the field of optical analytical instruments in general, and more particularly, to an improved electro-optical instrument and method for generating digital data from measured fluorescence levels emitted by an irradiated sample specimen to determine the chemical concentration of an analyte based on the measured florescence levels.

BACKGROUND OF THE INVENTION

As our understanding of different physiological phenomenon has increased, there has arisen a need to improve methods of measuring the wide variety of substances involved in such processes. From the clinical laboratory, interest has developed in being able to measure various substances in the doctor's office, the home, at bedside, in the field, as well as at other sites. With the continuously increasing number of physiologically active substances, both naturally occurring and synthetic, there has been a desire to be able to measure the substances as indicative of the health status of an individual, for therapeutic dosage monitoring, for research, and the like. The substances may be found in a wide variety of samples, ranging over numerous orders of magnitude in concentration for their dynamic ranges of activity, and further differ as to the ease with which one may detect their presence.

The methods for detection have ranged from radioactive labels, light absorption, fluorescence, chemiluminescence, agglutination, etc. In the field of analytical chemistry, fluorescence polarization instruments have increasingly been employed in clinical applications. Of particular use in medical laboratories, such instruments enable rapid analysis of body fluid samples, such as those of a patient's blood, which have been treated with a fluorescent material in order to determine the presence and molar concentration of selected substances in the samples.

Assays using such instruments contain fluorescent dyes called fluorophores which fluoresce or emit light when excited with excitation light in the excitation band of the particular fluorophore being used. These fluorophores are used to "tag" the target molecules or proteins of interest, i.e., the fluorophores are attached to the molecules or proteins of interest in known tagging processes. The quantity of the molecules or proteins of interest can then be deduced by counting the number of fluorescent emissions occurring over a given period of time.

Generally, fluorescent polarization instruments, i.e., fluorometers, operate so as to direct one or more beams of linearly polarized excitation light upon the treated sample. The excitation light is typically of a high intensity and monochromatic corresponding to the peak of the absorption spectrum of the sample. The fluorescent molecules, when excited by the polarized light, emit luminous energy which, in its polarization value, depends upon the molecular size of the species which fluoresces. The degree of polarization also depends upon other parameters, such as, for example, the state of the molecules, i.e., whether or not the molecules are bound or unbound to one another.

The illuminated fluorescent sample therefore becomes a secondary source of radiation, emitting light in a spectrum peaked at a somewhat longer wavelength than the excitation light. A vertical polarizer in the emission light path passes vertically polarized light to a photo sensor for detecting the resulting emission light from the sample and measuring the intensity of the fluorescent emission. A second polarizer in a separate emission light path passes horizontally polarized light from the radiating fluorescent sample to a second photo sensor to simultaneously measure the horizontal component of a fluorescent emission and thereby permit determination of the degree of polarization of the emitted light.

One difficulty encountered in analyzing such fluorometric assays arises when samples are used which contain extremely small amount of the target substance. Under these circumstances it has been difficult to differentiate the effect of changes in the system upon the calculated answer from those arising due to changes in the amount of sample concentration. This system variation, if not neutralized or eliminated, can destroy the accuracy of the calculated concentration of the target substance.

One source of such variation is introduced by the analog detection and conversion circuitry commonly used in fluorometers and other electro-optical measurement instrumentation. In particular, the dynamic range and linearity of this conventional circuitry have been limited due to inadequacies of the analog system in signal amplification and conversion. Furthermore, such analog conversion systems have been less than satisfactory in operating over a wide range of emission light intensities, particularly at lower intensity levels. It is believed that this less than optimal performance may result in part from the use of analog amplification circuits susceptible to common-mode noise, leakage and offset errors. There is, therefore, a need for a electro-optical measurement instrument in which incorporates detection and conversion circuitry capable of producing light intensity measurements of increased dynamic range and linearity at a high level of accuracy.

In addition, in order to ensure that non-technical individuals are able to utilize electro-optical measurement instruments to perform accurate assays, it is essential that simple protocols presented to the user, even if the actual measurement/assay protocols or procedures performed by the instrument is relatively complex, and that the measurement readings be stable, and relatively automatic. It would thus be desirable to have a diagnostic instrument designed to accept a separate diagnostic disposable cartridge unit, or the like, for each test or assay determination. Such a disposable unit is described in, for example, issued U.S. Pat. No. 5,399,486, entitled Disposable Unit in Diagnostic Assays, filed Feb. 18, 1993, allowed U.S. patent application Ser. No. 08/179,749, now U.S. Pat. No. 5,503,985, filed Jan. 7, 1994 and copending U.S. patent applications Ser. No. 08/296,489, now U.S. Pat. No. 5,660,993, filed Aug. 24, 1994, Ser. No. 08/414,331, now U.S. Pat. No. 5,698,406, filed Mar. 30, 1995 and Ser. No. 08/420,987, filed Apr. 6, 1995, all of which are herein incorporated by reference. The diagnostic disposable cartridge unit can provide the various necessary reagents, can serve to ensure their mixing, and can allow for the proper fitting into the electro-optical measurement instrument. In this manner, one can be relatively assured that assay determinations may be made rapidly and with a minimum opportunity for error. Where one can use a disposable unit which only requires the addition of the sample to the disposable unit, great labor savings may be realized, since individuals of high technical qualification would not be required and accuracy would be relatively assured.

Additionally, it would be advantageous for an electro-optical measurement instrument to provide for easy and accurate quality control. In order to minimize user involvement, the instrument preferably should perform automatic quality checks of both the instrument and the diagnostic cartridge every time a test is run. It would also be advantageous for the instrument to utilize various calibration cartridges to ensure proper functioning of the instrument's mechanical, electrical, procedural, and software components, and to incorporate self-calibration apparatus and procedures.

There is, therefore, a continuing need for an electro-optical measurement instrument utilizing disposable assay units or cartridges, where the units allow for performing the assay protocol, with minimal measurement and input from the operator, while allowing for sensitive, accurate, and repeatable quantification of sample concentration.

SUMMARY OF THE INVENTION

In summary, the present invention is an electro-optical instrument for measuring a quantitative physical parameter, such as concentration, of a sample tagged with a fluorophore. The instrument includes a light source, disposed to be driven by an excitation signal, for projecting a beam of excitation light upon the sample and a reference beam of light upon a reference detector. The instrument optical system is configured to transmit portions of the excitation light in order to cause generation of an emitted fluorescence from the sample target. The instrument further includes a synchronous detection circuitry for generating a detection signal in response to the transmitted emitted fluorescence and a reference signal in response to the reference beam. An differential converter is operative to produce an output signal representative of the quantitative physical parameter of interest, such as the analyte concentration, based upon the reference and detection signals.

The instrument will preferably include reference and signal detectors for producing analog reference and emission signals respectively indicative of the intensities of the reference beam and transmitted emitted fluorescence. In one embodiment of the invention, a plurality of such measurements pairs (reference and emission) are obtained at predetermined time intervals to determine the reaction rate kinetics, and the concentration of the analyte is determined by correlating the reaction kinetics with known values.

BRIEF DESCRIPTION OF THE DRAWINGS

Additional objects and features of the invention will be more readily apparent from the following detailed description and appended claims when taken in conjunction with the drawings, in which:

FIG. 6 is an illustration showing a map of the organization of bar code information show in FIG. 5 for T4 and TU type assay cartridges.

DESCRIPTION OF THE PREFERRED EMBODIMENT

I. SYSTEM OVERVIEW AND OPERATIONAL SUMMARY

Figure 1:
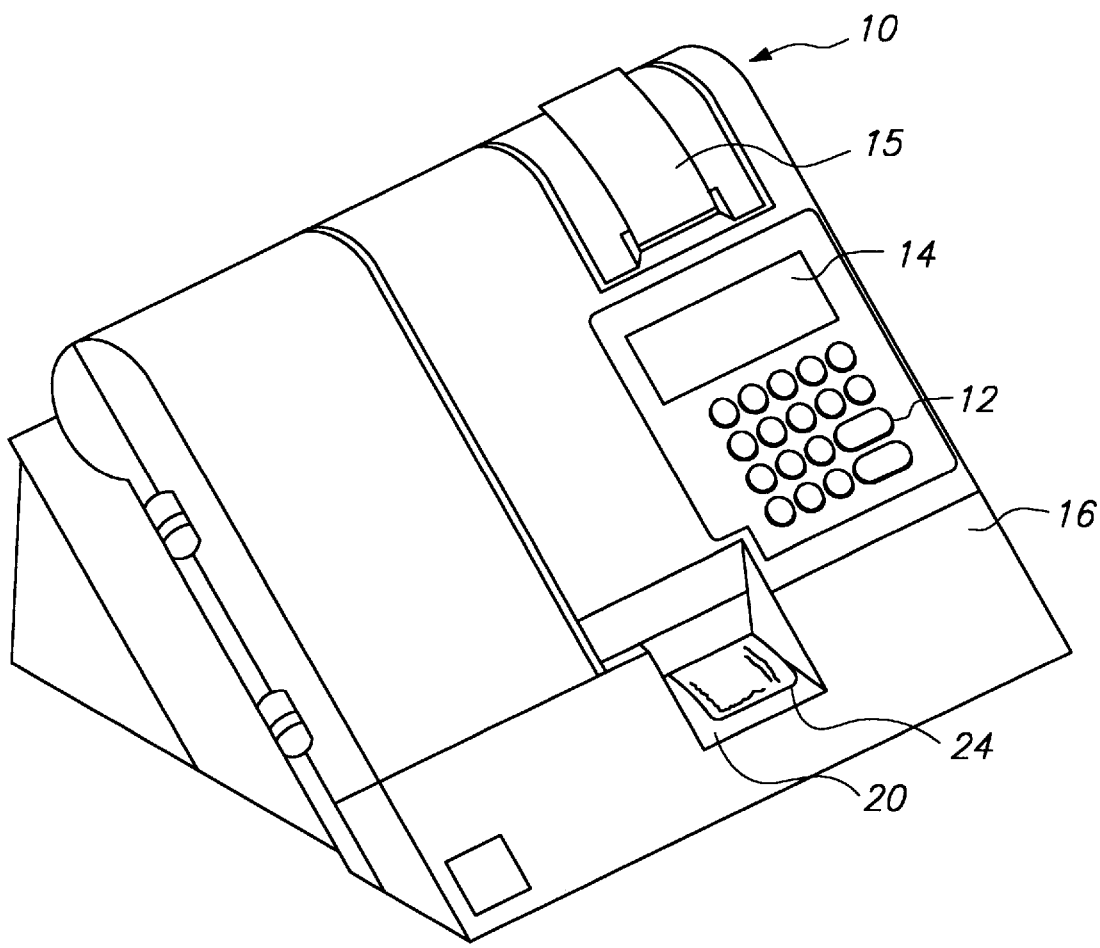
FIG. 1 shows an exterior perspective view of the electro-optical analytical instrument in accordance with an embodiment of the present invention.
Figure 2:
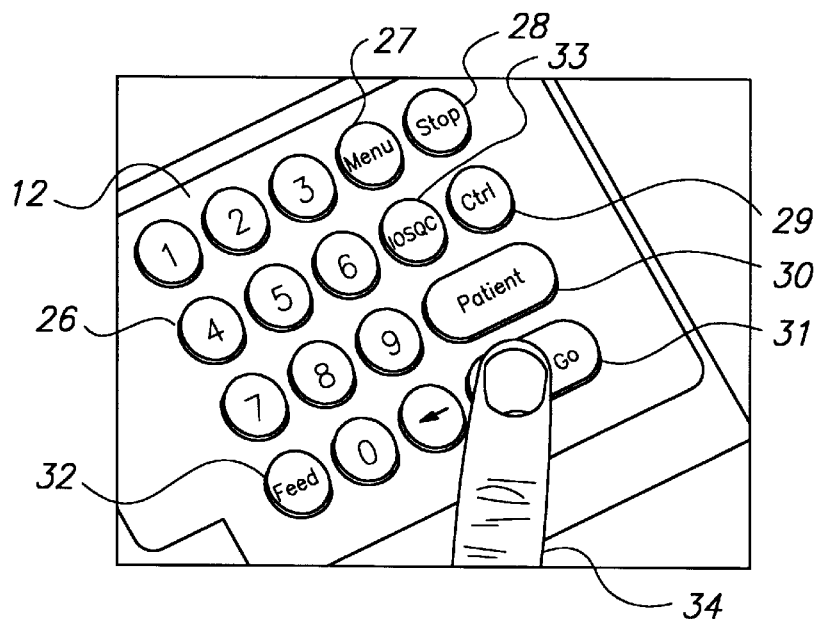
FIG. 2 shows an enlarged area of the instrument keyboard.

Referring to FIG. 1, there is shown an exterior perspective view of an embodiment of the inventive electro-optical analytical instrument 10, also referred to as a In-Office System (IOS), in accordance with one aspect of the present invention. The instrument has an operator keyboard or keypad 12 by which an operator or user may enter data including parameters, instructions, commands, and otherwise generally control operation of the instrument 10. The keyboard 12 is shown in the enlarged representation in FIG. 2, includes several number keys or buttons 26 that provide means for entering numerical information such as the patient identification number and user identification number, and several special keys that provide means for entering other information or commands. The menu 27 key provides access to user options such as setting date and time or replacing buffer. Other features of the keyboard include a stop key 28 to escape or cancel the current operations, the control ("ctrl") 29 key to start a control procedure, a patient key 30 to start a patient test procedure, an enter/go key 31 to signal the start of a test or the end of a keypad entry, an arrow key 34 to allow movement (scrolling) back through numbered entries, such as patient identification numbers, a feed key 32 to advance paper through the instrument's printer, and an IOSQC key 33 to start quality control tests which should be run periodically. Associated with keyboard 12 is an alpha-numeric multi-line liquid crystal display (LCD) 14 by means of which instrument status and, for example, test results may be visually displayed to an operator. A thermal printer 15 is provided for furnishing a printed record of the results of any tests performed by the instrument 10 including patient test and quality control results. The keyboard 12, alphanumeric display 14, and printer 15 are supported by an instrument housing 16, which also contains the mechanical, optical, and electrical apparatus necessary for operation of the invention.

Figure 3:
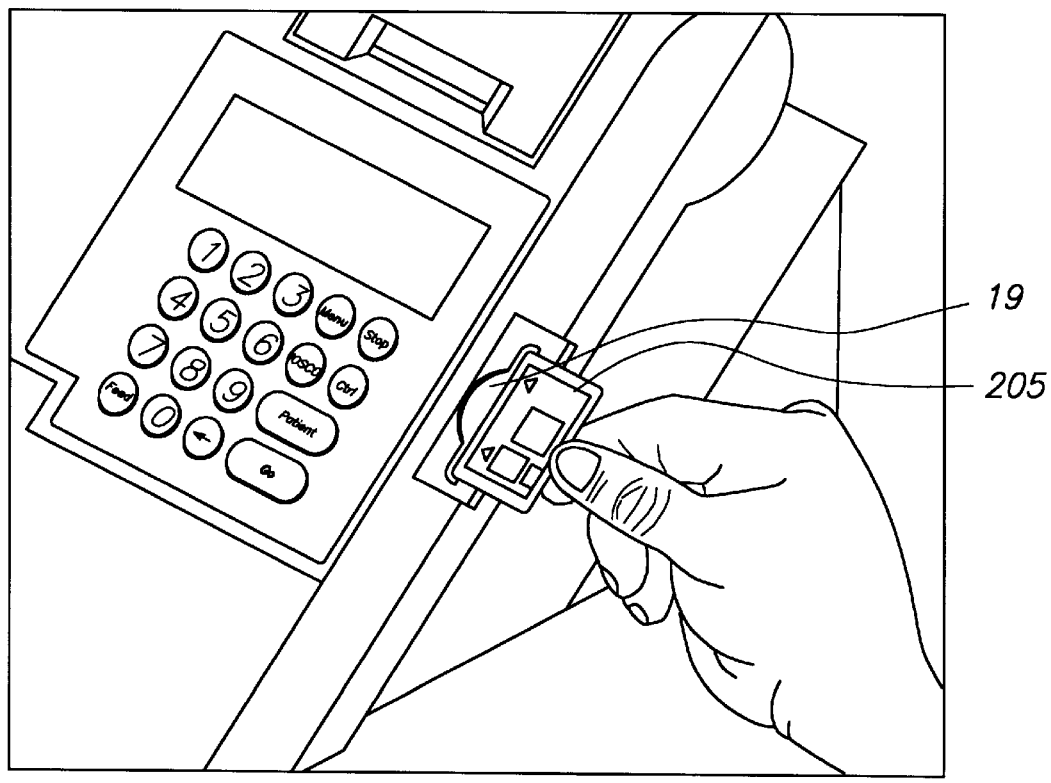
FIG. 3 is an illustration showing an alternate exterior perspective view of the instrument shown in FIG. 1, particularly showing the EEPROM insertion slot.

With reference to FIG. 3, which shows an alternative perspective view of the same instrument 10 illustrated in FIG. 1, there is shown adjacent to the keypad 12, the instrument housing 16 defines a first insertion slot 19, for receiving an EPROM software card, and a second insertion slot 20 for accepting one of various removable diagnostic, calibration, and control cartridges 24. Diagnostic cartridges suitable for use within the instrument 10 are disclosed in aforementioned issued U.S. Pat. No. 5,399,486, and copending patent applications having Ser. Nos. 08/179,749; 08/296, 489; 08/420,987; and 08/414,331 each of which patent and patent application are hereby incorporated by reference. The cartridges are further described hereinafter.

The diagnostic cartridges are designed to provide means for optical determination, particularly fluorescent determination, of an analyte sample. Typically the determination involves identifying the concentration of a particular chemical present in the sample undergoing test. The diagnostic cartridges have a port for sample introduction, and multiple channels which are in fluid communication with each other and which provide for transport of the sample and reagents to at least one incubation area. Transport within the channels is achieved by capillary action and is controlled by various fluid interruption means. In one embodiment, the instrument 10 desirably includes an air puffer device positionable proximate the sample introduction port that generates and applies a short puff of air into the port. This puffer urges the sample out of the sample introduction region and into one of the transport channels leading toward the incubation area. In other embodiments, mechanical means such as a rotatable impeller may be used to urge the sample into the transport channel. Such mechanical assistance is not required as the capillary action by itself draws the sample, however, provision of the puffer, impellers, pressure, or other mechanical assist is desirable because its provision within the instrument provides greater uniformity and reliability to fluid transport within the cartridge. The incubation area is where a fluorescent signal is produced by the combining of the sample with other members of the signal producing system which may be present in the cartridge. Other members of the signal producing system may be members of specific binding pairs, fluorescent production layers as described in U.S. Pat. No. 5,415,999 and lipid layers as described in U.S. Pat. Nos. 5,156,810 and 5,268,305, the disclosures of which are incorporated by reference. The generated optical signal is related to the presence and concentration of analyte. The cartridge desirably includes a waste reservoir downstream from the incubation area to receive fluids. Once inserted into the instrument 10, the cartridge 24 is positioned therein by a carriage mechanism, the details of which are described hereinafter.

The amount of fluorescence generated by the reaction in the cartridge is detected and analyzed by instrument 10. As is described hereinafter, a light source within the instrument 10 illuminates the sample and a photo-multiplier tube records the emitted fluorescence. In one embodiment of the invention, a plurality of emitted florescence measurements are taken at predetermined time intervals. Assay results relating to sample concentration are generated and optionally displayed or printed shortly thereafter.

Figure 4A:
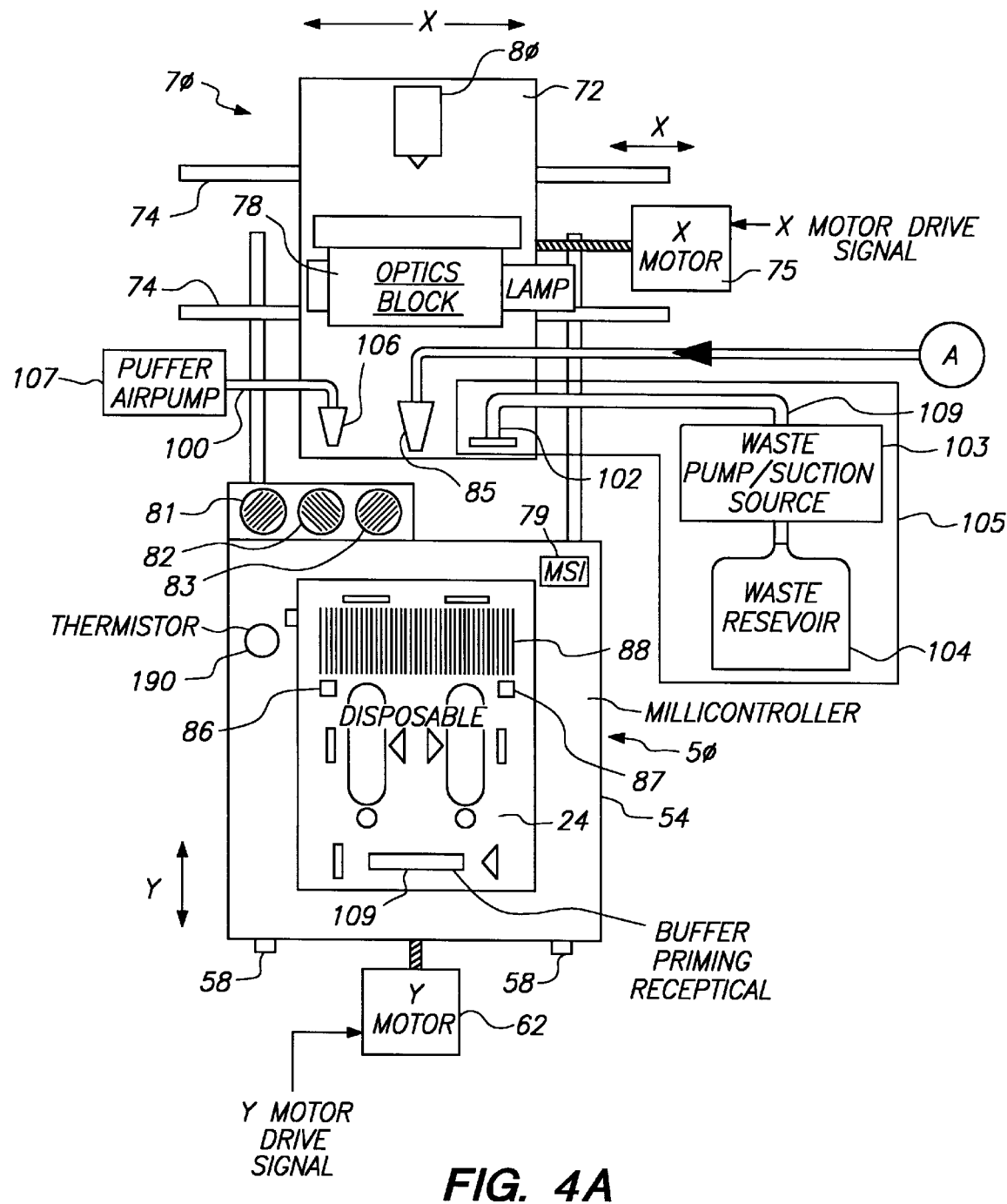
FIGS. 4A–B provide a simplified schematic representation of the principal optical and mechanical components included within a preferred embodiment of the analytical instrument.
Figure 4B:
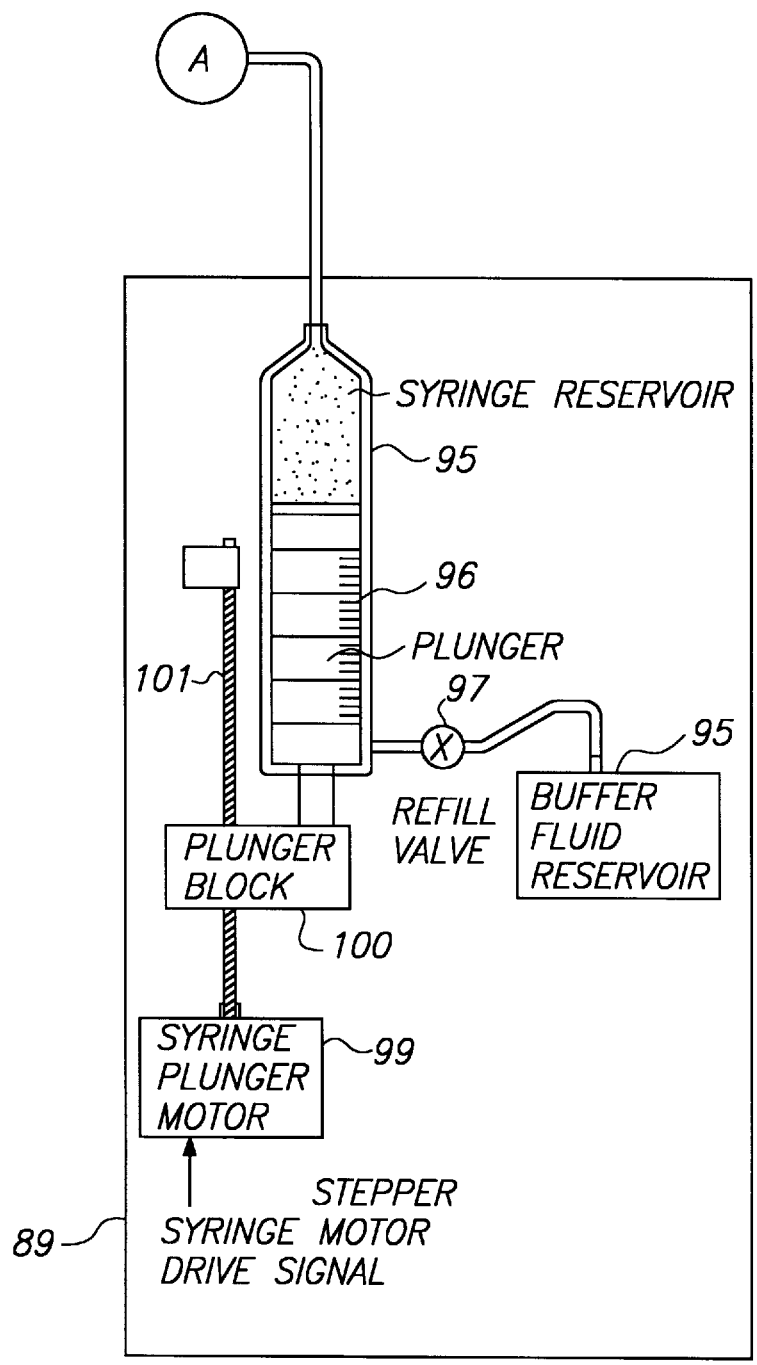

FIGS. 4A–B provide a simplified schematic representation of the principal optical and mechanical components included within the instrument 10. A cartridge carriage 50 for receiving the disposable cartridge 24 after insertion into slot 20 (FIG. 1) is seen to include a temperature-regulated heating plate 54 mounted on a first pair of guide rails 58. The presence of the cartridge 24 upon the heating plate 54 is detected by a microswitch MS179, although it is understood that other means of detecting cartridge 24, i.e., such as by using optical sensors, may be employed without departing from the scope of the invention. The guide rails 58 define a path in a Y-direction within the plane of FIGS. 4A–B along which the cartridge 24 is transported by the plate 54. Platform 54 is driven by Y-axis stepping motor 62 driven by a conventional stepping motor driver that generates and provides a Y-motor drive signal. The platform is movable under the control of the microcontroller in the ±Y-direction only.

In one embodiment of the invention, one or more reference patches (actually the equivalent of a portion of a cartridge as described later) having a known predetermined amount of responsive fluorophore are provided on or adjacent to the heater plate and attached to the carriage 50. In one embodiment of the invention, the reference patches are made by mixing the chemical "Benzoxazole" made by Exiton of Dayton, Ohio at known concentrations with a poymer resin, injecting the mixture into the cartridge 24 and machining the patches to size after the resin-Benzoxazole mixture has hardened. Each patch will contain a different concentration of the Benzoxazole which has a peak emission at about 450 nm and responds to an excitation at 365 nm. For example, the two patches may respectively be at a low concentration and at a high concentration so that the range of the PMT response may be measured and calibrated. This patch is used to calibrate the instrument, for example to correct for an offset, in a manner described later. The preferred embodiment of the invention includes at least two and preferably three reference patches 81, 82, 83 so that a linear calibration curve may be developed with two patches, and at least a limited class of non-linear calibration curves may be developed with three patches and the florescent readings obtained therefrom.

Also shown in FIG. 4A is an optics carriage 70 for positioning an optics platform 72 in a horizontal plane over the plane occupied by the cartridge carriage 50. The carriage 70 includes guide rails 74 for transporting the platform 72 in a direction parallel to an X-axis oriented perpendicular to the Y-direction traversed by carriage 50. As shown in FIG. 4A, platform 72 is driven along guide rails 74 by an X-axis stepper motor 75. Mounted on platform 72 are a set of analysis and calibration tools including an optics block 78, bar code reader 80, and buffer solution dispensing nozzle 85, an air puffer nozzle 106, and a waste suction fitting (including a rubber O-ring) 102. These "tools" are movable under the control of the microcontroller in the ±X-direction. The combined movements of the carriage 50 and carriage 70 provide means for moving any of the tools into the appropriate spatial relationship with cartridge 24. Typically the puffer nozzle 106 and the buffer dispensing nozzle do not contact the surface of the cartridge 24, however, the O-ring portion of waist suction nozzle 102 may be brought into contact with the surface of the cartridge such as by using an electrically operated solenoid, mechanical cams, stepper motors, and the like motional means. An initial description of the function of each of the devices mounted on the optics platform 72 is set forth in the following operational summary of the instrument 10.

FIG. 4A also illustrates the buffer solution supply system 89, and the waste evacuation system 105. The buffer solution supply system 105 includes a buffer fluid reservoir 95 that holds a predefined volume of buffer solution. Reservoir 95 is coupled to a syringe 96 through tubing and a syringe refill control valve 97. Syringe 96 has a syringe reservoir defined by the interior walls of the syringe and the location of a tip of plunger 98 which seals to the walls of the syringe body in conventional manner, such as with an O-ring seal. Plunger 98 is driven by plunger stepping motor 99 via lead-screw 101 and threaded plunger drive block 100 in a forward direction to dispense the desired amount of buffer solution to the cartridge 24 via nozzle 85. Plunger 98 may also be driven in the opposite direction so that the buffer in the plunger can be replenished from the buffer fluid reservoir 95.

The waste evacuation system provides means for evacuating fluid components from the cartridge. In the exemplary embodiment, a waste pump or suction source 103 withdraws fluid from a waist port on the cartridge into waste reservoir 104. Preferably, the volumes of the buffer fluid reservoir and the waste fluid reservoir are the same so that the waste reservoir will not overflow. The syringe 96 is provided to more accurately meter the buffer solution than would normally be possible from a fluid reservoir itself The syringe may be provided with a priming mode such that the stepper motor 99 is advanced to deposit a small volume of buffer into a priming reservoir 109 in the cartridge so that any air bubbles that may have been introduced into the nozzle 85 or into the tubing are eliminated before metering the buffer solution into the cartridge.

Figure 5:
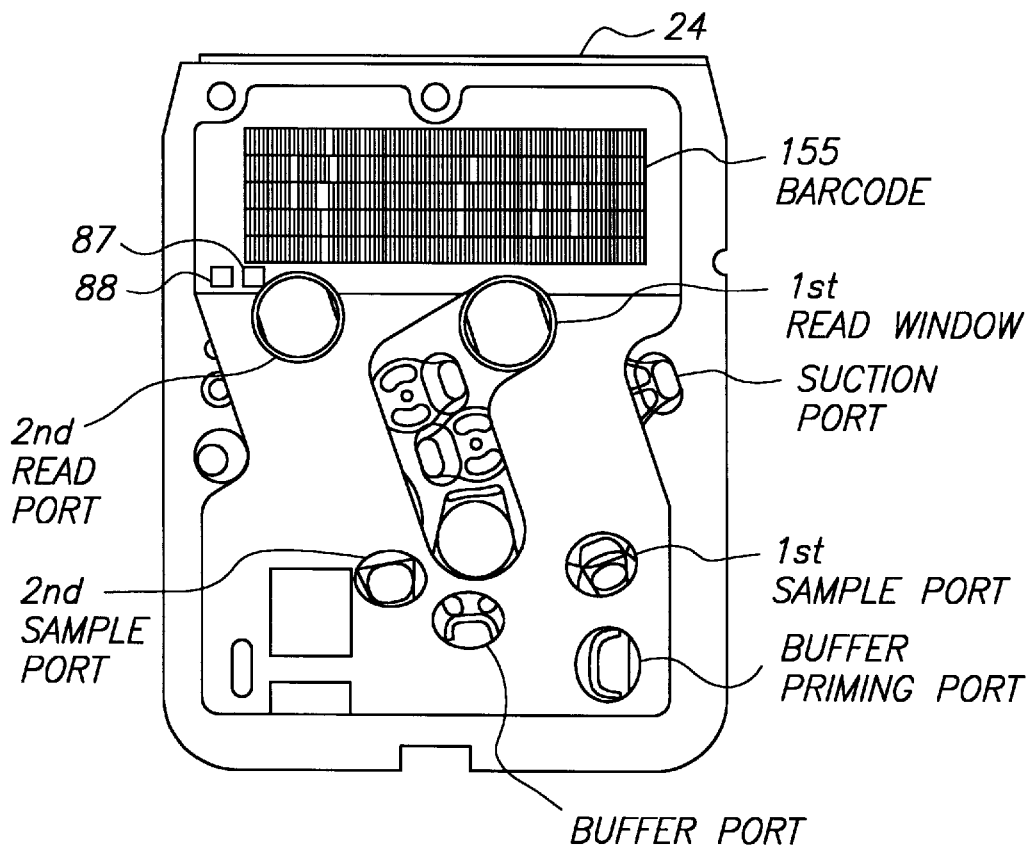
FIG. 5 is an illustration of portions of an exemplary removable cartridge for use with the instrument of FIG. 1, including several ports for the introduction or extraction of fluids and a bar coded region for placing machine readable information for use by the inventive instrument.

In a preferred embodiment the instrument 10 is operative to analyze, based on measurements of fluorescence, a sample contained within the diagnostic test cartridge 24 inserted therein. A test is initiated upon insertion by a user of the cartridge 24, generally absent the sample to be analyzed, into the slot 20. The bar-code reader is optionally calibrated by moving the maximum black calibration patch 86 adjacent to the bar code to the bar code read head and measuring the reflected light and then aligning the maximum white calibration patch 87 to the bar code reader head and measuring the reflected light, and setting a decision threshold about half way between the maximum black and maximum white values. An identifying bar code label 88 affixed to the cartridge 24 is then scanned by bar code reader 80 in order to ascertain various information such as the type of test to be performed, the calibration and correlation coefficients, cartridge type, cartridge lot number and expiration date, physician parameters, reference zone high and low values, and a error detection checksum value. The structure of an exemplary bar code for a IOS Test Cartridge is illustrated in FIG. 5, and an exemplary mapping of the regions on a different bar code are illustrated in FIG. 6. The four T4 coefficients correspond to the a, b, c, and d coefficients in the Rod Bard expression $y=(a-d)/(1+(x/c)^b)$. The two TU coefficients correspond to the a and b coefficients in the linear expression $y=a+bx$. Regression analysis (linear or nonlinear) using these equations to determine the concentration of the analyte in the sample based on the time rate of change of the florescence in the irradiated sample as described in greater detail hereinafter.

Next, the user is prompted via alphanumeric display 14 to enter, for example, patient identification information or other information relevant to the test using the keypad 12. The cartridge is returned to the front of the instrument 10 through slot 20 by the cartridge carriage 50. The operator then adds a liquid patient sample (for example, up to about 50 microliters ($\mu$l)serum) to at least one inlet port and to each of two inlet ports for two assay tests defined by cartridge 24. The cartridge 24 is the then retracted into the instrument 10 by the carriage 50, at which time the bar code label is again scanned by bar code reader 80. The information from the first scan may optionally be stored so that re-reading the bar code is not necessary, however, the bar code is preferably read the second time to verify that the cartridge has not been (accidentally or intentionally) removed and exchanged.

Once the sample has been provided and the cartridge 24 has been positioned within the instrument 10, the sample within cartridge 24 is incubated at a controlled temperature for a predefined interval which may generally depend on the test protocol (e.g., 10 minutes for a typical test) by heater plate 54. A buffer solution contained within syringe reservoir 95 (FIG. 4) is then dispensed into cartridge 24 by dispensing nozzle 85 through one or both of the two cartridge inlet ports. The dispensed buffer may serve a variety of purposes depending on the test protocol, including serving to dilute the sample to a suitable viscosity and/or concentration, for example.

The sequence of the subsequent steps depends on the type of assay being performed. These steps optionally include the instrument adding buffer to rehydrate dried reagents in the cartridge, i.e. substrate, adding wash buffer and aspirating to remove extra components from portions of the cartridge, mixing of the various components, and initiating flow of fluid through fluid interruption means located in the cartridge by increasing the momentum of the agitation means or by an air or gas puffer mechanism 106, 107, 108. At predetermined intervals during the assay, the instrument 10 may also be programmed and controlled to performs self-checks on the performance of the cartridge. For example, after the buffer is added to dilute the sample, the instrument reads the fluorescence in the incubation area. An abnormal fluorescent signal at this point may indicate that a fluid interruption means in one of the fluid communication channels connecting the sample inlet port and the incubation area did not work properly and sample had prematurely moved into the incubation area. As is described below, optics block 78 then "reads" the sample in order to measure a baseline value of fluorescence.

Briefly, optics block 78 operates to read the sample by projecting excitation light over a predetermined and typically narrow range of wavelengths corresponding to an excitation band for the particular fluorophore used to tag the sample analyte. The fluorophore has an emission band of wavelengths for the fluorescent light emitted in response to excitation by incoming light within the excitation band. The light source 110 within optics block 78 used to produce the excitation light will preferably be of sufficient intensity within the excitation band to induce a relatively high level of fluorescent emission within the emission band. This increases the signal which is the object of the quantification efforts, thereby increasing signal to noise ratio and improving sensitivity. In a preferred embodiment the light source 110 comprises a mercury vapor lamp which for emits light over a relative broad spectral range including the flourophore excitation wavelength band. In the exemplary embodiment, the light source is driven by a 10 kilohertz (KHz) sinusoid between about zero and about +5 volts. The 10 Khz signal is also chopped or switched on and off at about 32 Hz, so that the DC component of ambient light may be more readily filtered and not interfere with the measured fluorescence or reference signals. The switching transient is such that when the 10 Khz driving signal is turned on, the lamp requires about three of the 10 Khz cycles to reach a quiescent light output, and similarly requires about three of the 10 Khz cycles to extinguish when turned off These transient effects are insignificant compared to the PMT settling time.

Lamps of the type described are commercially available. For example, the *Handbook of Optics,* Walter G. Driscoll, and William Vaughan editors, McGraw-Hill, 1978 contains a description of Optical Radiators and Sources, at pages 3–1 through 3–83, and is hereby incorporated by reference.

The modulated and chopped light is then directed through an excitation interference filter having a passband included within the fluorophore excitation band and a lens to collect light from the lamp. A spectrally selective beamsplitter, such as a dichroic beamsplitter is provided which reflects the majority of the filtered excitation light to the sample. A cartridge lens 116 is positioned to accept the light reflected from the beamsplitter and focus it upon the region of the cartridge 24 holding the sample. The cartridge lens also serves to collect and collimate the fluorescent light emitted by the sample. The collimated fluorescent light from the sample then passes through the dichroic beamsplitter and is filtered by an emission filter designed to block light at wavelengths outside of the fluorophore emission band (nominally centered at 440 nm), and is focused by a detector lens upon a signal detector PMT 98.

During an assay determination, the signal from PMT 120 is read during an ON cycle and during an OFF cycle of the 32 Khz chopper. The ON cycle and OFF cycle PMT signals from adjacent cycles are advantageously fed to a differential amplifier so that the baseline signal (or dark current) read during the OFF cycle is effectively subtracted from the desired ON cycle PMT signal. The intensity of the reference beam seen at the reference detector 115 is also measured at each sampling time so that any variation in the intensity of the sample excitation beam may be compensated. In the preferred embodiment of the invention, the emission detector is a PMT which has much greater sensitivity than the Silicon Photodiode used for the reference beam detector. The greater sensitivity is important because the florescent emission is typically much lower intensity than the reference beam intensity. The integration times for the PMT 120 and Silicon Photodide 115 are adjusted so that the detected signal from each is in the optimal range, that is above the noise level of the respective detector, below saturation, and preferably in the region where the response is fairly linear.

Each set of emission (PMT) signals (On and OFF cycles) and Reference Beam Signals (ON and OFF cycles) are repeated several times. In one embodiment of the inventive method, the measurements are made periodically for 40 cycles of the 32-Hz lamp modulation. (Note that although the ON and OFF measurements are made sequentially, they are substantially simultaneous in time relative to expected variations in the characteristics of the instrument and changes or progression of the reaction in the cartridge 24. Note that because the Reference channel and the emission channel operate in paralle, the reference and emission measurerments are simultaneous, only the ON and OFF measurements are slightly delayed relative to each other (delayed by 1/32 second). The time interval (T) between sequential sets of measurements and the total number of measurements (N) may be set, such as by programming the instrument, in order that the optimum mesurements are collected for the correlations from which analyte presence and concentration may be determined. The total time for a single assay will depend on the type of assay and the particular reagent system and protocol required by that assay. For one particular assay, a total of about 24 minutes are required to perform the assay. Of course other assays may be longer or shorter. In one embodiment of the inventive method, the ratio of the output of the analog-to-digital converter $ADC_{PMT}$ or $ADC_{REF}$ outputs are related according to the expression:

$$\text{Ratio} = \frac{(ADC^i)_{PMT} - (ADC^0)_{PMT}}{(ADC^i)_{REF} - (ADC^0)_{REF}}$$

Optics block 75 also determines a reference level of fluorescence. Based upon the measured baseline and reference fluorescence values a sample analyte concentration is determined by comparison with a correlation data electronically stored within the instrument 10 in the form of for example, a look-up table, and/or read from the cartridge bar code itself. (In fact, the correlation between the measured values and the assay determination comprise stored nominal correlation coefficients and refinement correlation coefficients that adjust for the differences detected in the reference patches (to calibrate for the optical system) and the differences detected in the calibration cartridges (to calibrate out the effects of cartridge lot variations). These calibration adjustments are automatic and make the IOS instrument 10 a very stable instrument.

Particularly significant, is manner in which the instrument is factory (manufacturer) calibrated initially, and continually self-calibrating after delivery to the user by virtue of the built-in stage reference calibration patches which provide the data to generate adjustments or corrections to the original stored factory calibration before each assay, and as a precaution at the end of the assay, to assure stable operation of the instrument 10 during the assay. Furthermore, the each cartridge includes bar-coded parameter for adjusting the correlation coefficients for the cartridge physical characteristics (e.g. transmission characteristics of the cartridge read window, possible self emmission of the cartridge material, and the like). The correlation coefficients in conduction with the appropriate computational expression (eg. linear, Rod Bard, exponential, or any other relationship between reaction rate and chemical concentration that can be stored in a Look-up- Table in ROM or RAM) may be used. Each cartridge 24 also has an expiration date read by the bar code reader, so that expired cartridges that may have undergone aging or other undesireable effects cannot be used. Since any portion of the assay system and procedure are self calibrating or employ "standards" directly tracable to the factory and factory calibrations, the assay results are extremely accurate, precise, stable, and worthy of a physician's trust. Conventional assay instruments and methods typically rely on user calibration in the field, and do not self calibrate with each assay performed.

Once an assay determination has completed, the resultant assay result, such as the analyte concentration value is then displayed to the operator via the display 14, and is printed by printing unit 15. Alternatively, a numerical analysis routine may be employed to determine concentration by substituting the measured change in fluorescence into an empirical expression relating detected fluorescence and/or rate of change of florescence over a plurality of measurements to concentration. One such numerical routine is described in further detail below in connection with a description of a software control program utilized to govern operation of the instrument.

II. OPTICAL SUBSYSTEM

The Optical system is now described in greater detail. The In-Office System (IOS) instrument 10 includes an optical system to measure the concentration of various chemicals in a test sample, such as for example a sample of patient's blood. During development of he sample assay, the chemical concentration is correlated (in a manner described hereinafter) with the amount of light that is emitted (or fluoresced) from the sample, when the sample is "excited" from a lamp. Physical mechanisms and chemical processes for creating the appropriate conditions to emit light or other radiation from an irradiated sample or sample system are known and not described further. Measurements of emitted light are used in the inventive apparatus and method including the inventive correlation procedures to infer the chemical concentration of the analyte in the sample.

The optical subsystem is now described with reference to the optical schematic in FIGS. 7A–B. The optical system includes the optics which comprise the instrument itself, and the removable cartridge which confines the sample and sample system under test, and in some embodiments of the invention provides for calibration of the instrument. In this scheme, the optical instrument 10 is the active optical portion of the instrument/cartridge system, and the removable cartridge 24 is the passive optical portion in that it provides a target for the instrument optics to act upon. The manner in which the instrument presents light to the cartridge, and processes light it receives from the cartridge is now described.

Figure 7A:
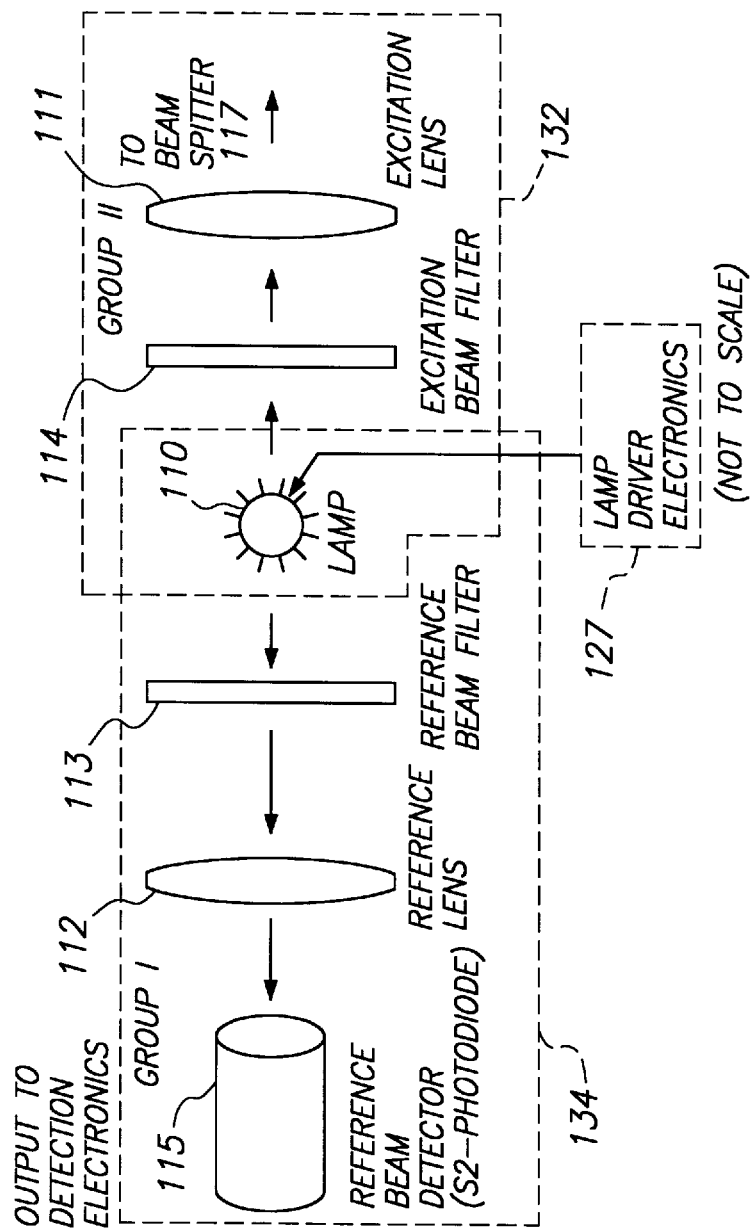
FIGS. 7A–B are optical schematics showing an arrangement of optical components in a preferred implementation of an optics block included within the inventive instrument.
Figure 7B:
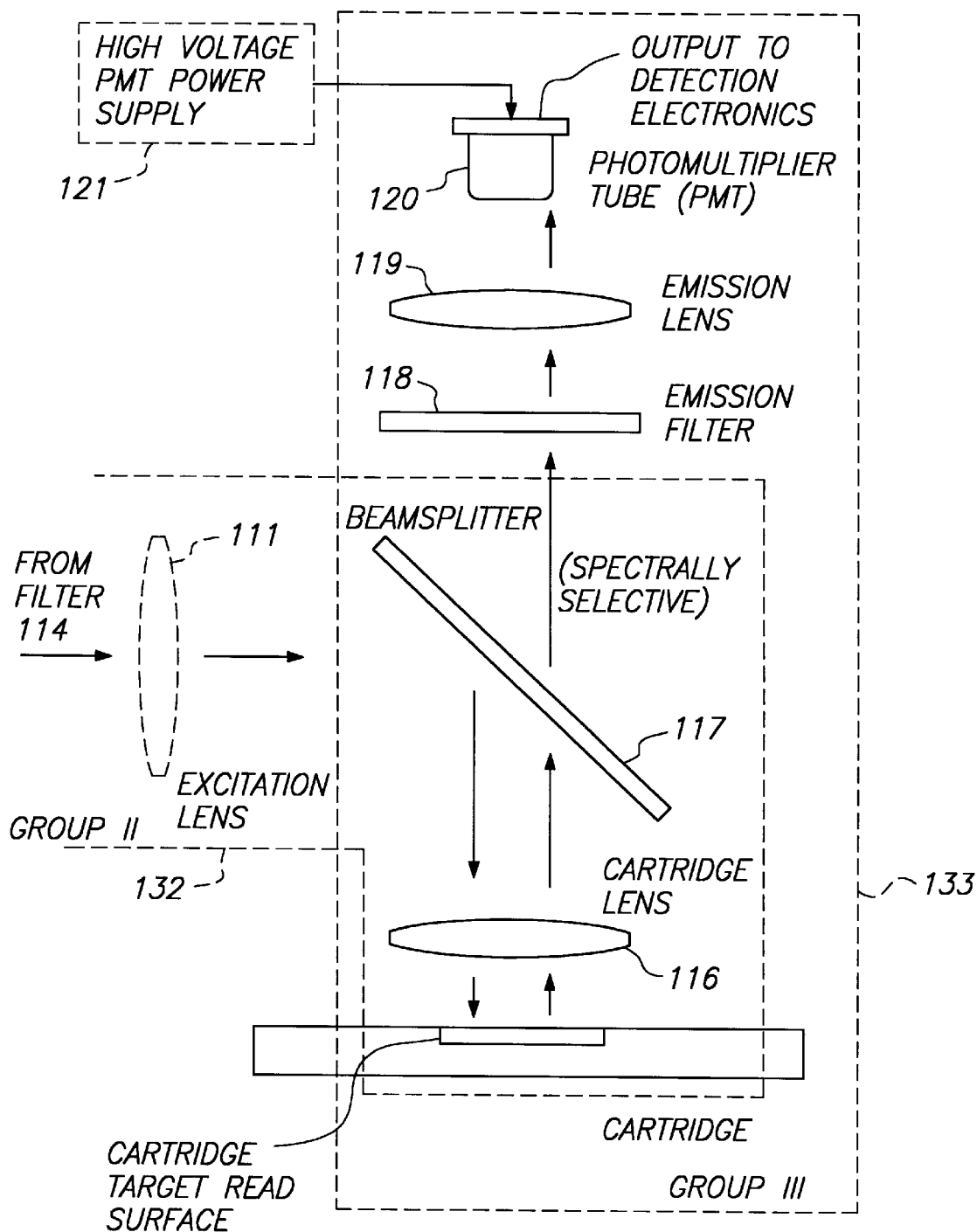

The arrangement of the optical components are first described with respect to the optical schematic diagram in FIGS. 7A–B. Then the operation of the optical path will be described.

For ease of description, the optical components are organized into three functional groups: Group I, the reference optics group 131, including the lamp 110, reference lens 112, reference filter 113, and reference detector 115 (here a silicon photodiode); Group II, the excitation optical group 132, including the lamp 110, excitation lens 111, excitation filter 114, dichroic beamsplitter 117, cartridge lens 116, and removable cartridge 24; and Group (III) the emission collection optical group 133, including the cartridge 133, cartridge lens 116, dichroic beamsplitter 117, emission filter 118, emission lens 119, and emission detector photomultiplier tube (PMT) 120 and its assciated high-voltage power supply. Some of the optical components function and therefore appear in more than one group.

Various types of cartridge targets may be employed depending on the sample analysis system being employed for particular tests. A common feature of all of the cartridge targets in the preferred embodiment of the invention is that they include an emissive material which emits light with wavelengths near about 440 nm when light near about 365 nm is directed on them. From an atomic level, various atoms in the cartridge targets absorb 365 nm light. In order to absorb this light, the atom's electrons move to (or are excited to) to states that allow them to hold the additional energy. However, these are not the atoms' normal electron energy states, so the electrons quickly revert back to their original states. To do this, the electrons must release the energy that they earlier absorbed. The electrons release this energy by emitting light at 440 nm. The invention is applicable to other wavelength ranges so long as the excitation radiation wavelength is sufficiently separated from the emitted radiation so that the dichroic beamsplitter can substantially block one wavelength while passing the other wavelength.

Since the 365 nm light excites the electrons to higher energy states, the 365 nm light is referred to as excitation light, and the optics that direct this light are the "excitation optics". Similarly, since the 440 nm light is emitted from the cartridge targets, the 440 nm light is "emission light" and the optics that direct this light are the "emission optics". The reference optics monitor the lamp's strength, and the cartridge optics include the optical components which are common to both the excitation and emission optics.

There are three light paths through the instrument. The first light path is the Lamp Reference Light path. This reference path monitors the strength of lamp 110. The strength is monitored because the amount of emitted light depends on the amount of excitation light as the excitation light strength goes up, the emission light strength goes up. The relationship between excitation light strength and emitted light strength is linear up to a very high light strength. Beyond that point, the target (sample) begins heating and the atoms' energy states begin to change from the heat. When the relationship between the excitation and emission light become non-linear, the target is said to be "saturated".

The reference path has four components: Lamp 110 supplies the excitation light, reference lens 112 collects the lamp light from a predetermined region of the lamp, reference filter 113 filters out a relatively narrow wavelength band from the broad polychromatic bandwidth of the lamp to present a narrower band of excitation wavelengths to reference detector 115 which measures the strength of the excitation light. In the preferred embodiment, the lamp is a lamp such as a flourescent or incandescent lamp.

The reference filter 113 is matched to the excitation filter 114 so that the light that reaches reference detector 115 has a predetermined relationship with the light that reaches cartridge 24. Preferably the reference filter and the excitation filter have the same filter transmission characteristic.

The characteristics of reference filter 113 is now described in some detail. Lamp 110 creates light in a broad range of wavelengths. For example, common incandescent lamps may emit over the entire visible spectrum, such as from about 300 nm to over 700 nm of varying spectral character. Most of the light wavelengths are useless as excitation light since the target's atoms can only absorb certain known wavelengths. Light at other wavelengths actually hurts the emission of light, because the target will absorb some energy from these wavelengths which may heat the target, thereby changing the targets electron's light absorption and emission behavior.

In one embodiment of the invention, the optical system is configured or tuned to illuminate the target with excitation light having a nominal wavelength of 365 nm (actually between about 355 nm and about 375 nm). If the heating causes atomic changes in the target that result in a shift in the optimum excitation wavelength, say from 365 nm to 385 nm as a result of heating, then the optical system (including the filters) will no longer properly excite the target and the emission detector will not receive any emission light.

Figure 8:
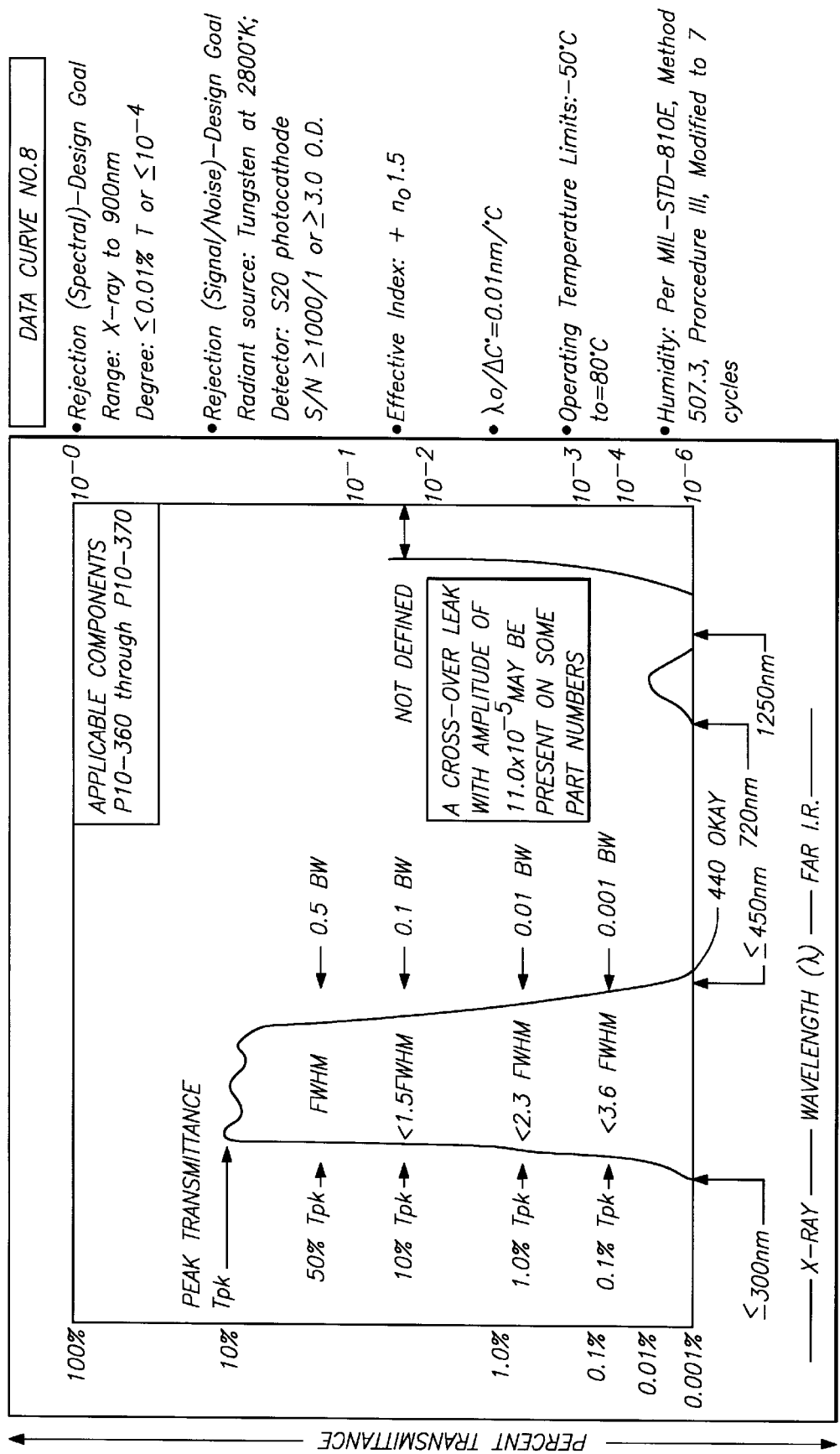
FIG. 8 is an illustration of the transmittance versus wavelength for the reference beam lens and the excitation beam lens according to one embodiment of the invention.
Figure 9:
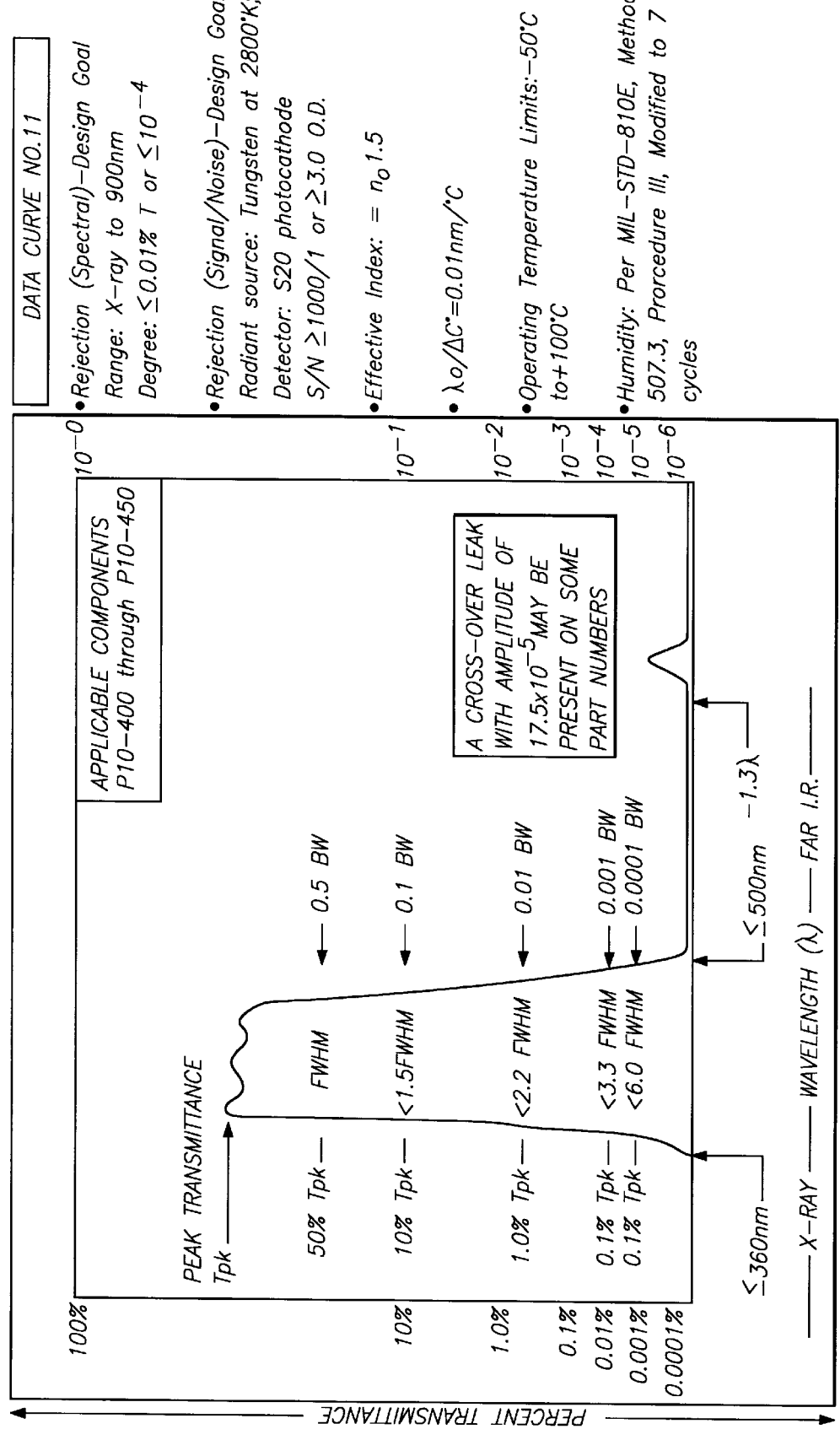
FIG. 9 is an illustration of the transmittance versus wavelength for the emission beam lens according to one embodiment of the invention.
Figure 10A:
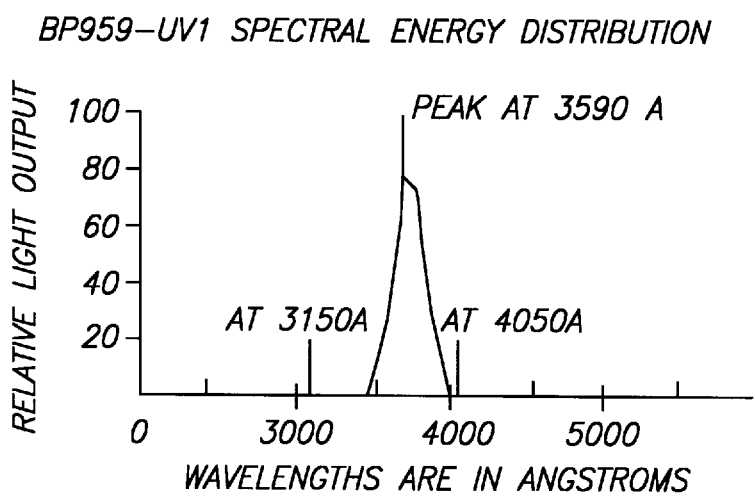
FIGS. 10a–10c are illustrations showing characteristics of a suitable lamp for use as an illumination source in the inventive instrument.
Figures 10B, 10C:
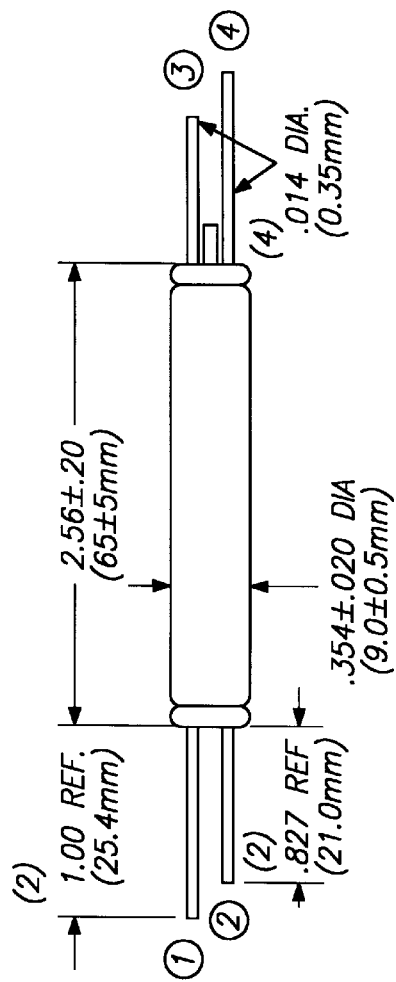

An exemplary filter bandpass characteristic for the reference 113 and excitation 114 filter is illustrated in FIG. 8 and and the bandpasss characteristics of the emission filter 118 is illustrated in FIG. 9. The filters have maximum transmission at about 365 nm, and pass about 50% of the light incident at between about 360 nm and 370 nm, while outside of about 365 nm and 375 nm, only about 10% of the incident light is transmitted. For example, in a preferred embodiment of the invention, a miniature florescent lamp having a spectral output from about 315 nm to about 405 nm, and having a peak output at about 365 nm is used (For example, the BF959-UV1 miniature lamp made by JKL Components Corporation, 13343 Paxton Street, Pacoima, Calif. 91331 is a suitable lamp). Filters 113, 114 provide means for selectively transmitting only the wavelengths that excite the atom's electrons, and for blocking the other wavelengths outside of the passband. This will optimize the effect of the excitation light on the cartridge target. The nominal fluorescence wavelength band of 440 nm is outside the passband of the reference and excitation filters.

With further reference to FIGS. 7A–B, the Excitation Light Path which provides means for exciting the target's electrons into higher energy states, so these states can decay and produce emitted light. The excitation optical path includes six components. The first three components were copied in the reference light optics, so the reference detector will get a valid measurement of what the cartridge will see. The four components are: lamp 110 already described, an excitation lens 111 which collects light from about a 7 mm diameter area at the lamp's center and redirects the light into a collimated beam, an excitation filter 114 for filtering out the excitation wavelengths from the lamp light as already described, a spectrally selective beamsplitter, such as a dichroic beamsplitter, which reflects about 90% of the filtered excitation light incident on it, a cartridge lens 116 for refocussing the collimated beam onto a predetermined area on the cartridge target 24. In one embodiment of the invention, the predefined area is about a 7 mm diameter spot.

Figure 11:
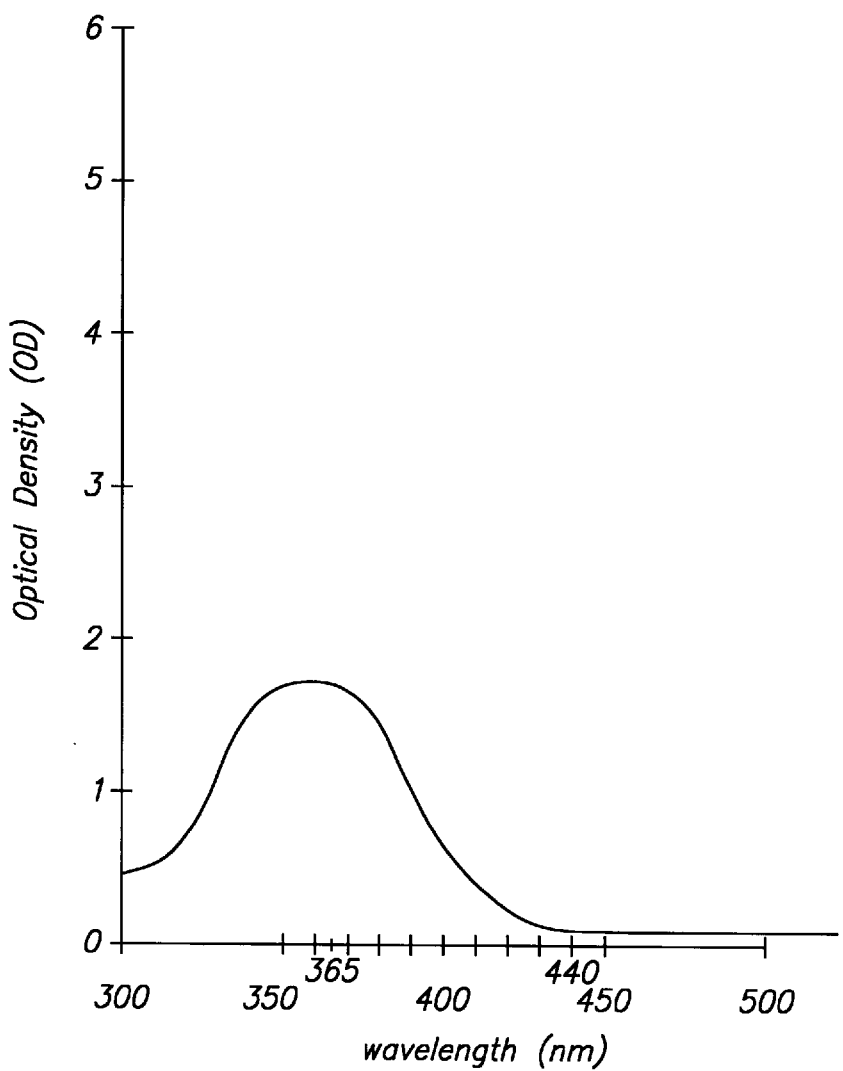
FIG. 11 is an illustration of the optical density versus wavelength for the beamsplitter used in an embodiment of the inventive instrument.

The spectrally selective beamsplitter 117 is now described in greater detail with respect to FIG. 11 which shows an exemplary transmission/reflection characteristic as a function of incident wavelength. The beamsplitter's optical spectral transmission/reflection characteristics are chosen such that the beamsplitter reflects at least about 90% of the incident excitation light having a nominal wavelength of about 365 nm going toward the cartridge target 24, and transmits at least about 80% of the longer wavelength (nominally about 440 nm) emitted light impinging on the beamsplitter 117 from the cartridge target. Of course, a beamsplitter having different amounts reflection and transmission may be used so long as the beamsplitter adequately separates the excitation and emission wavelengths, and provides for a strong enough signal at the PMT and sufficiently high signal to noise ratio to provide reliable, accurate, and precise assay determinations.

In one embodiment of the invention, the beamsplitter 117 is a filter formed with a dichroic-microplasma coating. The cut-on wavelength (at 50% of transmission peak) is nominally 390 nm, and the reflection range at 45-degree orientation to the beam is about 350 nm to about 380 nm. The minimum reflectance is about 90% over the reflection wavelength range at 45-degree incidence. The minimum transmission is about 80% over the transmission range from about 400 nm to about 550 nm. All of these performance figures hold over the operating temperature range of −50 degrees C. to +80 degrees C., and for humidity pursuant to MIL-STD-810E, Method 507.3, procedure III, modified to 7 cycles. The diameter of the exemplary beamsplitter is about 15 mm and the beamsplitter has a thickness of about 1 mm. The minimum clear aperature is about 14 mm. Surfuace and coating quality are 80/50, F/F per MIL-F-48616.

The Emission Light Path provides means for collecting the light emitted from the cartridge's target 24 and for focusing the collected light onto the emission detector, here a sensitive PMT. The PMT will generates an electrical signal related to the number of photos collected. In the preferred embodiment of the invention, a PMT is used rather than a solid state detector, such as the silicon photo-diode used for the reference detector, because of the greater sensitivity provided by the PMT. Electronic detection circuitry (described hereinafter) transform the PMT output electrical signal into a digital number for the IOS's microprocessor to process.

The emission optical train includes six components. The first two components are identical to those already described for the reference light optics, that is they are shared. Identical or shared components are provided here so that the reference detector has a valid measurement of what the cartridge will see. If separate components were provided, even though nominally having the same characteristics, manufacturing tolerances and production variation might introduce errors into the measurement. While such errors could be calibrated out, using the same elements eliminates the problem.

The six components are: A target area or region of the cartridge 24, a cartridge lens 116 which here collects light from approximately a 4 mm×5 mm ellipse on the cartridge target and collimate the collected light to present to beamsplitter 117 which as already described, transmits about 80% of the emitted light incident on it. The emission optical train also includes an emission filter for filtering out the emission wavelengths from other background light or undesired emissions, an emission lens 119 for focusing the collimated emission light onto the PMT's active detection region which PMT transforms the collected the emission light into an electrical signal. A commercially available PMT is used in the exemplary embodiment having a active areas of about 8 mm×24 mm. The only optical significance to the elliptical shape of the emission light is that since the PMT's detector area is 8 mm×24 mm, it "sees" an elliptical area on the cartridge related to the magnification. Therefore, the PMT collects light from an elliptical area on the target. Optional optical stops may be employed in the optical train to limit the region of collection by the PMT so long as the optical masks do not introduce unwanted noise or background signals. Optical masking techniques are known in the art.

The cartridge optics are now described with respect to FIGS. 7A–B. The instrument optics as a whole are used to sense or measure different characteristics of the cartridge targets including characteristics of the cartridges themselves and/or substances contained in the cartridges. The optical system is designed to illuminate the cartridge target at about 365 nm and to collect and measure emissions from the cartridge at wavelengths at or near the 440 nm emission. In the inventive instrument and assay system and method, seven different cartridge targets are alternatively made available as desired. Each of these targets emits at 440 nm in response to adequate excitation at 365 nm.

Several different cartridge target types are now described by way of example, but not limitation, to illustrate the variety of assays that may be implemented with the inventive. apparatus and method.

A Patient Sample type cartridge 161 and the primary cartridge for which the instrument optics have been optimized, receives and holds a sample of a patient's blood serum at the focal plane of the excitation and emission optics. When the serum is moved into the cartridge read window (as described elsewhere), and the chemical processes have properly prepared the serum, the excitation light from the cartridge lens 116 shines on the serum, and emission optics collect the emitted light. Then the PMT transforms the photons of light into electrical signals that we have correlated to a chemical concentration. The chemical concentration is reported to the physician.

In one embodiment of the invention, a machine readable bar code 155 or a plurality of such parallel bar codes, such as may be provided by a printed label, is provided on each cartridge, including patient sample type cartridges. The bar-code contains information that tells the In-Office System (IOS) analysis software what the correlation constants (the correlations between light levels and chemical concentration) are for that particular manufacturing lot of cartridges. It also tells the IOS instrument what test is being performed so that for example, the instrument can set up parameters for the test including for example, incubation times and temperatures, reaction times, sampling frequency, and the like. The bar coded information may also be used to guide the user, physician, lab technician or other person using the IOS, exactly what steps to perform in order to accurately make the assay determination. The bar code may also include such information as an expiration date for the cartridge, which the instrument may recognize and as a result trigger a cartridge rejection mode and message to the user to provide a non-expired cartridge for the test. In one embodiment of the invention, the cartridge bar code is read before the sample is applied to the cartridge so that the use may be prompted and/or advised before a cartridge is used inappropriately.

FIG. 5 shows an exemplary embodiment of a cartridge bar code 155 including five separate bar code patterns arranged in parallel rows, including a map of the information into human readable form. The bar coded information, along with other test information parameters entered by the IOS user may also be printed on the printer or other report.

The Transfer Cartridge Type 162 is used to calibrate the instrument optics. In the inventive instrument, the optics are advantageously calibrated before the correlations between chemical concentration and emission light levels obtained from one instrument can be applied to another instrument. The transfer cartridge is substantially the same physical cartridge that we use for patient samples, but, instead of inserting blood serum sample or other patient sample into the cartridge and mixing various chemicals with it, a calibration sample made by premixing a plastic resin with certain chemicals is inserted into the cartridge. In one embodiment, a chemical such as Benzoxazole made by Exiton of Dayton, Ohio is used because it emits significant florescence between about 435 and 445 nm (the peak emission is at about 450 nm) when the nominal 365 nm excitation light illuminates it. Two different concentrations of the chemical are used in each cartridge, so a single cartridge can provide two different calibration points on each transfer cartridge. Although a single calibration point could be used, two calibration points of this type are desirable because it provides meas for calibrating the low and high intensity ranges of the instrument and analysis system.

Stage References 163 are essentially instrumentation optical (calibration) targets that are not in or on a removable cartridge. In one embodiment of the invention, the stage references are fabricated from transfer cartridges by using the same resin/chemical system and then cutting the read window containing the hardened resin/chemical mixture out of a transfer cartridge, and then mounting these read window cut outs to the translation stage inside the instrument 10. Stage references are located on the cartridge stage at the focal plane of the instrument optics. These references are used to recalibrate the instrument optics for each test. This advantageously eliminates errors in the optics due to lamp, filter, or PMT, or electronic components aging or other degradation. The stage references are calibrated by the transfer cartridge; i e., when the transfer cartridge calibrates the instrument optics, it is really calibrating the stage references. The locations of the stage references are illustrated in FIGS., 4A–B.

An In-Office System Quality Control (IOSQC) type cartridge 164 is also a type of transfer cartridge. The only difference between the transfer cartridges and the IOSQC cartridges comes from the IOS's software's response to the cartridge. The optical response of the transfer cartridges and IOSQC cartridges are identical. Users are instructed to perform an IOSQC test every day to ensure the instrument is operating properly. The only difference between and IOSQC cartridge and a transfer cartridge is that, when an IOSQC cartridge is inserted into the instrument, the instrument is not re-calibrated. Instead, the user is merely told whether the instrument is within calibration.

IOSQC cartridges are provided so that in the event that an IOSQC cartridge is damaged while outside the manufacturers control, the instrument cannot be inadvertently and erroneously mis-calibrated by the defective cartridge. Miscalibration would result in inaccurate assay readings. Since the IOSQC cartridge merely tells the user that the instrument is out of calibration, the user would request recalibration from a qualified technician or from the manufacturer.

The Wet QC cartridges 165 are merely patient sample cartridges, used in conjunction with predefined assay protocols and chemical samples with known light emission properties. They are used to verify that the instrument is performing properly with a wet sample (instead of the solid, plastic optical references in the IOSQC). Users are instructed to perform a Wet QC test once a week, to ensure the instrument is operating properly. Like the IOSQC, the Wet QC cartridges only tell the user whether the instrument is properly calibrated. The user is not allowed (i.e. prevented by software controls) to recalibrate the instrument.

The calibration cartridges 166 are basically like the IOSQC cartridges, except they are set up with many more concentrations of chemicals than the two concentrations in the IOSQC cartridges. Ten different calibration cartridges are currently available, with 20 different chemical concentrations that produce 20 different strengths of emitted light for the same excitation light. (There are two chemical concentrations per cartridge, just like the transfer cartridge). These cartridges are used to check the instrument optics's linearity so that the accuracy and precision of the chemical concentration measurements are maintained.

Finally, there are MU Cartridge types 165, that are used to calibrate the transfer cartridges. They are not typically used to calibrate instruments in the field because they are very fragile.

The IOSQC, Transfer, Patient, Wet QC, and calibration cartridge types are identified as such to the instrument via the bar-code label already described. They may also be identified to the user, by a human readable label, color coding, and the like conventional identification schemes. These cartridges are described in greater detail in the U.S. Patent Applications and Patents incorporated by reference.

Referring to FIGS. 7A–B, there is shown an arrangement of optical components corresponding to a preferred implementation of optics block 78. Included within optics block 78 is a light source 110 such as a UV fluorescent lamp, a mercury vapor lamp or a light emitting diode (LED) for emitting optical excitation light over a spectral range centered at a predefined wavelength in response to an electrical excitation signal E from driver electronics (not shown). The excitation signal E will typically be a sinusoidal wave at, for example, a frequency of 10 Khz and chopped by a square wave at a 50% ON/OFF duty cycle. This induces the lamp 110 to emit an optical excitation pulse during each of a sequence of ON intervals separated by a corresponding sequence of OFF intervals of equal duration. Typically, if the light strength is within an optimal range, as the strength of the light increases the strength of the emitted fluorescence linearly increases. However at a maximum light strength, the target fluorophore becomes saturate and the relationship is no longer linear. The lamp strength is chosen to be in an optimal range.

The photo-multiplier tube is mounted on first and second printed circuit boards (PCBs) 134 and 138. Also mounted upon the PCBs 134 and 138 are preamplifier networks (not shown) operative to amplify the signals produced by the detectors 98 and 120 in the manner described below.

In the preferred embodiment the optics platform 72 is horizontally translated relative to the cartridge carriage 50 so as to enable the bar code reader 80 to scan the bar code identifying label unique to each cartridge 24. Specifically, the bar code reader 80 will preferably include an optical emitter comprising a light source such as a light emitting diode (LED) or a mercury vapor lamp for illuminating each bar code label with visible light. The light reflected by the bar code label is sensed by a conventional read head such as, for example, a Hewlett Packard HEDS-1500. The emitter and read head of the bar code reader 80 will preferably be mounted upon a printed circuit board, upon which are also mounted bar code driver and detection electronics. Particular implementations of the driver and detection electronics are set forth below and illustrated in FIGS. 12, 13A–B, and 14.

III ELECTRONICS SUBSYSTEM

A. System Overview

Figure 12:
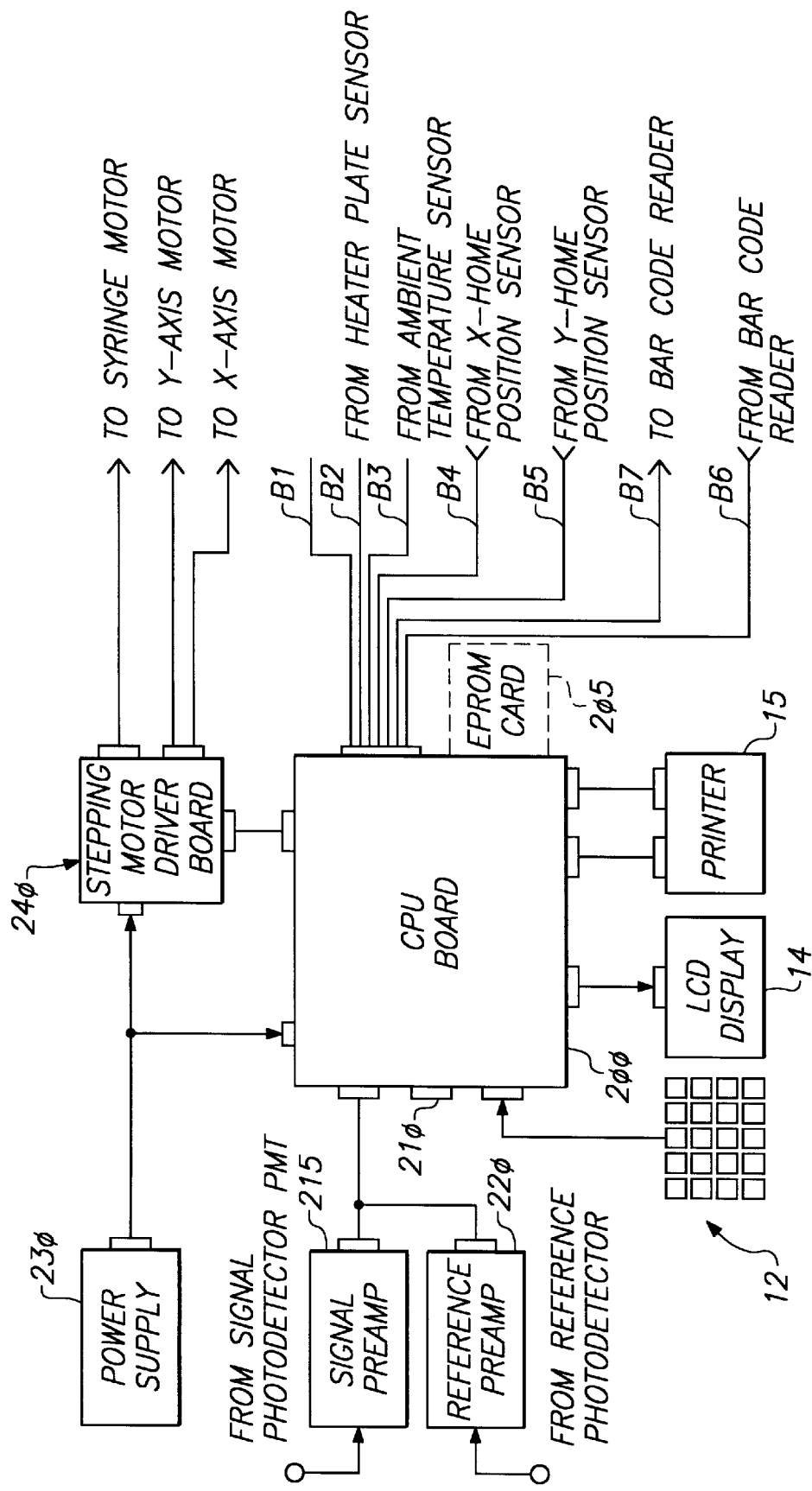
FIG. 12 shows a functional block diagram representation of an embodiment of the electronics subsystem used in controlling operation of the instrument.

FIG. 12 shows a block diagrammatic representation of the electronics subsystem included within the instrument 10. By way of introduction, the electronics subsystem operates under the control of a CPU board 200 upon which is included a microprocessor and random access memory (RAM) for storing measurement data. The CPU board 200 also includes a plurality of timing circuits, as well as an analog to digital converter (ADC) for processing the signals produced by various optical and mechanical sensing elements. A system control program is stored on an EPROM software card 205, shown in phantom in FIG. 3, accessible through insertion slot 19 (FIG. 3). Although the instrument 10 is designed to operate as a stand-alone diagnostic device, it may be connected to a host computer through a standard serial interface 210.

As already described, the lamp 110 is modulated by the 10 Khz driver and further chopped or switched at 32 Hz to produce periodic ON and OFF intervals. Referring again to FIG. 12, during each ON interval the CPU board 200 receives an analog signal from a signal preamplifier 215 indicative of the fluorescent intensity emitted by the sample. In like manner during each OFF interval a reference signal proportional to sample illumination intensity is produced by reference preamplifier 220 and received by CPU board 200. The CPU board 200 also receives, over a first set of bit lines B1, digital signals from a set of cartridge detection sensors arrayed on carriage 50. Digital signals carried by second and third sets of bit lines B2 and B3, connected to cartridge heater plate sensors and ambient temperature sensors, respectively, are also provided to CPU board 200. In addition, the X-axis and Y-axis positions of the optics and cartridge carriages are respectively conveyed to the CPU board via a fourth and fifth set of bit lines B4 and B5. The digital output produced by sensors within bar code reader 80 is transmitted to the CPU board 200 over a sixth set of bit lines B6, while a seventh set of bit lines B7 are used to control optical emission from the bar code illuminator such as a light emitting diode (LED).

As is indicated by FIG. 12, user command information is provided to the CPU board 200 from the keypad 12, with system status and data being communicated to the user from the CPU board 200 through the LCD display 14 and printer 15. The electronics subsystem further includes an input power module 230 for providing power to the CPU board 200 as well as to a stepping motor driver board. As is indicated by FIGS. 4A–B and 13A–B, the stepping motor driver board 240 provides control signals to a syringe stepper motor used in dispensing controlled amounts of buffer to the cartridge 24, as well as to the X-axis stepper motor 75 and Y-axis stepper motor 62. The syringe 96 delivers about a 250 microliter volume to the cartridge with about less than 0.5% error.

B. Microcontroller and System Memory

Referring to FIG. 13, there is shown a more detailed block diagrammatic representation of selected portions of the electronics subsystem. In a preferred embodiment the CPU board 200 is implemented using a microcontroller, such as the Motorola MC68HC16Z1 Micro Controller including CPU 280. CPU 280 interfaces with an instrument data bus 284 through a bus interface 288. The CPU 280 is programmed to receive various instrument 10 status inputs and processor interrupt signals by way of a set of input pins included within the data bus 284. This status information will generally indicate, for example, whether the mechanical micro-switch 79 mounted on heater plate 54 has detected the presence a sample cartridge, and whether optical sensors mounted adjacent carriages 50 and 70 have determined that the optics and cartridge carriages are located in a "HOME" or initialized position. The CPU 280 will also be programmed to recognize the digital waveform produced by the bar code reader 80 as a status input. The foregoing status information is relayed to the CPU 280 through a first input buffer 308.

Figure 13A:
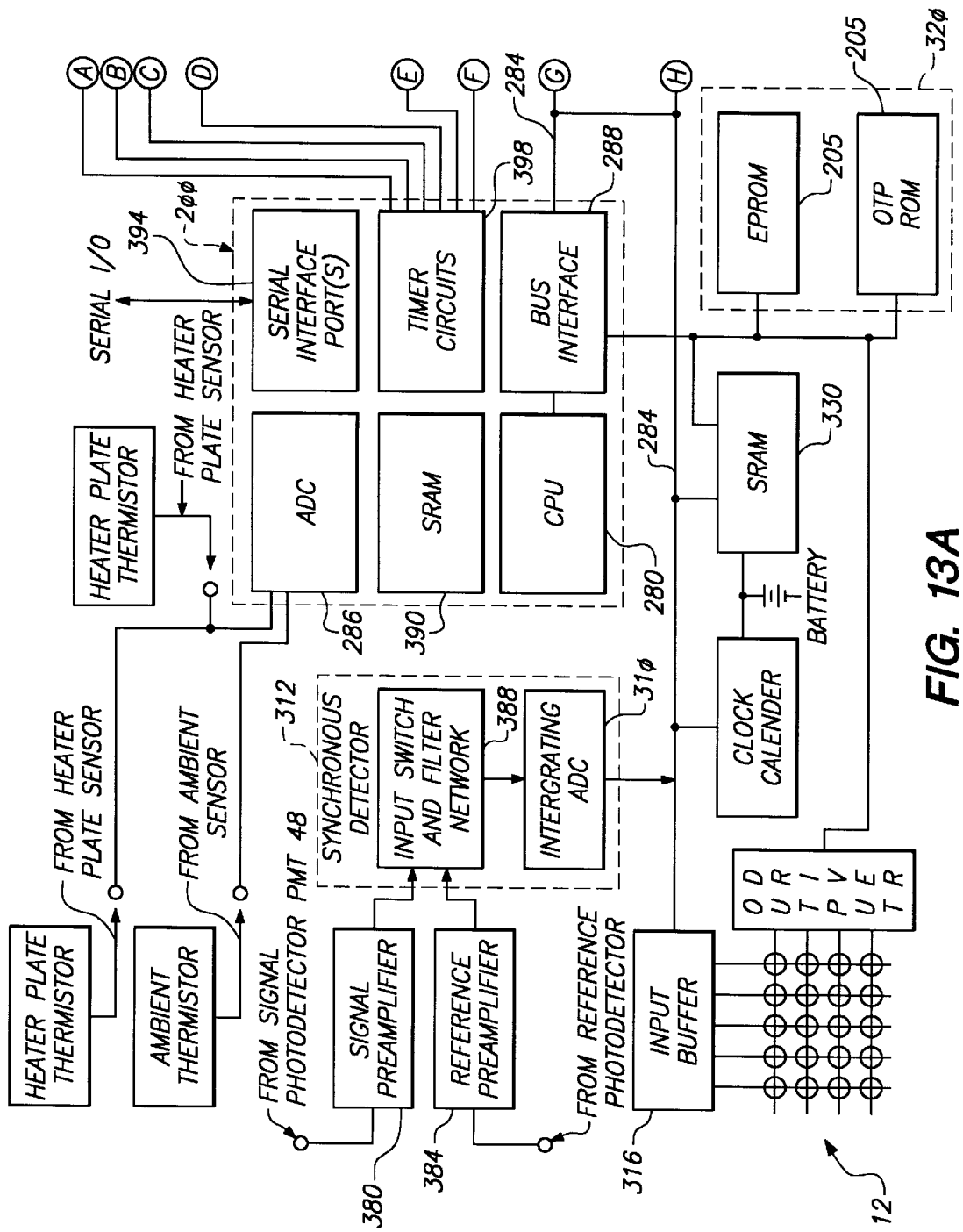
FIGS. 13A–B provide a more detailed functional block diagrammatic representation of selected portions of the electronics subsystem shown in FIG. 12.
Figure 13B:
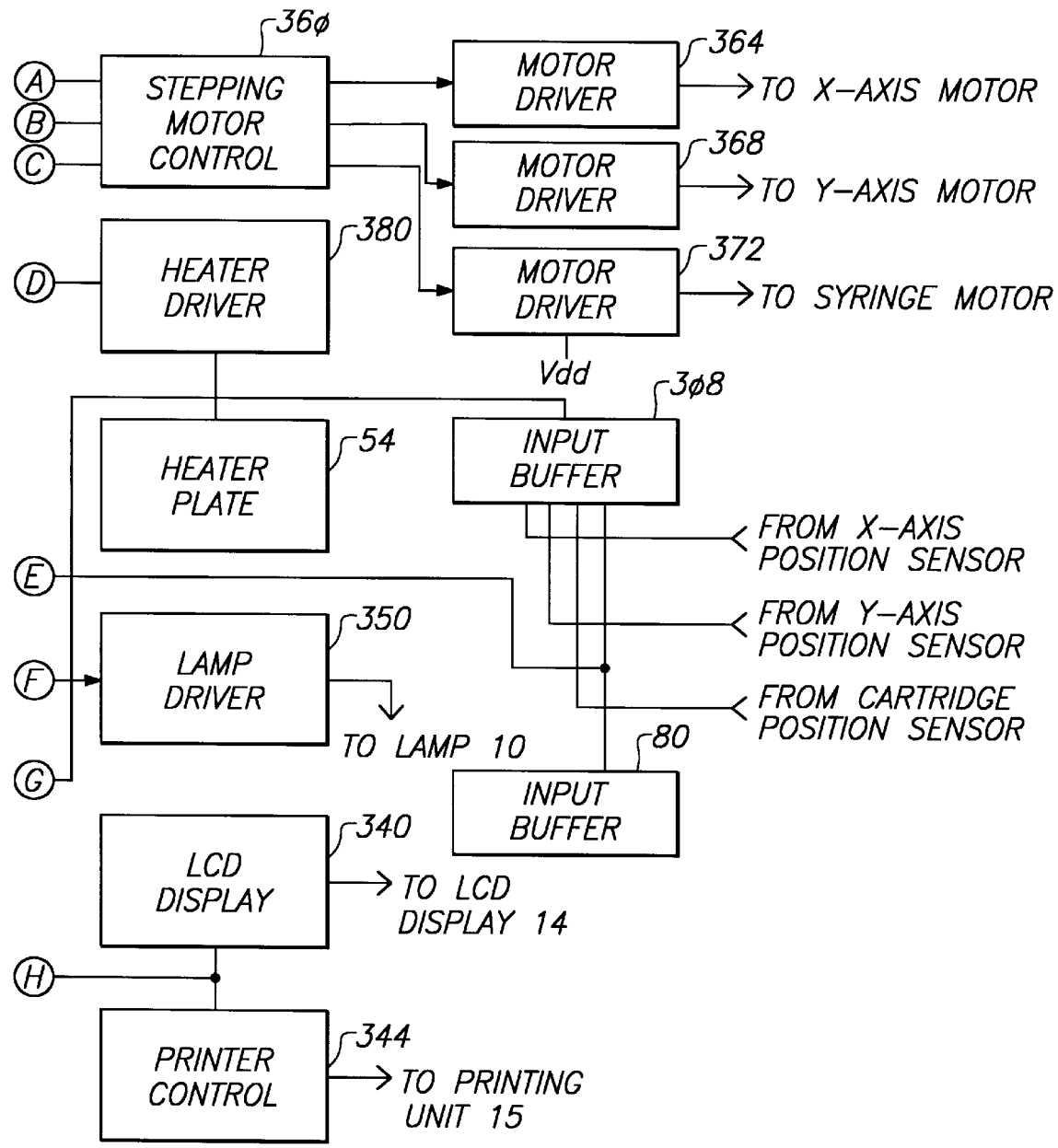

As is indicated by FIGS. 13A–B, an analog signal indicative of the temperature of the sample is received by ADC 288 in the microcontroller from a thermistor sensor 190 affixed to the heater plate 54 (FIG. 4A). The microcontroller is also disposed to receive an analog signal having a magnitude proportional to ambient temperature from a thermistor sensor mounted within the instrument 10 (not shown), as well as to monitor the set of voltages (e.g., ±5V, +24V) produced by the power supply 230.

The CPU 280 is preferably be further programmed to perform a number of chip select functions in response to commands entered via the keypad 12, which is operatively connected to data bus 284 through input buffer 316. These functions are also carried out in response to instructions issued during execution of analysis programs stored in programmable memory 320. As is shown in FIG. 13A, programmable memory 320 includes an erasable programmable read-only memory (EPROM) card 205 when inserted by a user. A One-time Programmable ROM card (OTP ROM) could also be used under appropriate circumstances and at lower cost. Information is transferred from memory 320 to CPU 280 is facilitated by execution of a chip select function within bus interface network 288. In like manner other chip select functions are used to transfer data between CPU 280 and static random access memory (SRAM) 330, to enable CPU 280 to receive information input from keypad 12, and to allow CPU 280 to output information to an LCD controller 340 and to printer control electronics 344.

The CPU 280 will also typically be programmed to execute a plurality of different hardware output functions during the course of providing control information to various electronic device drivers. In particular, output pins within bus interface 288 are actuated by select functions when the DSP 280 provides control signals to:

(i) an lamp driver 350 operative to provide the light excitation signal E to the lamp 110;

(ii) a stepping motor control network 360 utilized to control X-axis, Y-axis, and syringe stepper motor drivers 364, 368 and 372; and (iii) a heater driver 380 operatively connected to resistive heating elements affixed to heater plate 54.

Referring to FIG. 3A, the CPU board 200 is further seen to include an SRAM module 390, serial interface ports 394, and various timer circuits 398. In an exemplary embodiment the timer circuits 398 provide modulated timing waveforms to the lamp driver 350 to selectively turn the lamp ON and OFF periodically, bar code reader 80, and stepping motor control network 360.

C. Detection Electronics

Figure 14:
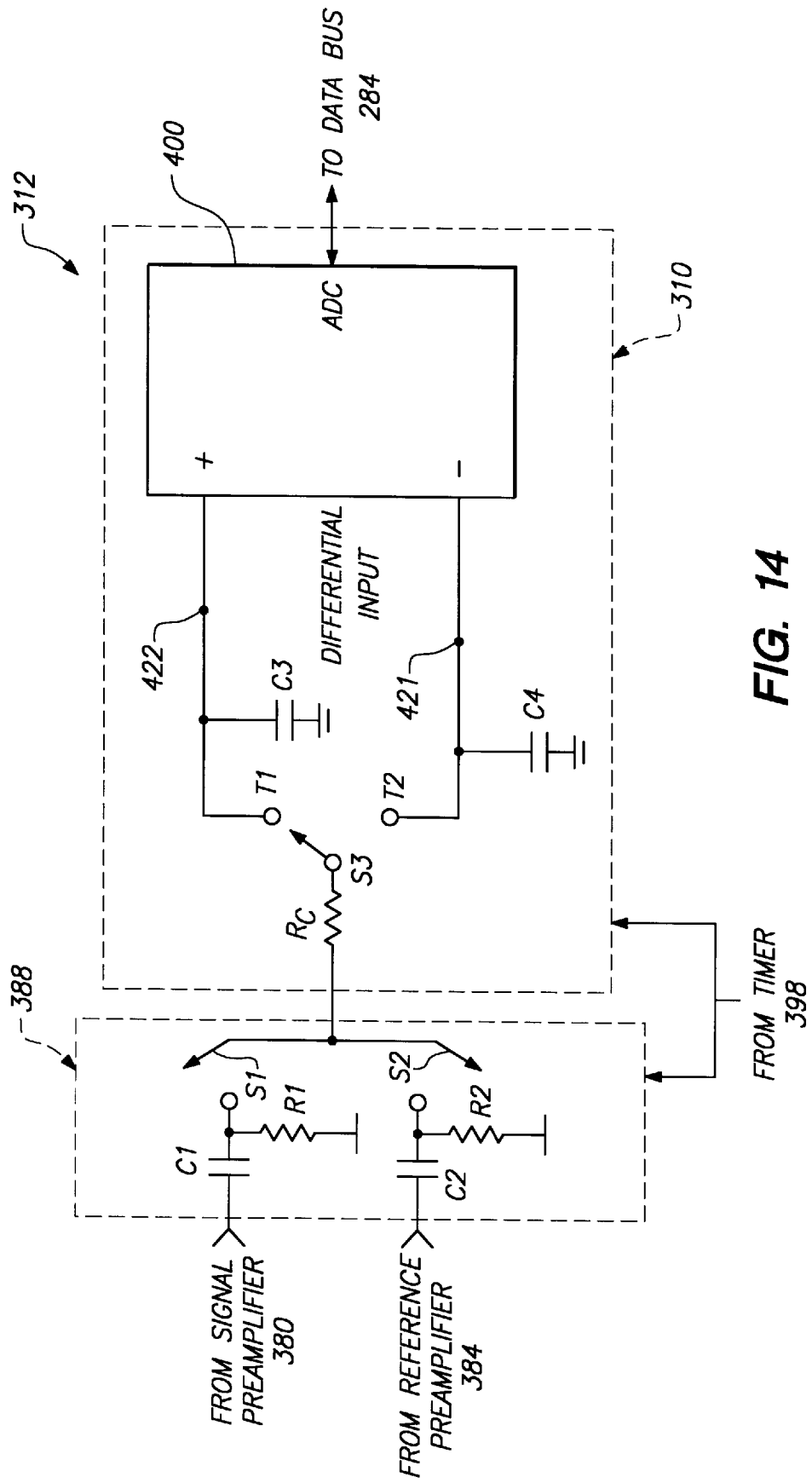
FIG. 14 is a schematic diagram showing an embodiment of a switched filter network and integrating analog to digital converter included within the detector network.

As is indicated by FIGS. 3A–B and 14, an analog signal indicative of fluorescent emission intensity is received by preamplifier 380 from PMT 98 (FIGS. 4A–B). Preamplifier 380 converts the input photo current to a signal detection voltage in accordance with a predefined conversion factor (e.g., about 10 mV/$\mu$A). In an exemplary embodiment the conversion gain of preamplifier 380 is approximately 10 mV/$\mu$A in the passband (up to 3-dB cutoff frequency on the order of 7 kHz).

The signal and reference detection voltages generated by the preamplifier 380 are provided to a switched filter network 388 within synchronous detector 312. The filter network 388 operates, in response to timing control signals from a timer circuit 310, to alternately filter the signal and reference detection voltages. The filtered detection voltages are then alternately supplied to the IADC 310.

FIG. 14 provides a more detailed representation of the switched filter network 388 and the integrating analog to digital converter 310 included within the synchronous detector 312. The lamp 110 that produces the florescent excitation is modulated by a 32 Hz square wave generated by a square wave signal generator means. The circuit depicted in FIG. 14 is used to demodulate the signal and reference channels at this same 32 Hz frequency. Each square wave cycle consists of two equal periods: ON and OFF; where during the ON period, the lamp is on, and during the OFF period the lamp is off.

During the On period, analog switch S1 is closed thus charging capacitor C1 through resistor R1 to the signal level. During the ON period, switch S2 is closed thus charging capacitor C2 through resistor R2 to the zero, or baseline level.

The RC time constant τ of R1, C1 and R2, C2 is chosen to be several times the 1/32-Hz square wave frequency so that a nearly DC component is passed into an analog multiplexer shown as a set of switches in FIG. 14. An identical circuit exists for the reference channel, and either the signal channel or reference channel may be selected for digitization by the analog-to-digital converter (ADC) 400 through the multiplexer. The multiplexer passes both signal and baseline levels into the ADC 400. The ADC has a differential input so the baseline is thus effectively subtracted from the signal, thereby eliminating DC drifts from the system.

In the preferred embodiment the ADC 400 comprises an 18-bit analog to digital converter. For example, the MAXIM Model MAX132 may be used. One of the parallel output ports of the ADC 400 will generally be configured to select between its inverting 421 and non-inverting 422 input ports in response to timing signals placed on data bus 284 by the microcontroller through the bus interface 288. Upon completion of the conversion operation performed during a particular ON or OFF interval the ADC 400 produces an interrupt signal which is received by the microcontroller by way of the data bus 284.

D. Bar Code Electronics

Figure 15:
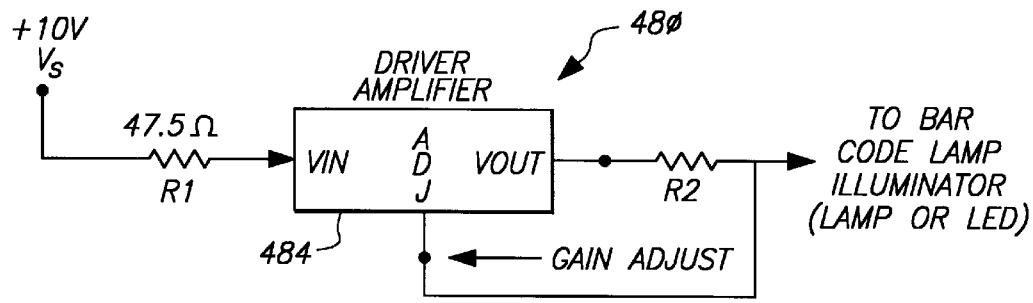
FIG. 15 shows a schematic representation of bar code driver electronics used to energize the bar code emitter within a bar code reader utilized an embodiment of the instrument.

FIG. 15 shows a schematic representation of the bar code driver electronics 480 used to energize the LED emitter within the bar code reader 80. Driver electronics 480 is seen to include a driver amplifier 484 having an input port $V_{IN}$ connected to a supply voltage of +10V through a resistor R1 (47.5 ohms). The amplifier 484 may be realized using, for example, a voltage regulator, Part No. LM317, manufactured by National Semiconductor. The current to the bar code LED is controlled by the value of a resistor R2 connected between output port $V_{OUT}$ and gain adjustment port ADJ.

Figure 16:
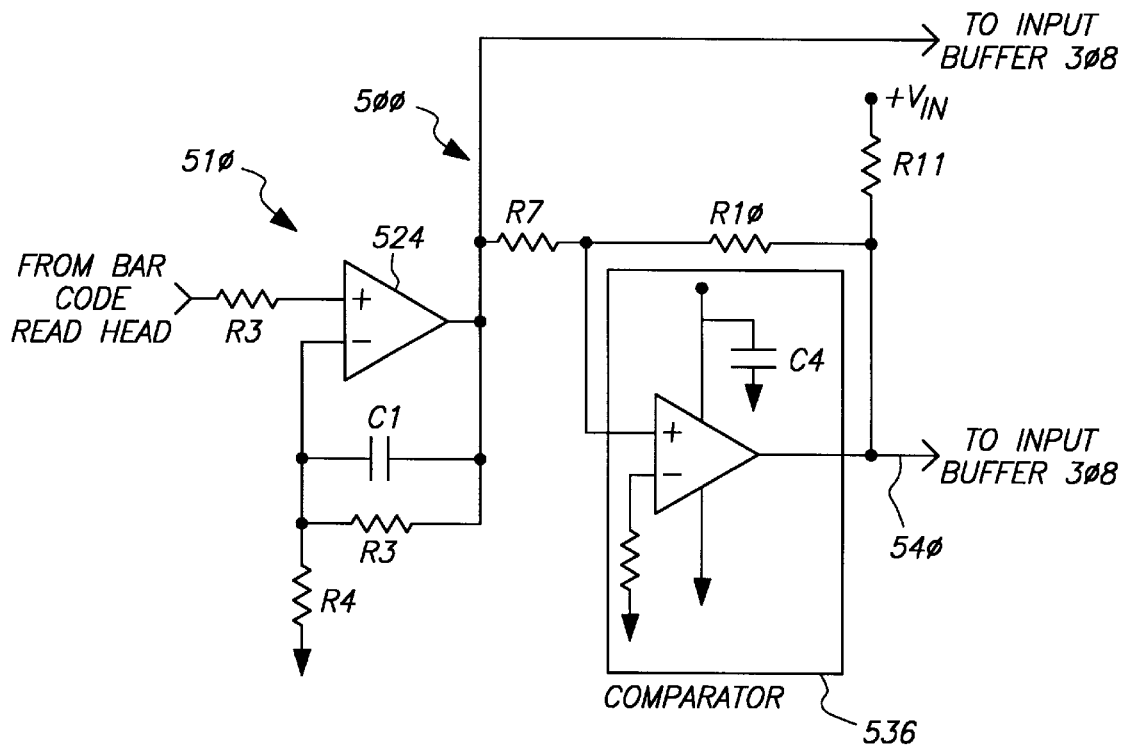
FIG. 16 provides a schematic representation of bar code detection electronics operative to process an analog detection signal generated by a bar code reader read head.
Figure 17:
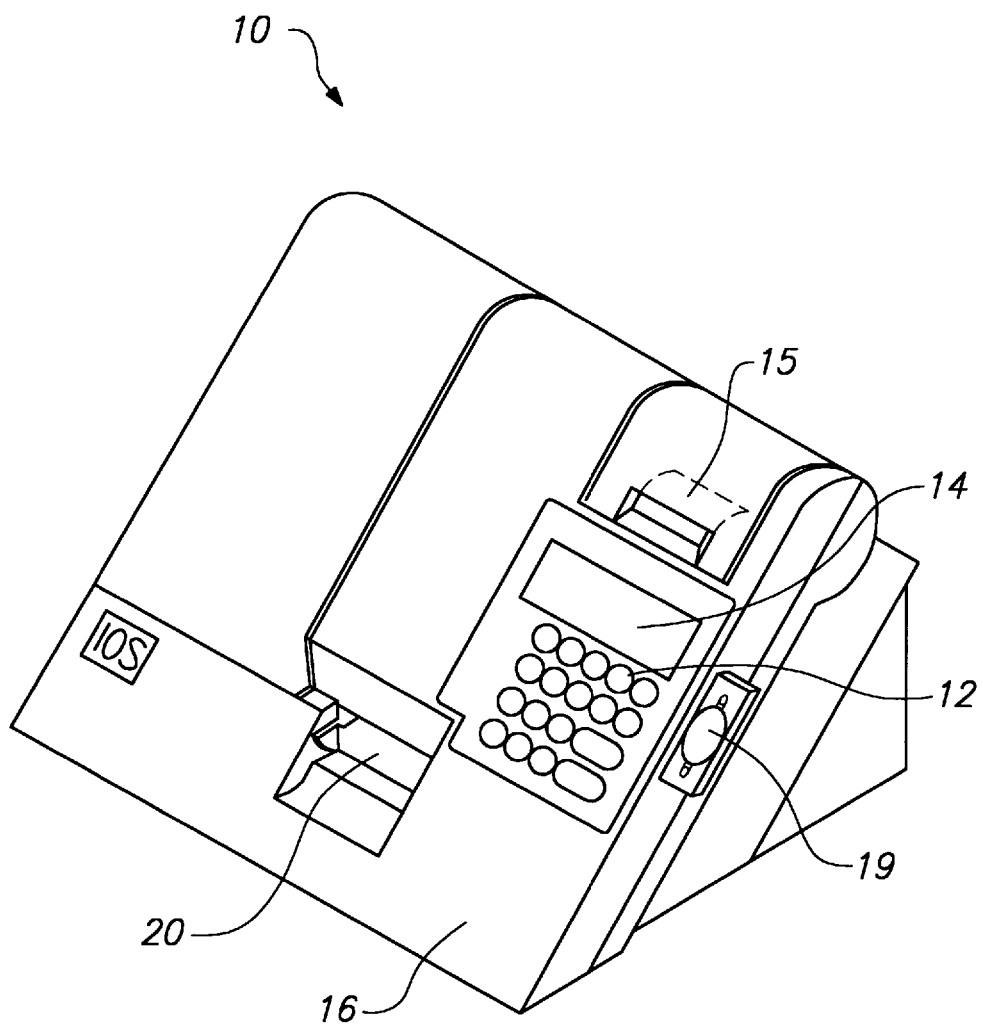
FIG. 17 is a diagrammatic illustration of exterior features of an embodiment of the inventive In-Office System (IOS™) instrument.
Figure 18:
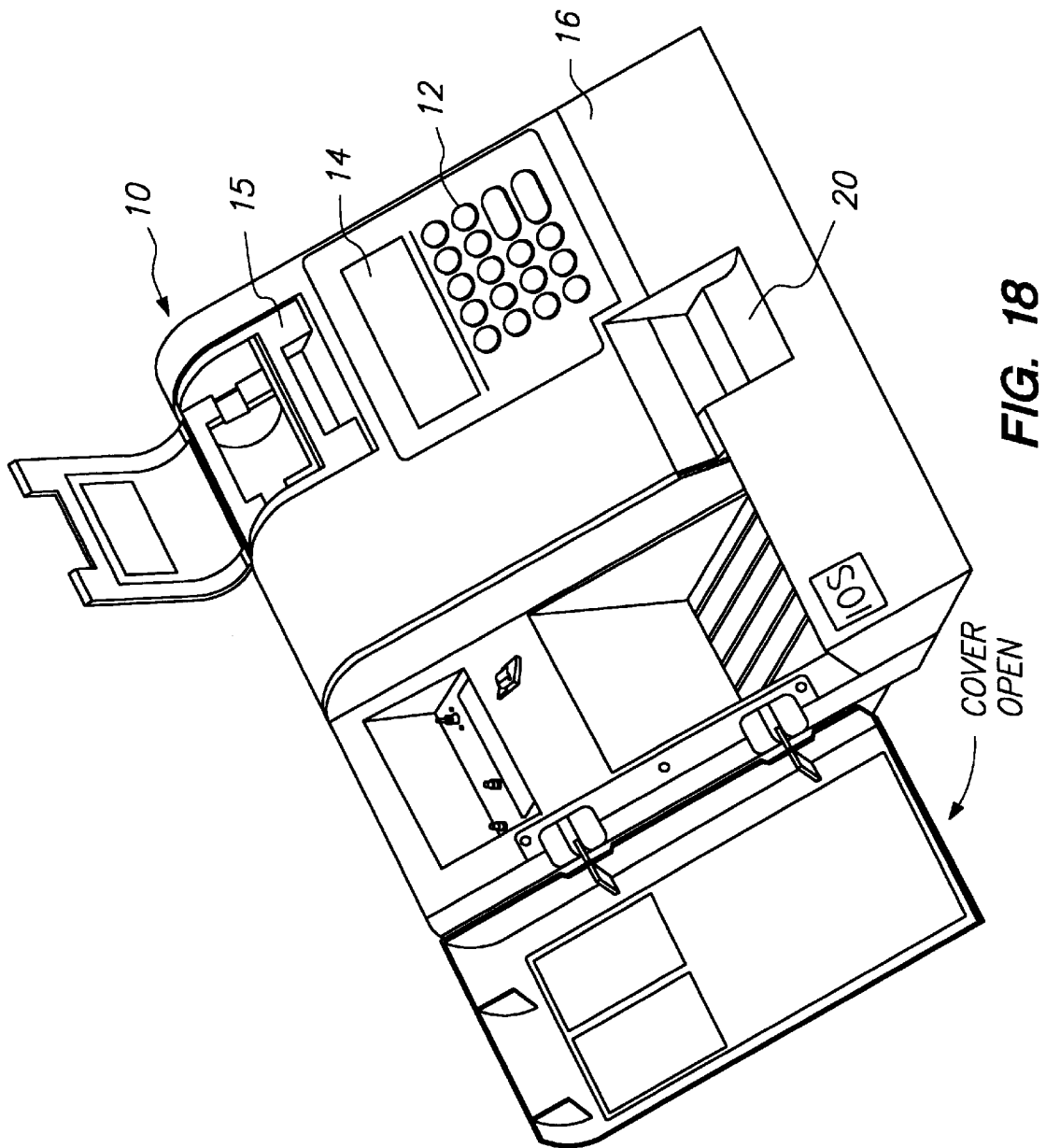
FIG. 18 is a diagrammatic illustration of the instrument in FIG. 17 but showing open doors and panels that reveal internal compartments for buffer supply reservoir, buffer waste reservoir, and printer paper.
Figure 19:
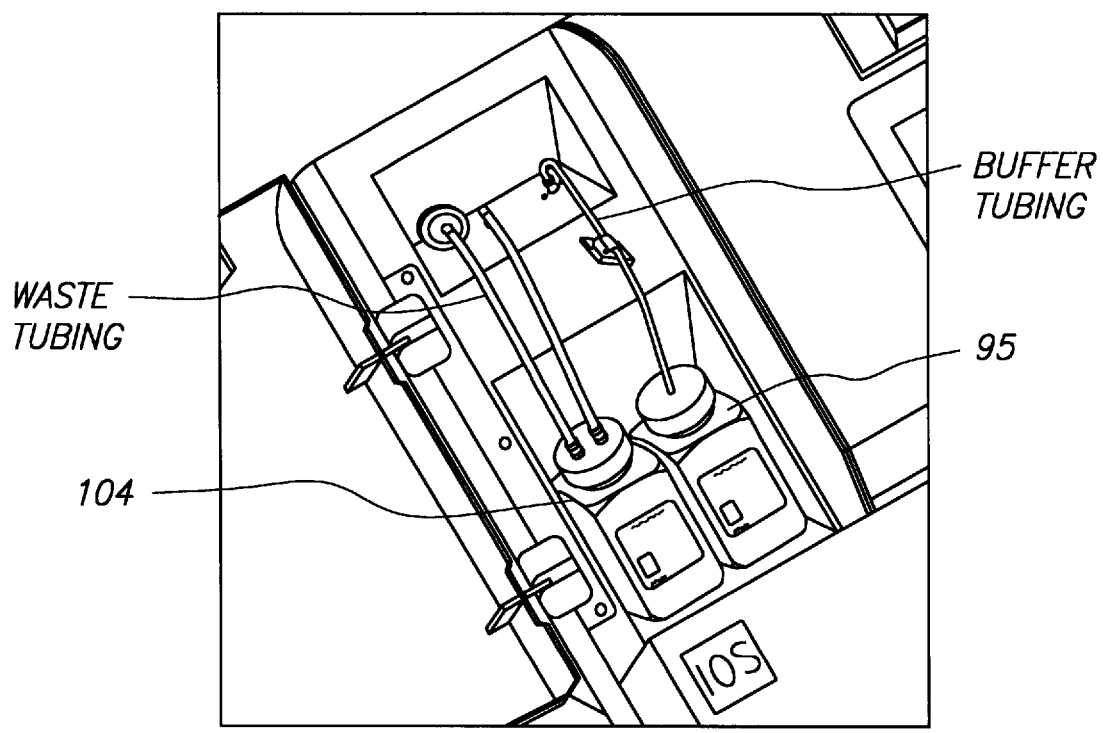
FIG. 19 is an illustration of a portion of the instrument in FIG. 17 showing the installation of buffer and waste bottles and the tubing, pumps, and fittings that provide connection means between the bottles and the interior of the instrument.
Figure 20:
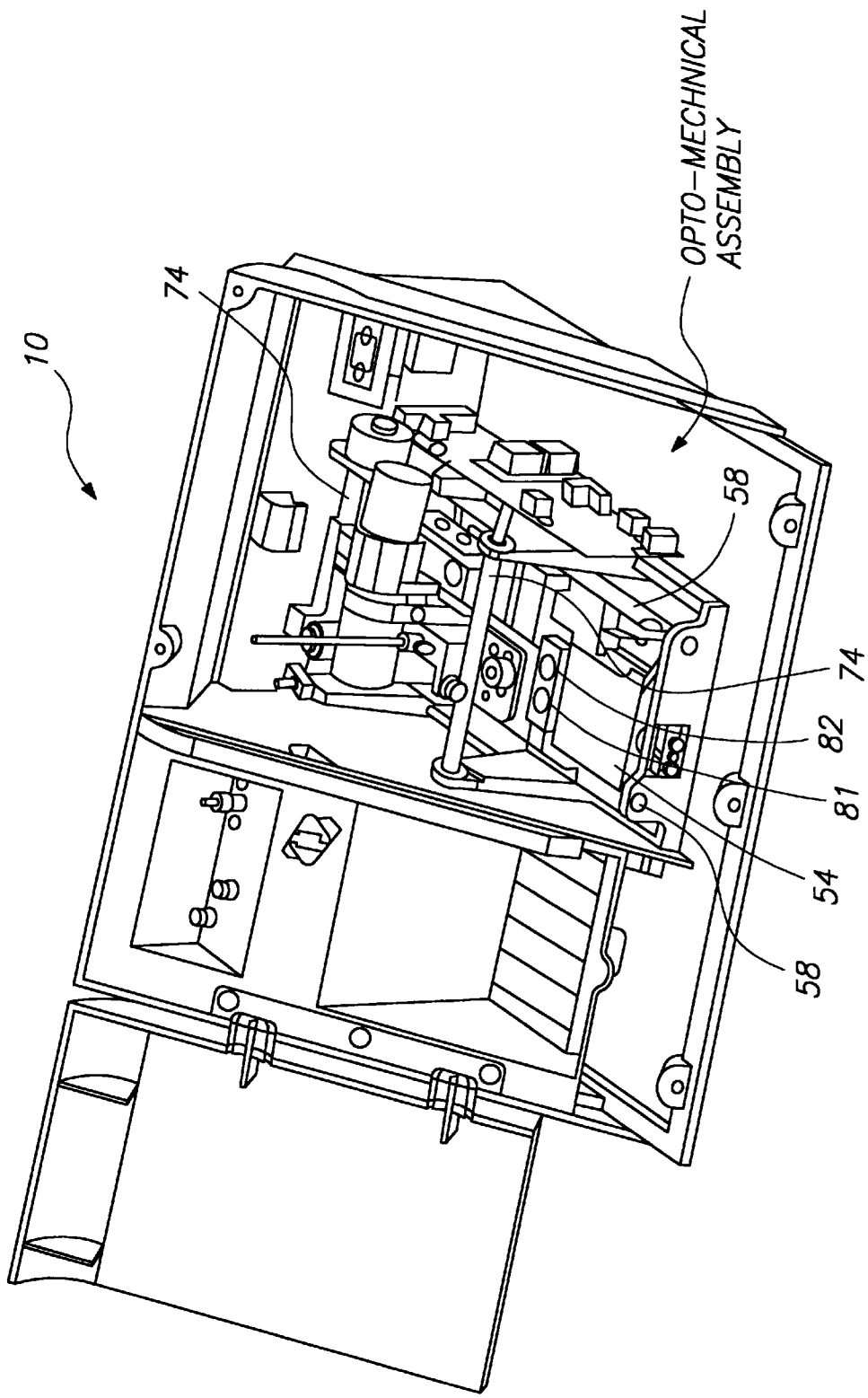
FIG. 20 is an interior view of a preferred embodiment of the inventive instrument showing the major opto-mechanical assemblies.
Figure 21:
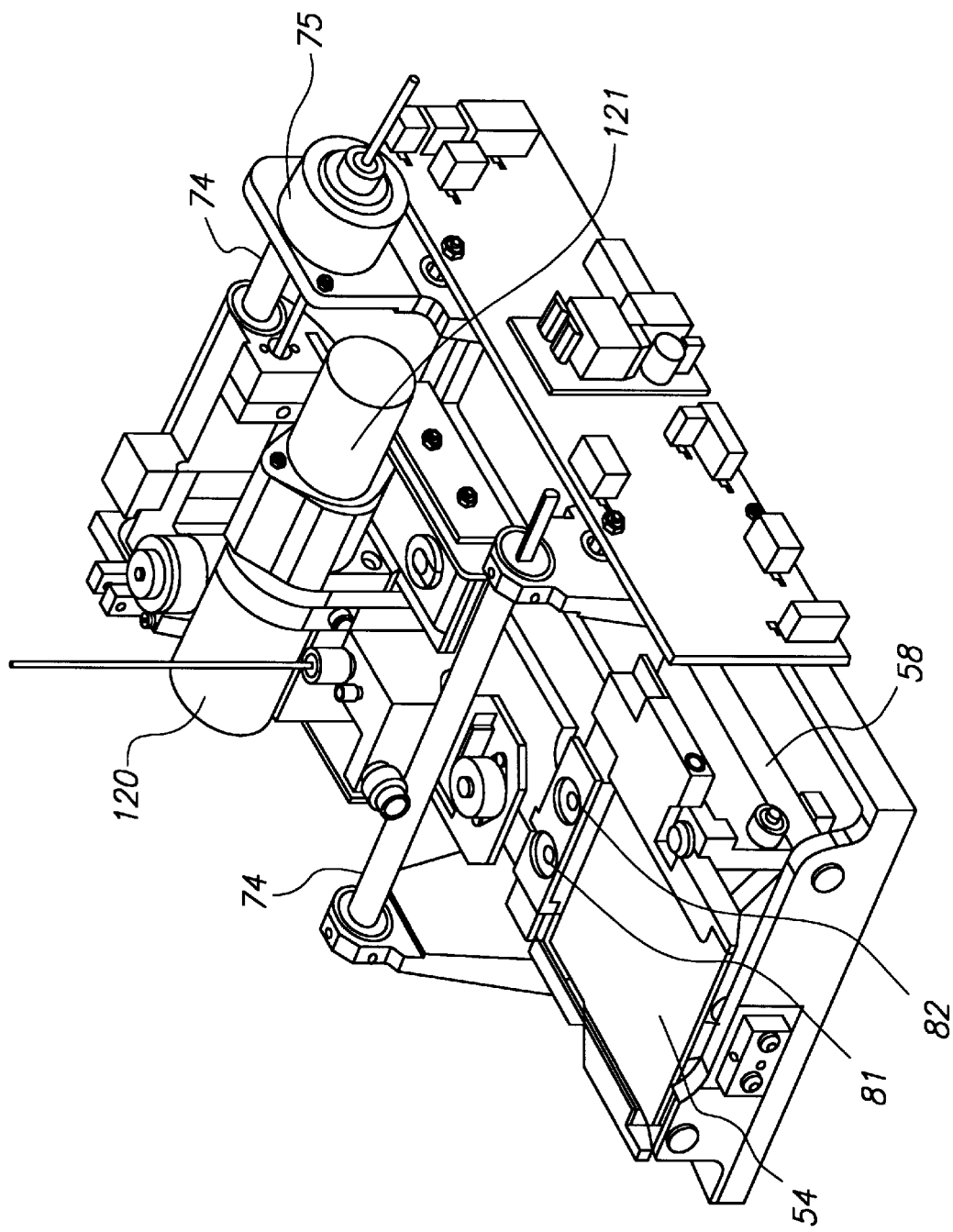
FIG. 21 is a schematic diagram of the opto-mechanical assembly shown in FIG. 20.
Figure 22:
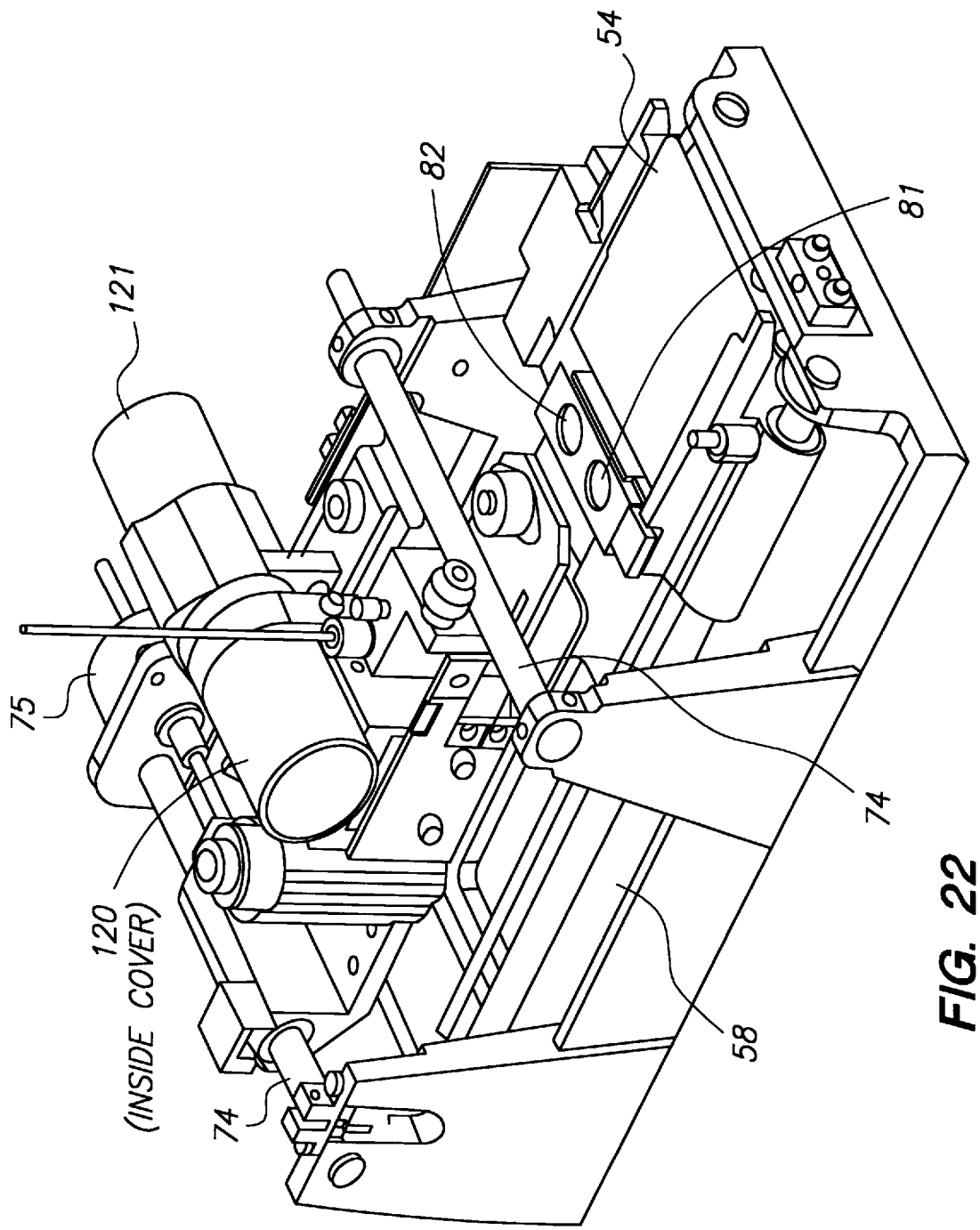
FIG. 22 is an alternative schematic view of the opto-mechanical assembly in FIG. 21.
Figure 23:
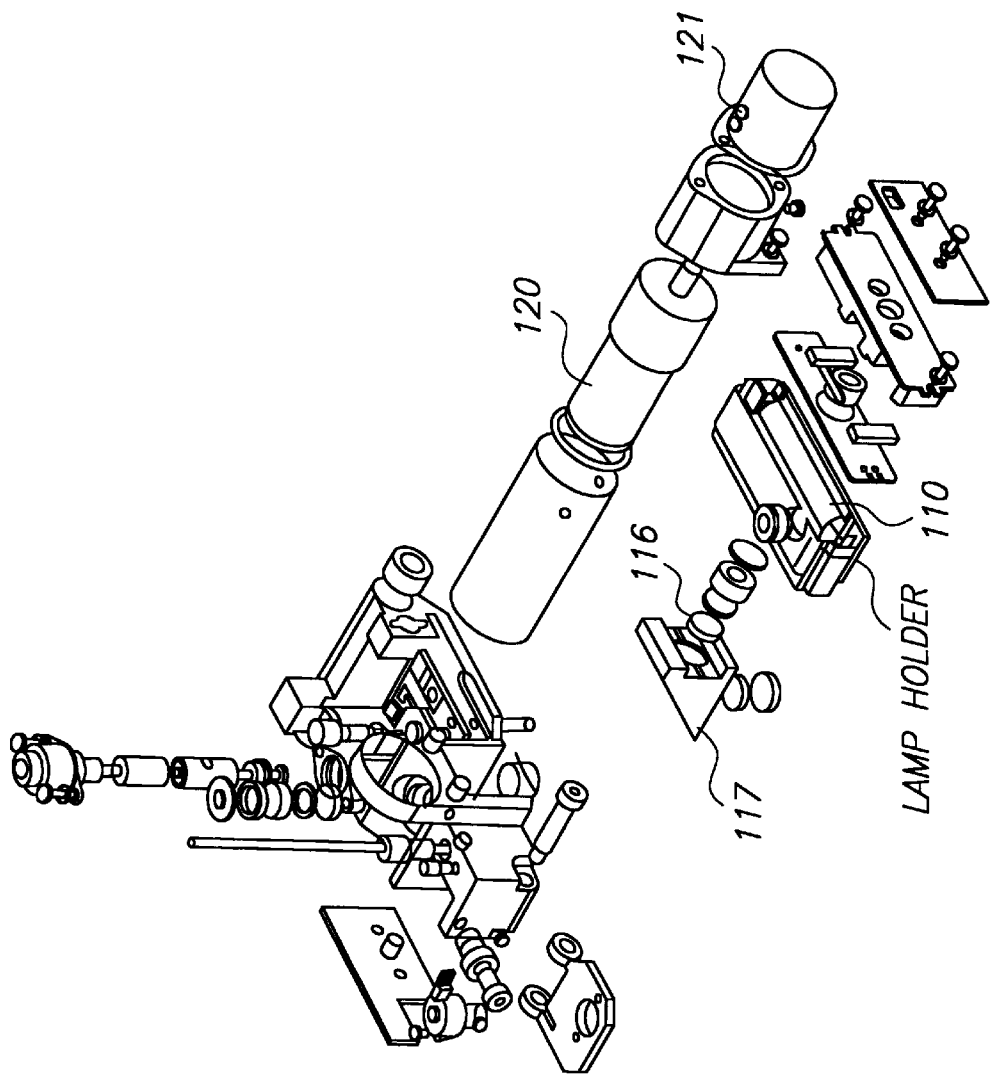
FIG. 23 is an exploded partial assembly drawing of major optical and mechanical components of the instrument shown in FIG. 21.

Referring to FIG. 16, there is shown a schematic representation of bar code detection electronics 500 operative to process the analog detection signal generated by the bar code read head. The bar code detection electronics 500 are designed to compensate for the variation in output signal intensity produced by different commercially available bar code readers, which generally each include an LED emitter and bar code read head. In this way a particular bar code reader may be replaced by one having differing output characteristics without adjustment, i.e., "tuning", of the components in bar code detection electronics 500. This compensating feature of detection electronics 500 also allows bar code identifying labels of differing reflectance to be utilized in the absence of a corresponding modification of component values.

As is indicated by FIG. 16, a voltage is produced by the bar code read head and preamplifier and fed to amplifier 510. The amplifier 510 also serves as a low pass filter having a cutoff frequency of approximately 16 Khz, the frequency at which the light and dark regions of the bar code identifying labels alternately appear within the field of view of the bar code reader.

The output from amplifier 510 is fed into one of the ADC 288 input channels of the microcontroller 200. This allows the black and while levels on a particular bar code label to be measured, by moving the cartridge with the attached bar code to a special black and while level calibration points on the label and taking their respective reflectance readings. Once these black and while levels are established, the trip threshold level of comparator 536 is set to on-half the voltage levels measured, or $V_{THRES}=(V_{BLACK}+V_{WHITE})/2$. Then, as an actual bar-code is scanned, the comparator 536 is set to trip at the optimum level for any particular bar-code label. This provides means for compensating for production variation is bar code surface characteristics, bar code scanner characteristics, and the like.

Referring again to FIG. 16, the detection voltage provided by amplifier 510 is applied to the non-inverting terminal of the comparator 536 through resistor R7. When the detection voltage exceeds the comparator threshold voltage the output terminal 540 of comparator 536 is driven to a logical HIGH which corresponds to the reading of a white region of the bar code label being scanned. Similarly, the reading of a dark region of the bar code label causes the detection voltage to fall below the comparator threshold voltage, which results in the voltage at the output terminal 540 of comparator 536 being driven to a logical LOW. The component values used in a preferred implementation of the bar code detection electronics 500 are set forth below in the following table.

| Component Values for Bar Code Electronics | |
|---|---|
| Component | Value |
| R3 | 10kΩ |
| R4 | 1kΩ |
| R5 | 10kΩ |
| R7 | 22.1kΩ |
| R10 | 10MΩ |
| R11 | 10kΩ |
| C1 | 1000pF |

A particul embodiment of the inventive IOS system is illustrated in FIGS. 17–23. These figures present the same opto-mechanical components already shown and described (particularly with respect to FIGS. 1–3, 4A–B, and 7A–B). These additional figures merely illustrate a preferred embodiment of the invention in terms of its preferred mechanical and optical organization in a housing having limited dimensions. Reference numbers in these figures correspond to those already described relative to FIGS. 1–16. In the preferred embodiment of the invention, many of the optical components are standard commercial components. The following commercial components have been implemented in the preferred embodiment of the inventive IOS instrument 10:

| ITEM | Commercial Item | Commercial Source |
|---|---|---|
| Lamp 110 | BF959-WV1 Ultraviolet miniature florescent lamp having peak emission at 365 nm. | JKL Components 13343 Paxton Street Pacoima, California 91331 |
| Reference Filter 113 Excitation Filter 114 | P10-365A | Corion Corporation (508)429-5065 |
| Emission Filter 118 | P10-440A | Corion Corporation |

-continued

| ITEM | Commercial Item | Commercial Source |
| --- | --- | --- |
| | | 73 Jefrey Avenue |
| | | Holliston, MA 01746 |
| | | (508)429-5065 |
| Photomultiplier Tube (PMT) 120 | Hamamatsu 931B | Hamamatsu |
| | | 420 South Avenue |
| | | Middlesex, N.J. 08846 |
| PMT Power Supply 121 | Hamamatsu HC123-01 | Hamamatsu |
| | | 420 South Avenue |
| | | Middlesex, N.J. 08846 |
| Cartridge Lens 116 | KBX022 | Newport |
| | 12.7 mm Diameter Bi- | P.O. Box 19607 |
| | Convex Optical Glass Lens | Irvine, CA 92713-9607 |
| | Focal Length = 12.7 mm | (714)-863-3144 |
| Reference Lens 112 | KPX040 | Newport |
| Excitation Lens 111 | 12.7 mm Diameter Plan- | P.O. Box 19607 |
| | Convex Optical Glass Lens | Irvine, CA 92713-9607 |
| | Focal Length = 19.0 mm | (714)863-3144 |

IV. SYSTEM CONTROL PROGRAM

Figure 24:
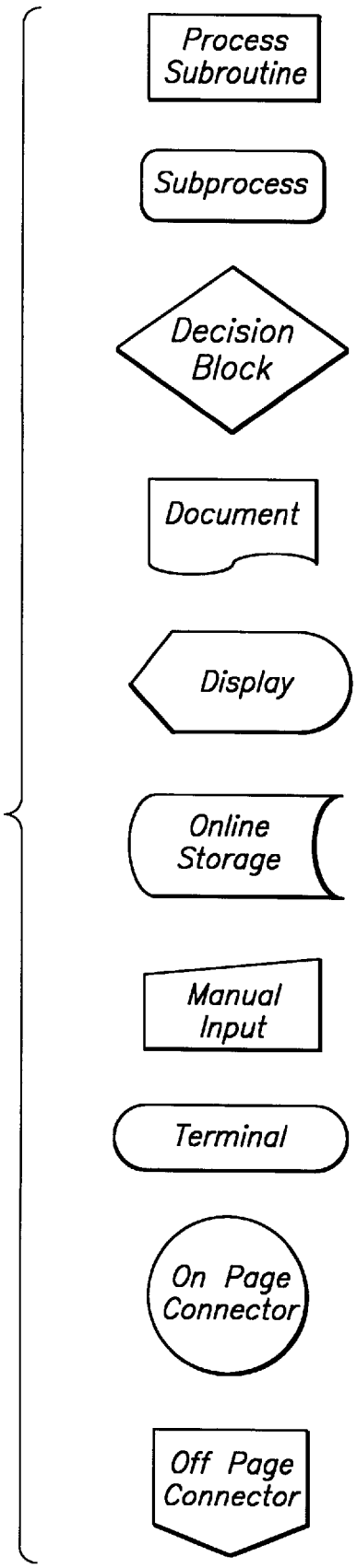
FIG. 24 provides a flow-chart convention legend for identifying a set of symbols incorporated within the flow-charts of FIGS. 26–28.

Operation of the instrument 10 is governed in the preferred embodiment by a control program stored within erasable programmable read-only memory (EPROM) 322 (FIGS. 3 and 135). In FIG. 24 there is depicted a legend for identifying a set of symbols incorporated within flowcharts (FIGS. 25, 26, and 27A–C representative of the operational sequences executed during the performance of various functions within the instrument 10.

Referring to FIG. 24, the symbol labeled "Subroutine" refers to a low-level software subroutine dedicated to carrying out a specific task (e.g., controlling a particular instrument component). Similarly, "Subprocess" refers to a higher level control procedure in which calls are made to various subroutines. The symbol associated with the label "Decision Block" indicates a branching or decision point, while the identifier corresponding to "Document"relates to the receipt or production of a document, report or form. "Online Storage" indicates transfer of data to or from a particular memory location, while "Manual Input" refers to information provided to the instrument by a user through an input device (e.g., keypad 12). The symbols labeled "Terminal", "On Page Conn.", and "Off Page Connector" respectively indicate:

(i) the end of an operational sequence, (ii) a connection between various steps within a particular flowchart, and (iii) transition between operational sequences included within one or more flowcharts.

Figure 25:
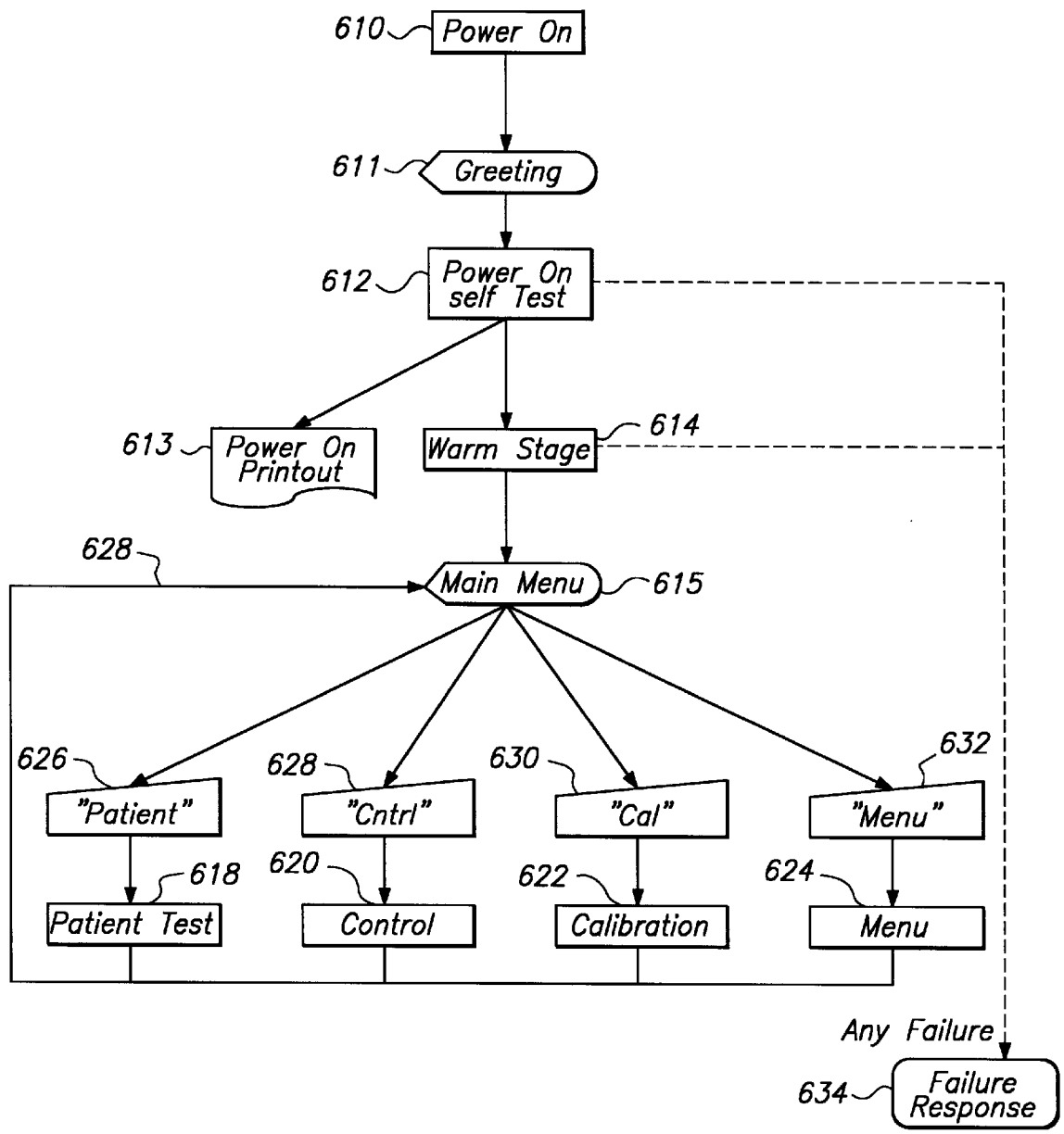
FIG. 25 is a diagrammatic flow-chart depicting an embodiment of the operational sequence corresponding to system initialization and to the generation of a main menu for display to a user of the instrument.

Referring to FIG. 25, there is depicted the operational sequence corresponding to system initialization and to the generation of a main menu for display to a user via LCD display 14. Upon system Power ON (step 610) a greeting (step 611) is generated by LCD display 14 and an internal Self Test routine (step 612) is performed. During the self test routine (step 612), the CPU 280 transmits status requests to the various instrument components. The results of these inquires will preferably be conveyed to an operator through generation of a report (step 613) by printing unit 15. Following Self Test (step 612) the various electrical components included within the instrument 10 are given an opportunity to rise in temperature during a Warm Stage (step 614) upon being energized at system Power ON (step 610). A Main Menu is then presented (step 615) to the operator through the LCD display 14. As is indicated by FIG. 25, the procedures identified as Patient Test, Control, Calibration and Menu (steps 618, 620, 622 and 624) may be selected from the Main Menu by way of the keypad entries Patient, Cntl, Cal and Menu (steps 626, 628, 630 and 632). Upon the occurrence of a system failure during execution of any of the aforementioned procedures, control of the instrument 10 is transferred to a Failure Response routine (step 634). The Failure Response routine operates to inform the user of the failure (if possible) and to take other action to recover from the failure as may be programmed into the instrument. For example, depending upon the failure, the instrument may be directed to discharge the cartridge 24 to the exterior of the instrument, and to inform the user via the display the a falure has been detected. Other failure recovery schemes may also be implemented.

Figure 26:
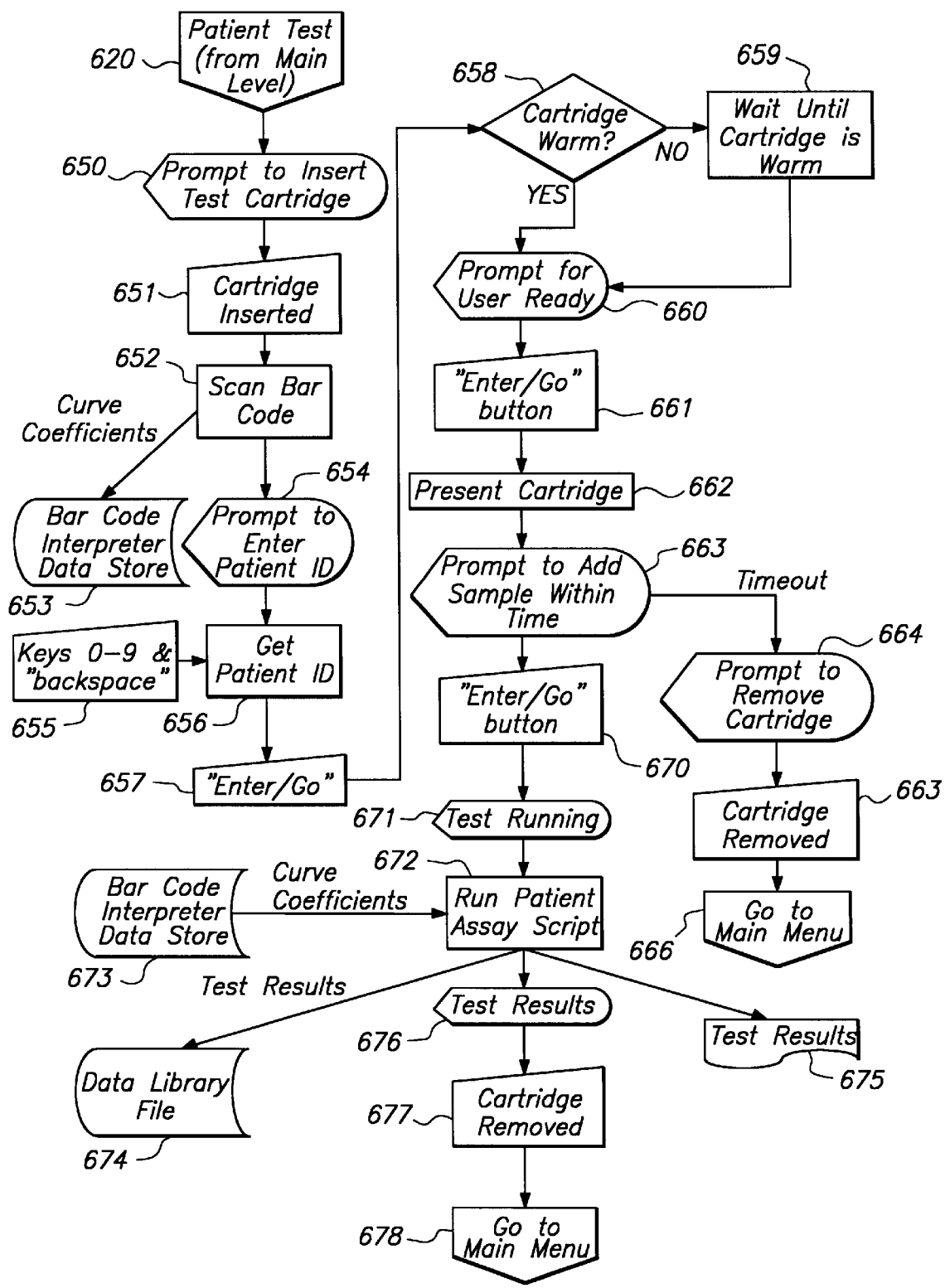
FIG. 26 is a diagrammatic flow-chart depicting the operational sequences included within an exemplary patient test procedure.

FIG. 26 is a flow chart depicting the operational sequences included within the Patient Test procedure (step 620). This procedure is initiated by prompting the user (step 650) to insert a sample cartridge 24 into port 20. Upon such insertion (step 651) of a cartridge 24, the bar code identifying label affixed to the cartridge 24 is scanned (step 652) and coefficients defining a correlation curve associated with the particular sample substance to be analyzed are stored at a predefined memory location (step 653). In an exemplary implementation each curve relates the concentration of a particular substance to a detected change in fluorescent emission from the sample cartridge 24. Those skilled in the art will appreciate that various techniques exist for inducing such a change in fluorescent emission. For example, a fluorescent dye or reagent disposed to bind to an analyte of interest may be introduced into the sample chamber of cartridge 24 as a step in a particular assay procedure.

Turning again to FIG. 26, the operator supplies patient identification information to the instrument 10 through keypad 12 after being prompted via the LCD display 13 (steps 654–656). The procedure 620 is continued by operator entry of an Enter/Go command (step 657), at which point the inserted cartridge is warmed by heater plate 54 (steps 658–660). After reaching a predetermined temperature the cartridge is presented (steps 661–662) to the operator, and a prompt is issued via LCD 14 instructing the operator to add the sample under test to the cartridge 24 (step 663). If this is not done within a predefined timeout period the operator is prompted to remove the cartridge from the instrument and the Main Menu is again displayed (steps 664–666). Assuming that sample is added to the cartridge in a timely manner, control is transferred to a Patient Assay Script procedure and a "Test Running" message is provided to the operator (steps 670–672). The sequence of operations performed during the Assay Script procedure will depend upon the particular test being performed, but will generally include commands which:

(i) control motor and pump drivers 364, 368 and 372;

(ii) control incubation temperature by issuing commands to heater driver 380;

(iii) provide instructions to switch/filter 388 to select between reference and signal detector;

(iv) read data from the integrating ADC 310 into local memory (e.g., into SRAM 390) where the data may be accessed by calls from other control procedures;

(v) initiate one or more scans of the bar code identifying information affixed to the sample cartridge; and (vi) invoke numerical analysis routines operative to, for example, calculate a dose response corresponding to the concentration of an analyte of interest.

Again with reference to FIG. 25, numerical analysis of the data acquired during sample is testing is facilitated by provision of the curve coefficients associated with the sample to the Patient Assay Script (step 673). At the conclusion of such numerical analysis the corresponding test results are stored within a data library file (step 674) and are provided to the operator in the form of a printed report (step 675) and/or via LCD display 114 (step 676). The Patient Test procedure is concluded upon removal of the cartridge from the instrument 10 (step 677), at which time control returns to the Main Menu (step 678).

Figure 27A:
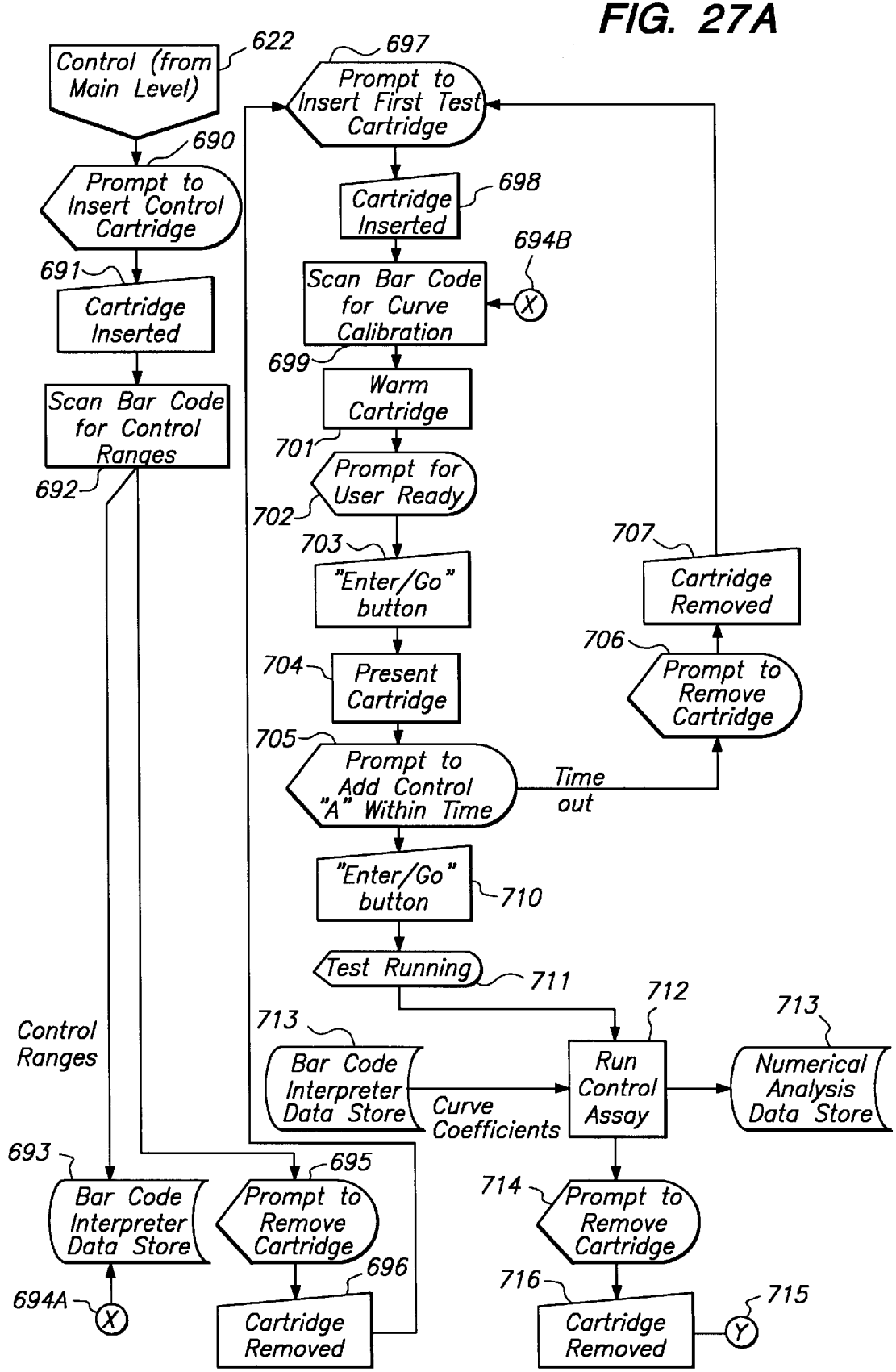
FIG. 27 is a diagrammatic flow-chart depicting the operational sequences included within an exemplary instrument control procedure.
Figure 27B:
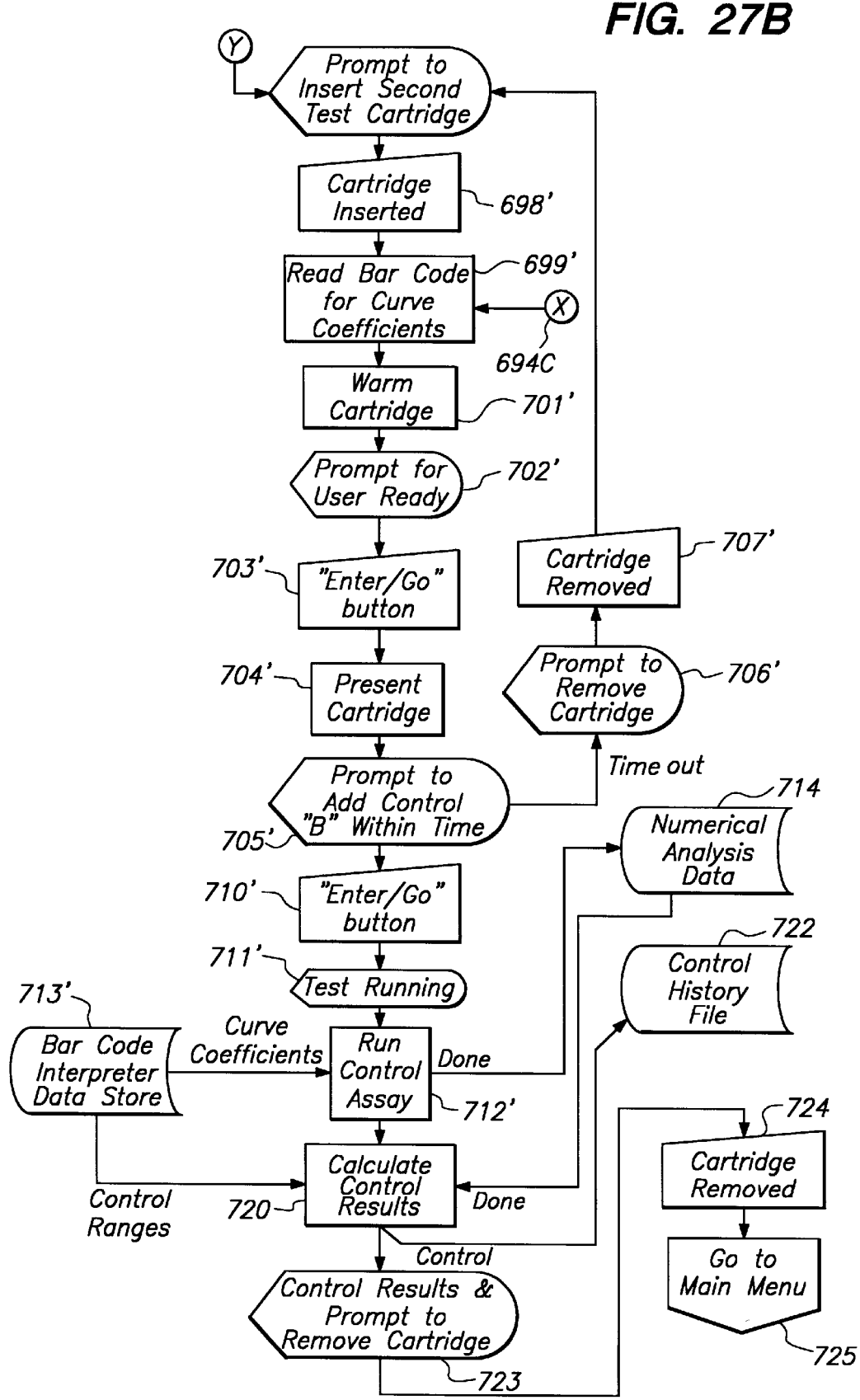
Figure 28:
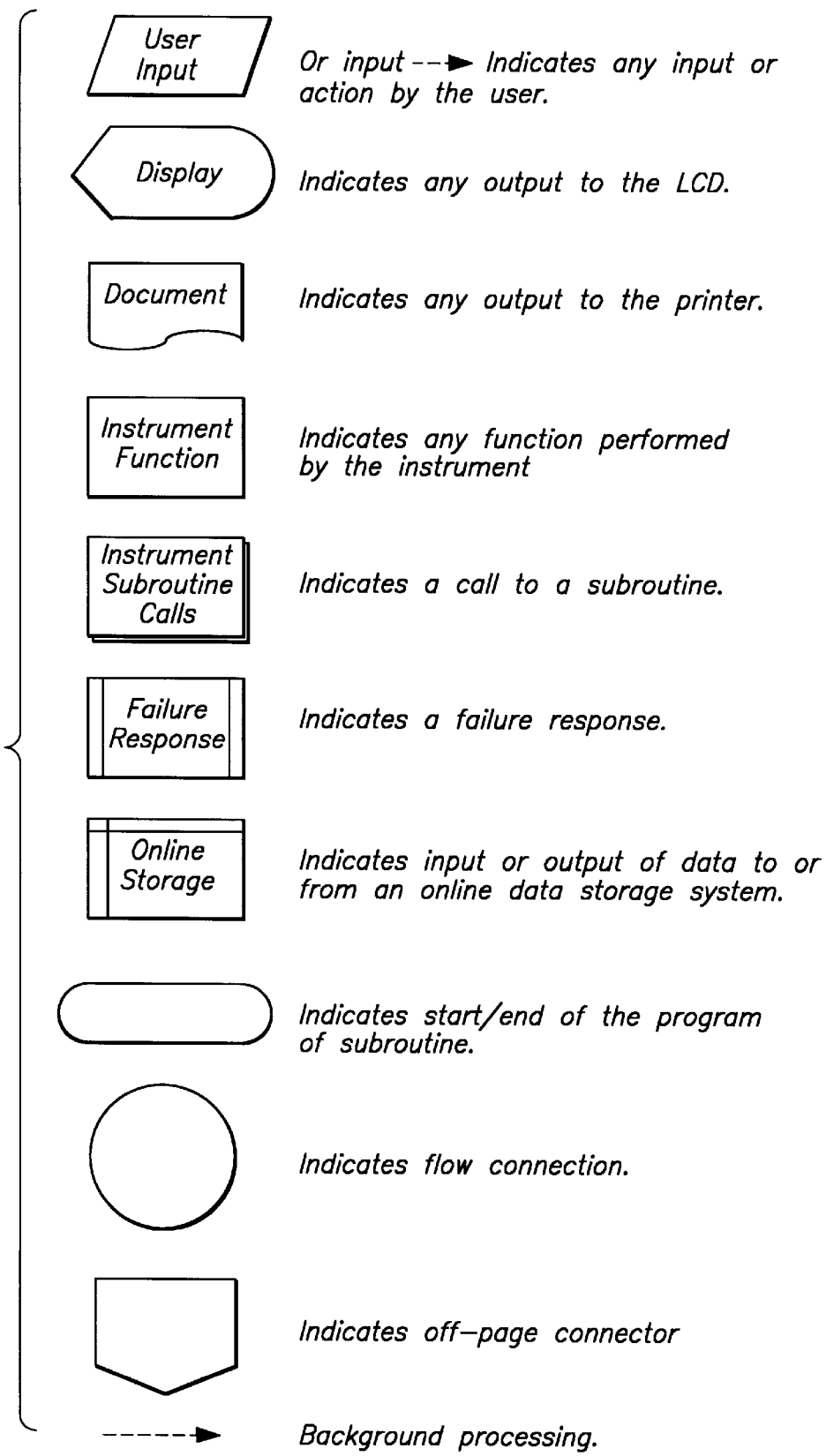
FIG. 28 provides a flow-chart convention legend for identifying a set of symbols incorporated within the flow-charts of FIGS. 29, 30, 31A–C, 32, 33, 34A–B, 35A–C, 36, 37A–D, 38, 39, and 40.
Figure 29A:
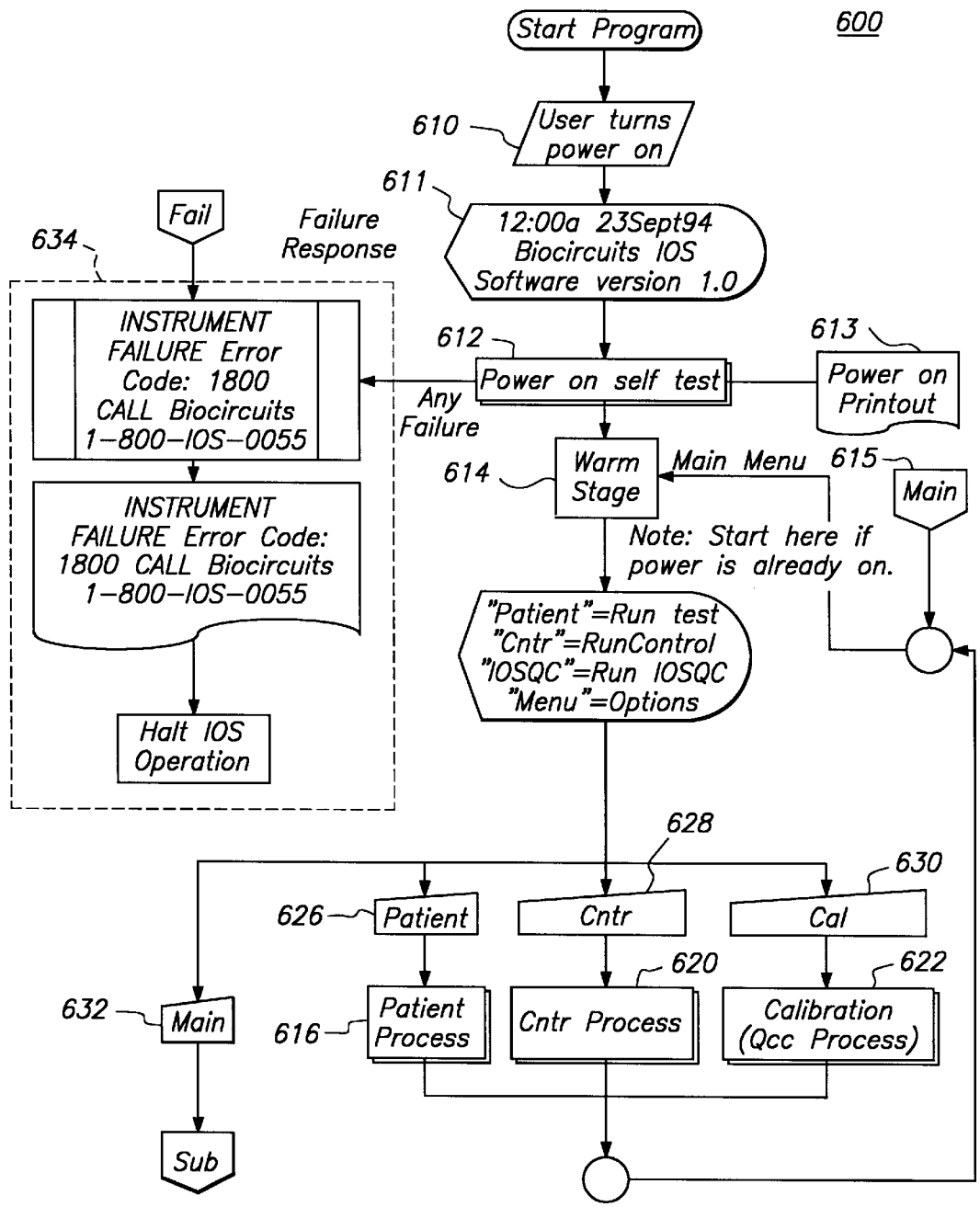
FIGS. 29A–C are diagrammatic flow-charts depicting the main operational sequence corresponding to system initialization and to the generation of a main menu for display to a user of the instrument.
Figure 29B:
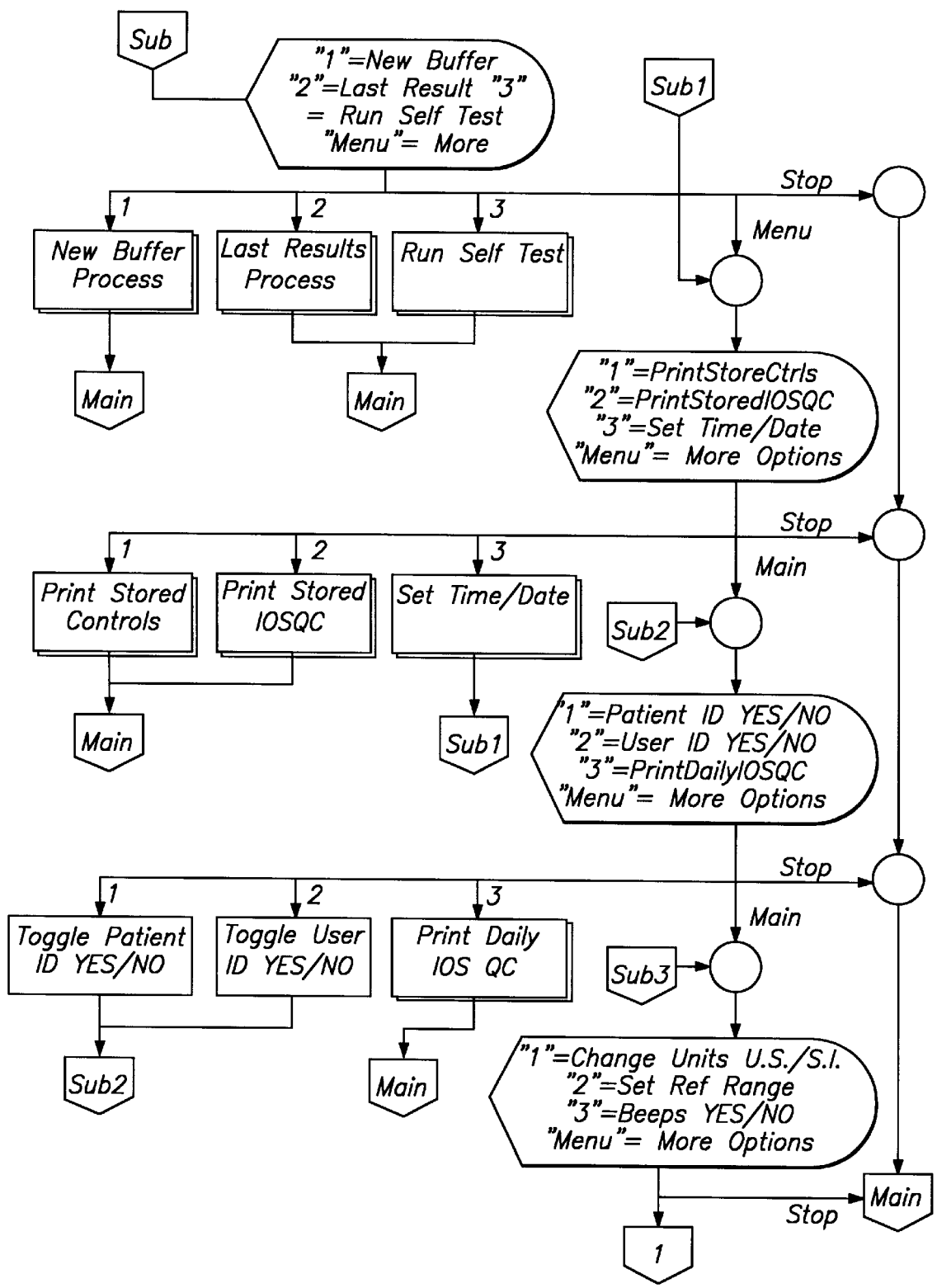
Figure 29C:
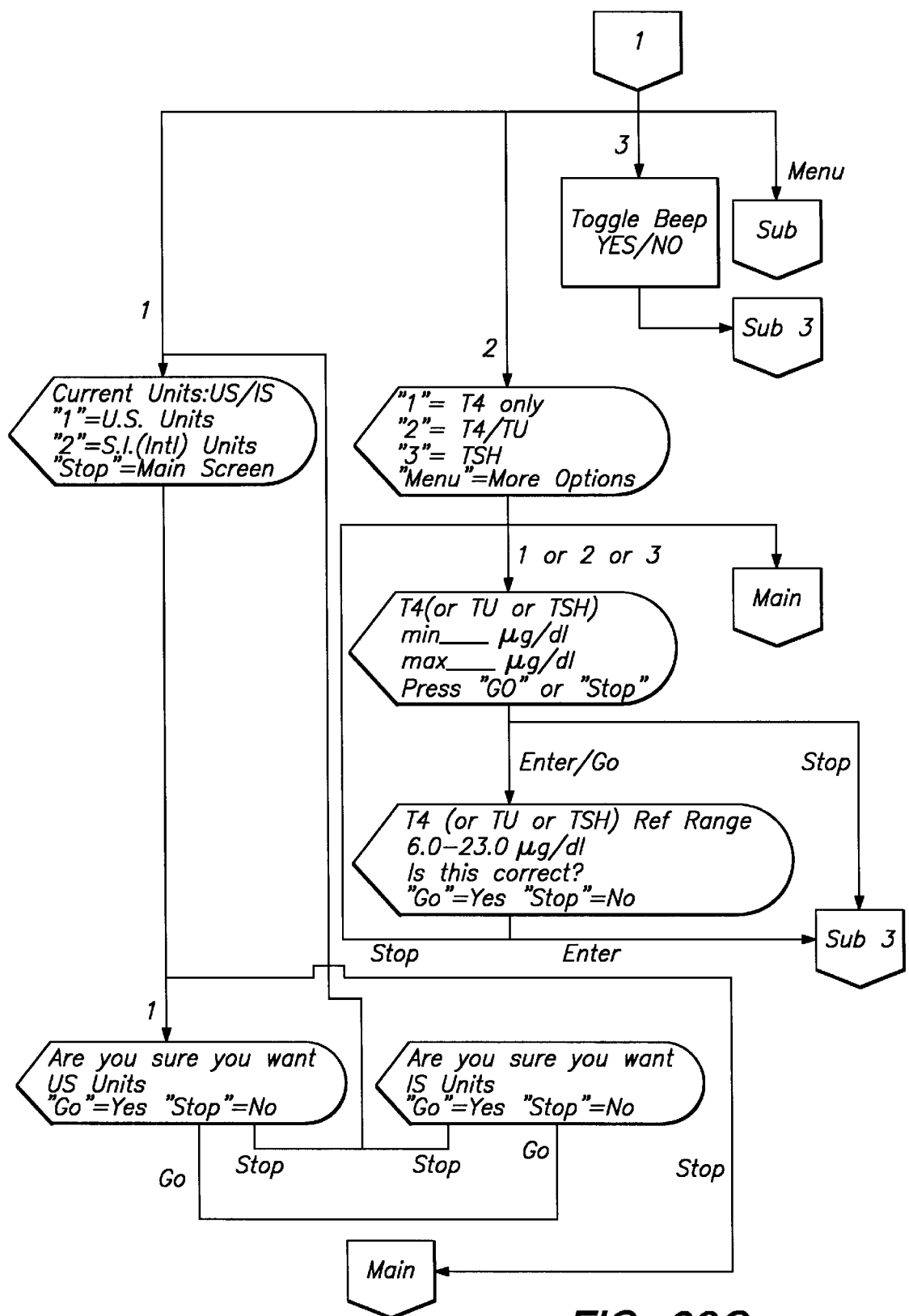
Figure 30:
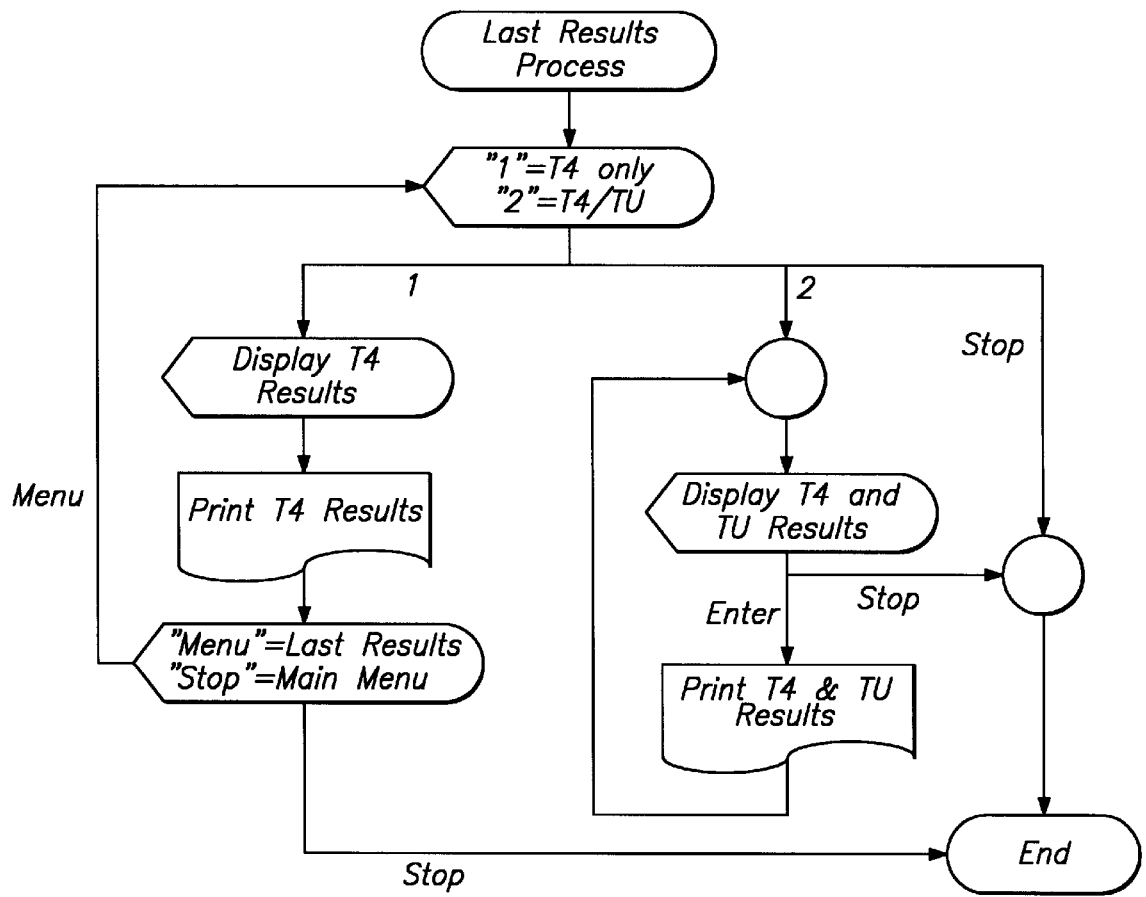
FIG. 30 is a diagrammatic flow-chart depicting the operational sequence in an alternative embodiment of the inventive methodology corresponding to the Last Results Process.
Figure 31A:
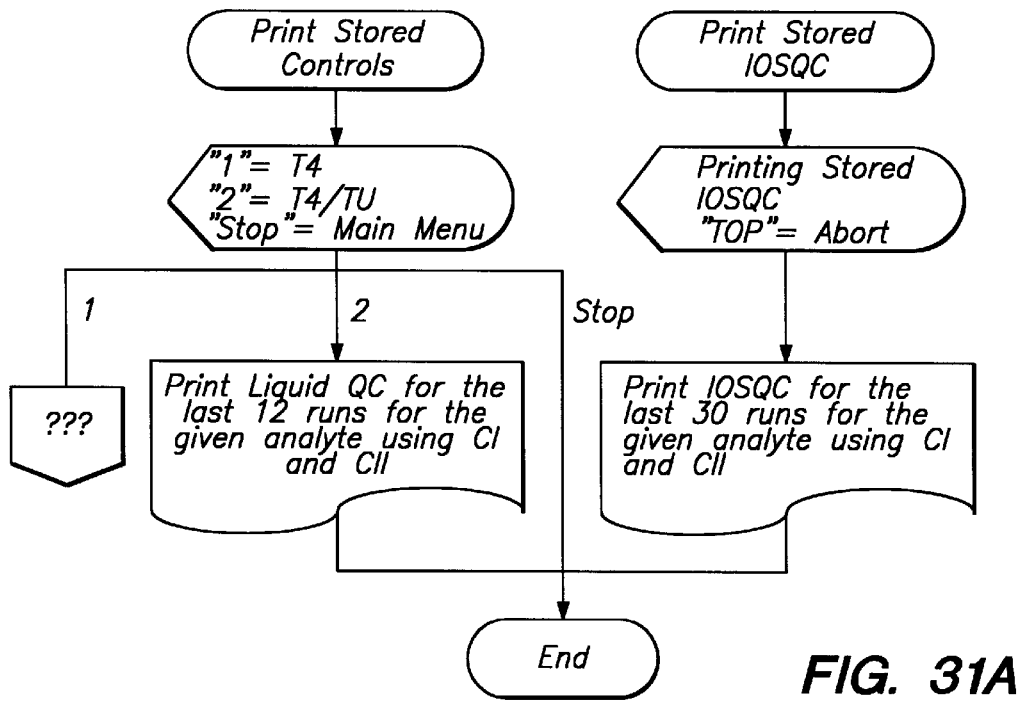
FIGS. 31A–C are diagrammatic flow-charts depicting the operational sequence in an alternative embodiment of the inventive methodology corresponding to the Print Stored Controls, Printing Stored IOSQC, Qcc Process, and Printing Daily IOSQC Process.
Figures 31B, 31C:
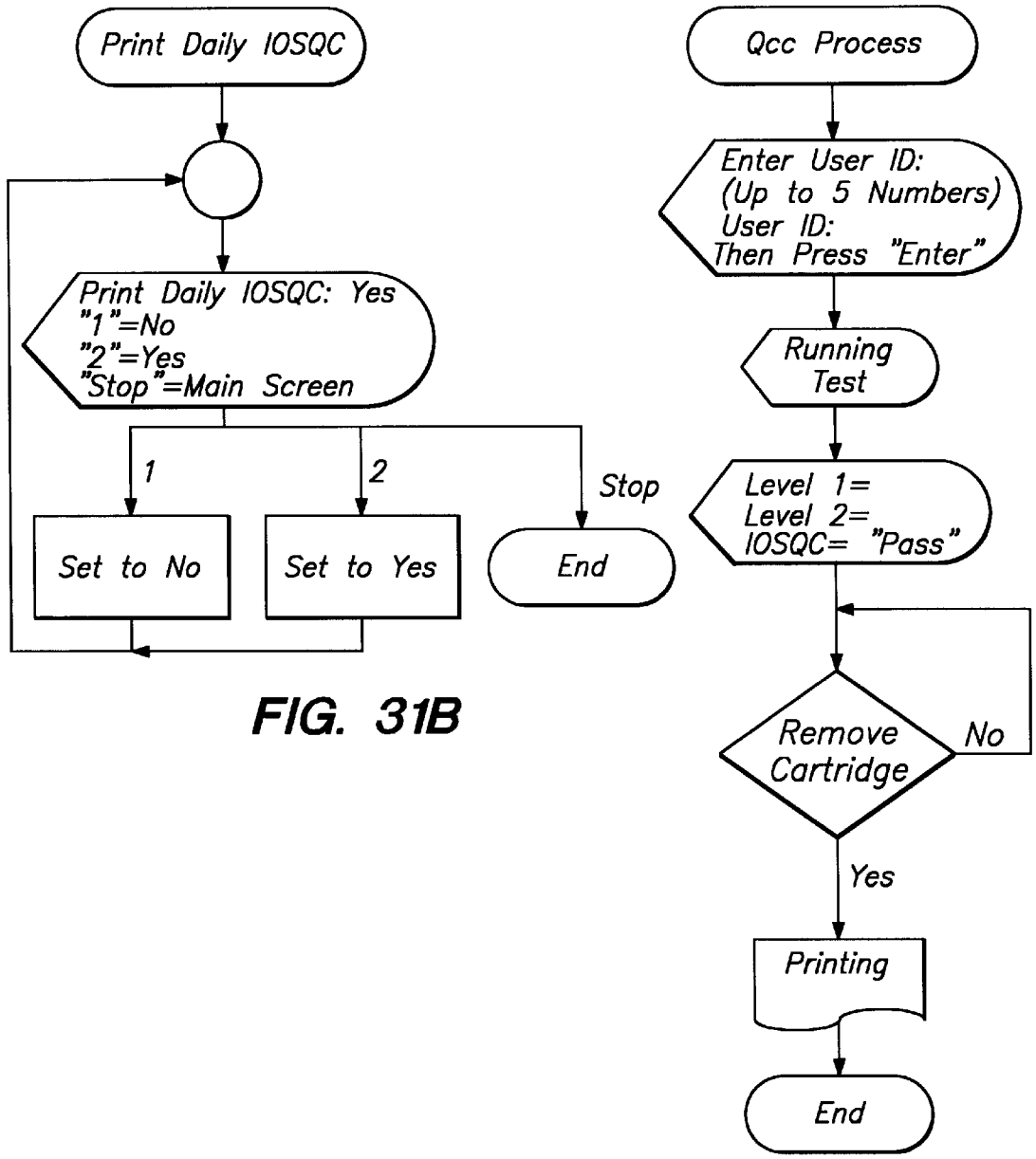
Figure 32:
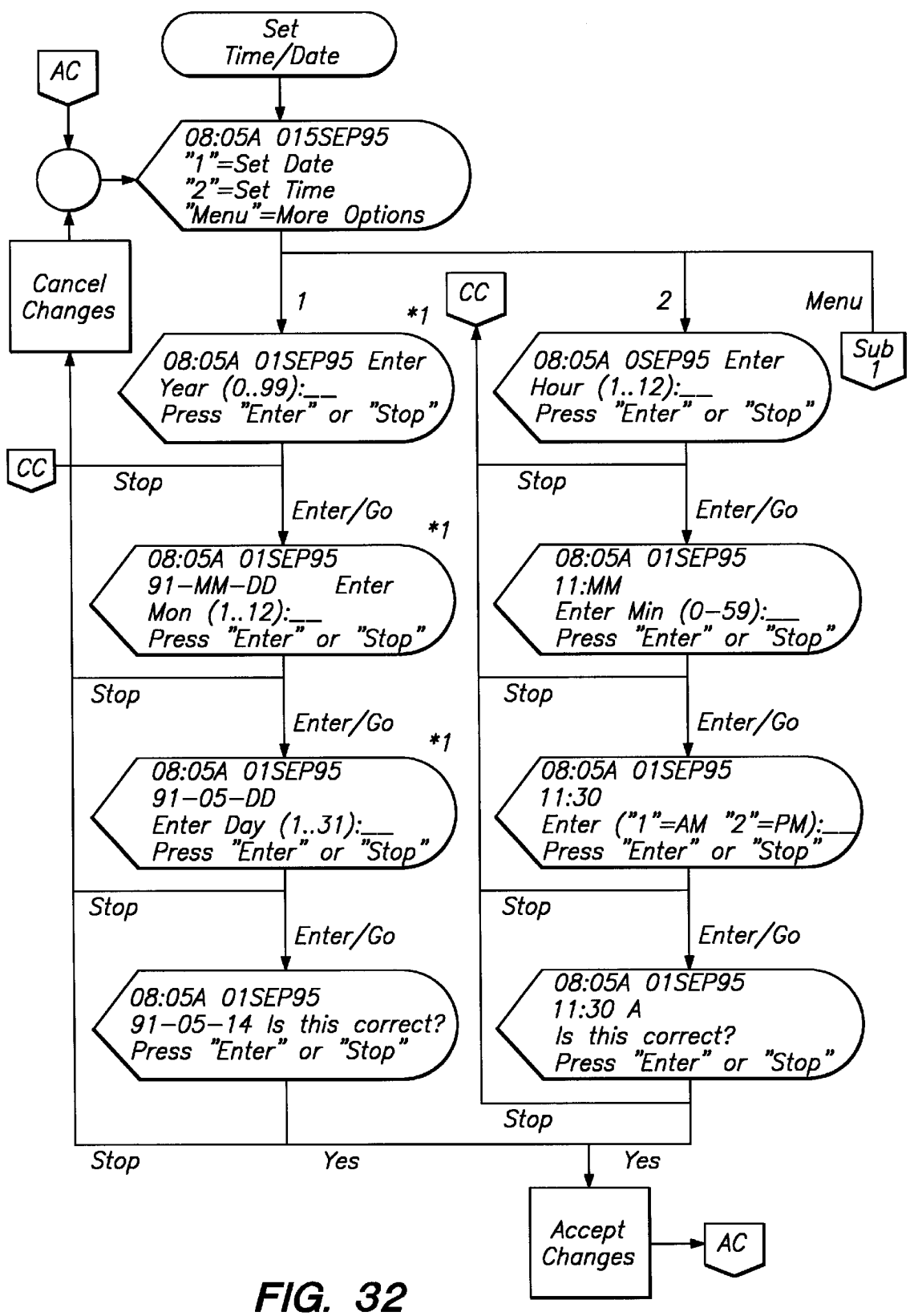
FIG. 32 is a diagrammatic flow-chart depicting the operational sequence in an alternative embodiment of the inventive methodology corresponding to the Set Time/Date Process.
Figure 33:
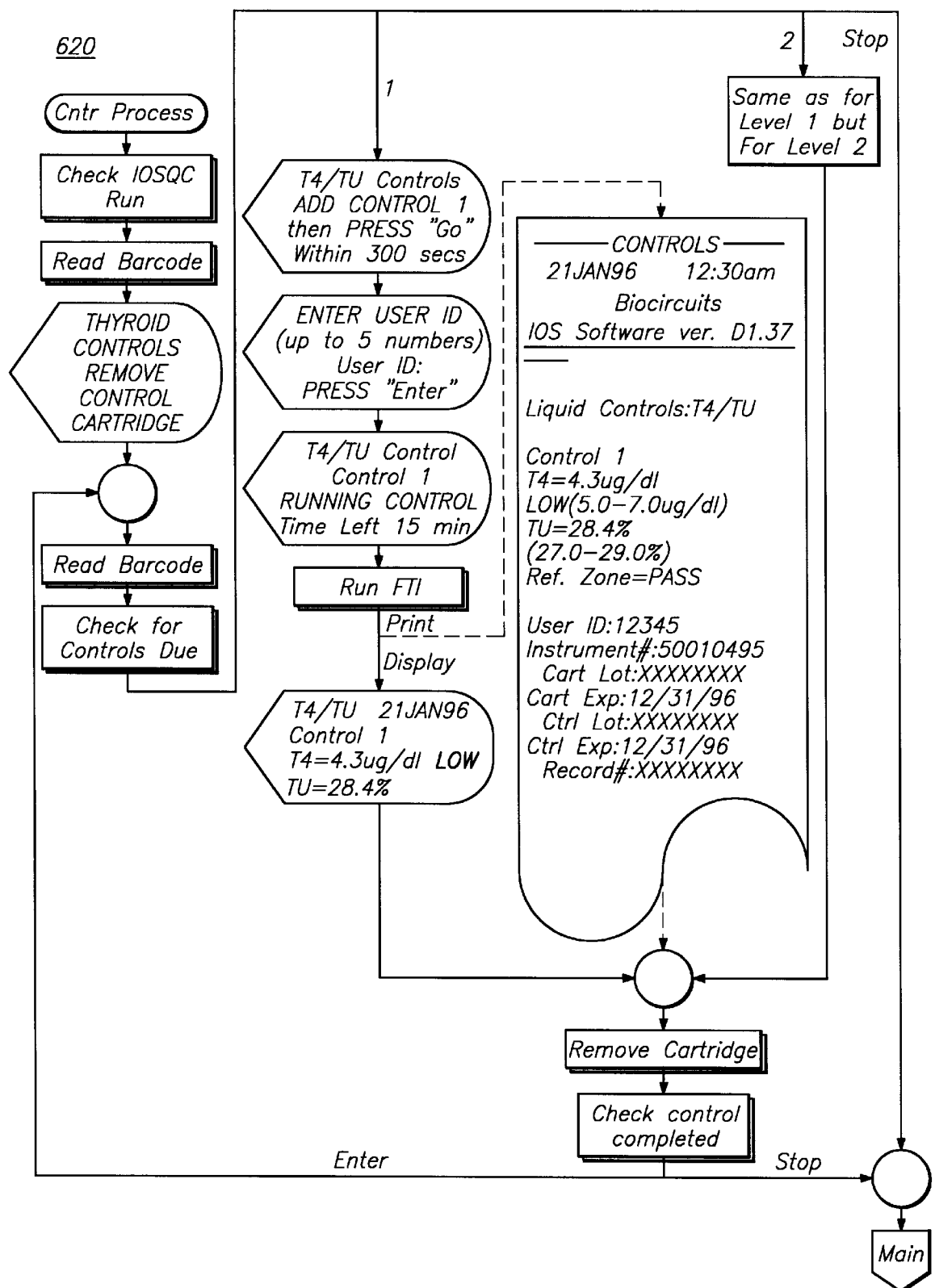
FIG. 33 is a diagrammatic flow-chart depicting the operational sequence in an alternative embodiment of the inventive methodology corresponding to the Control (Cntr) Process.
Figure 34A:
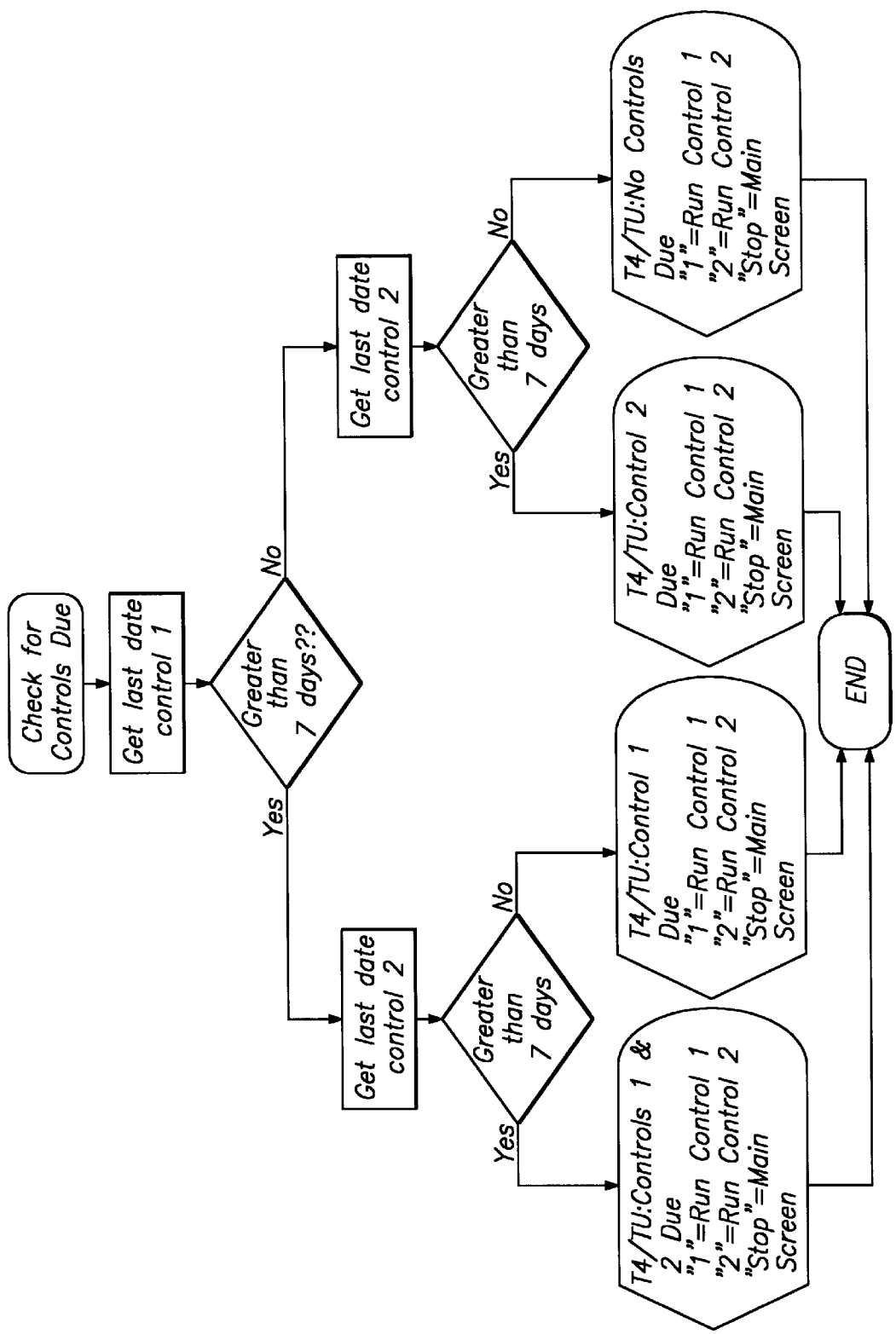
FIGS. 34A–B are diagrammatic flow-chart depicting the operational sequence in an alternative embodiment of the inventive methodology corresponding to the Check for Controls Due Process and Check Control Completed Process.
Figure 34B:
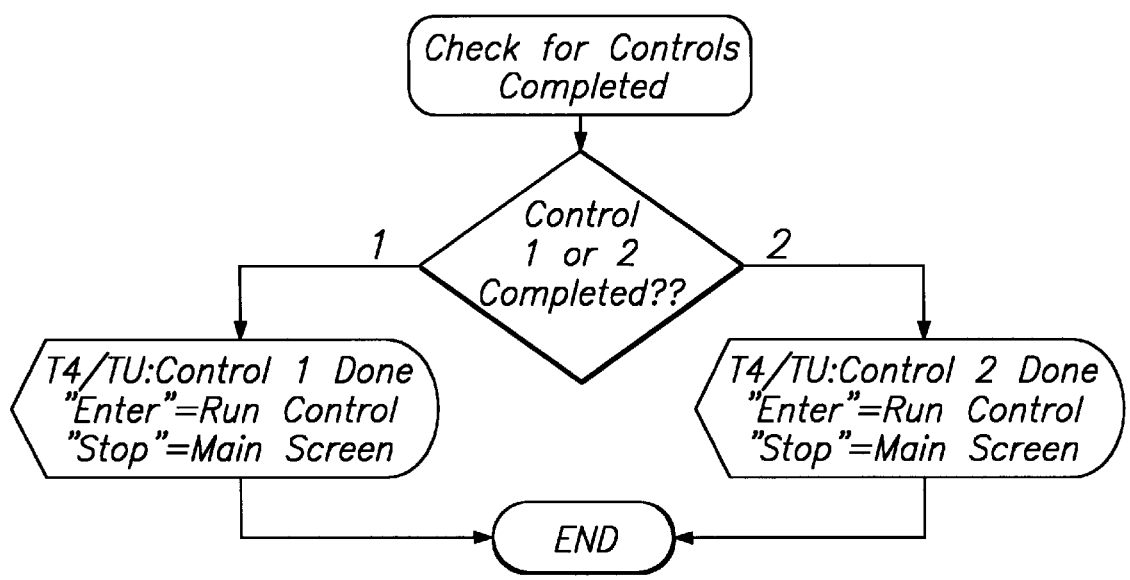
Figures 35A, 35B:
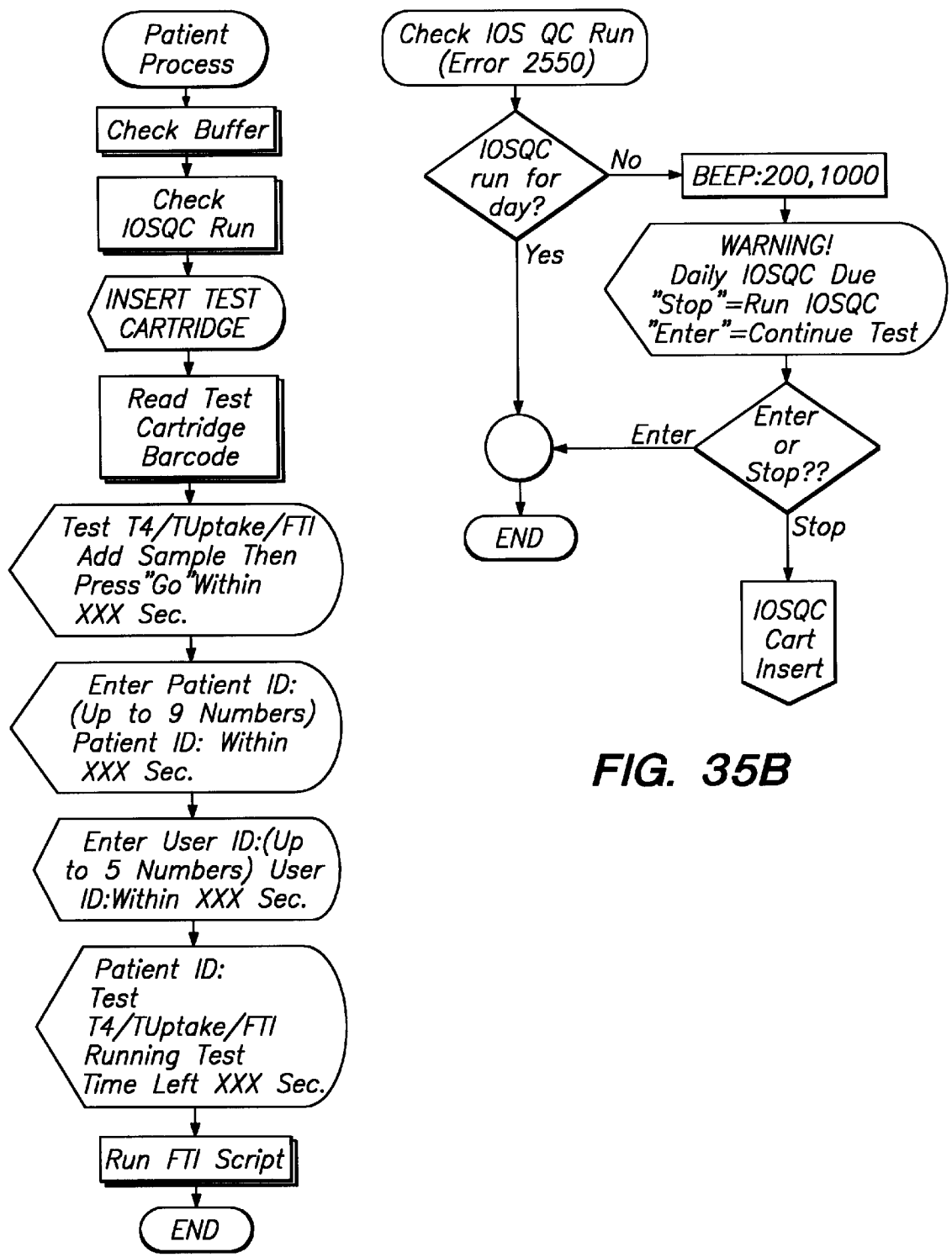
FIGS. 35a–35d are a diagrammatic flow-chart depicting the operational sequence in an alternative embodiment of the inventive methodology corresponding to the Patient Process, the Check IOS Qc Run Process, the Check Buffer Fluid Process, and the TIF Script Process.
Figure 35C:
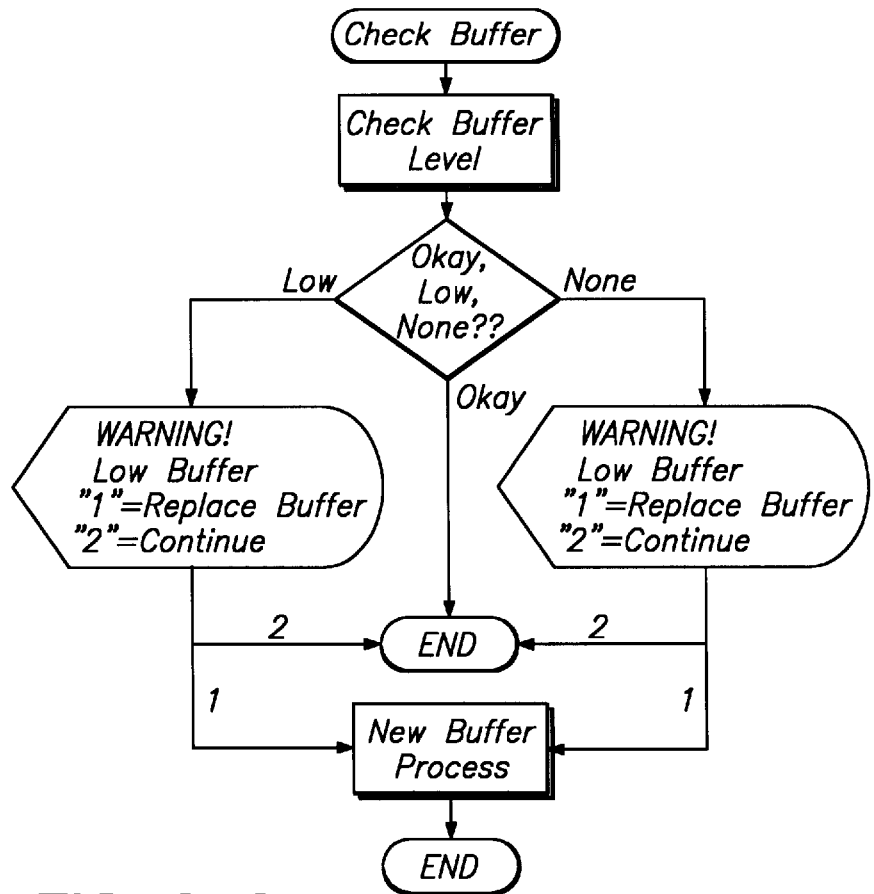
Figure 35D:
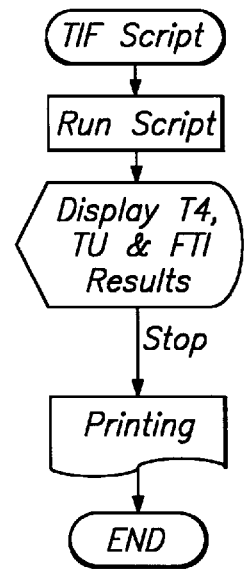
Figure 36:
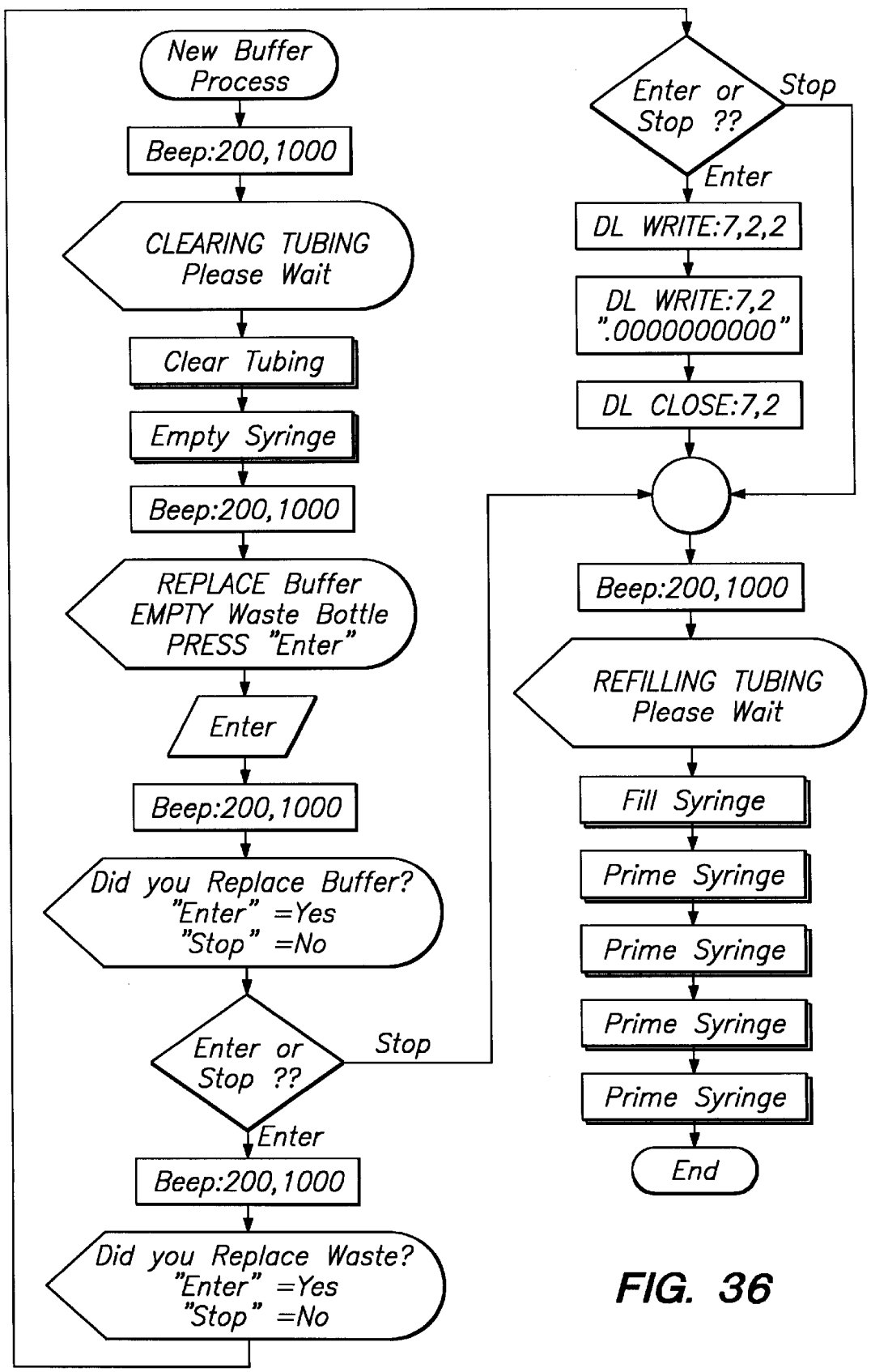
FIG. 36 is a diagrammatic flow-chart depicting the operational sequence in an alternative embodiment of the inventive methodology corresponding to the New Buffer Process.
Figure 37D:
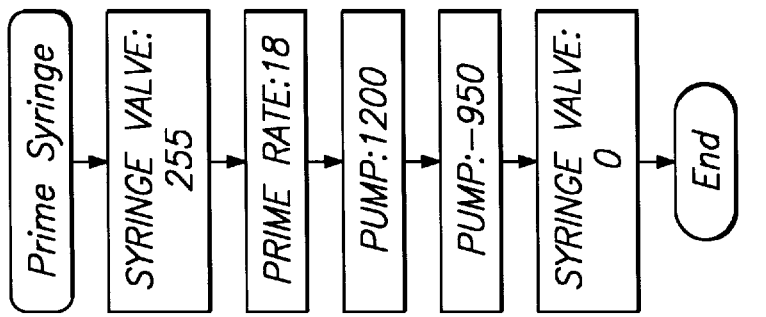
FIGS. 37A–D are diagrammatic flow-charts depicting the operational sequence in an alternative embodiment of the inventive methodology corresponding to the Clear Tubing Process, the Empty Syringe Process, the Fill Syringe Process, and the Prime Syringe Process.
Figure 37C:
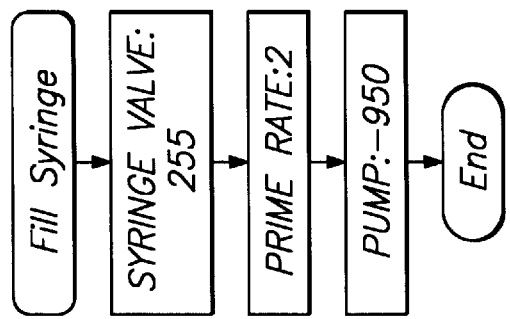
Figure 37B:
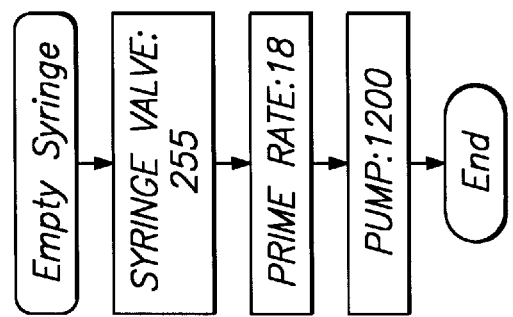
Figure 37A:
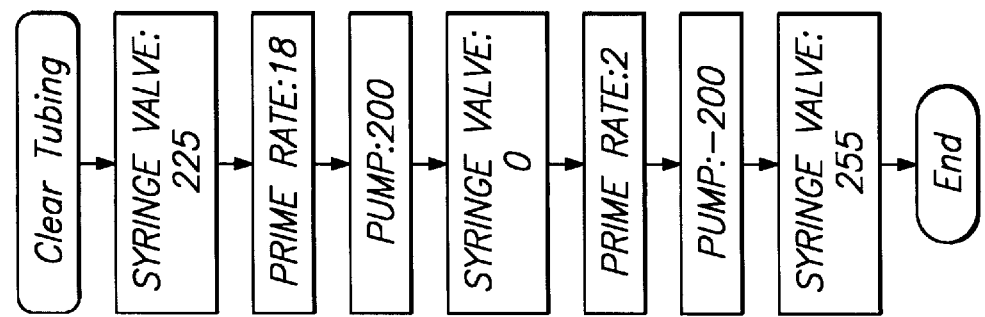
Figure 38B:
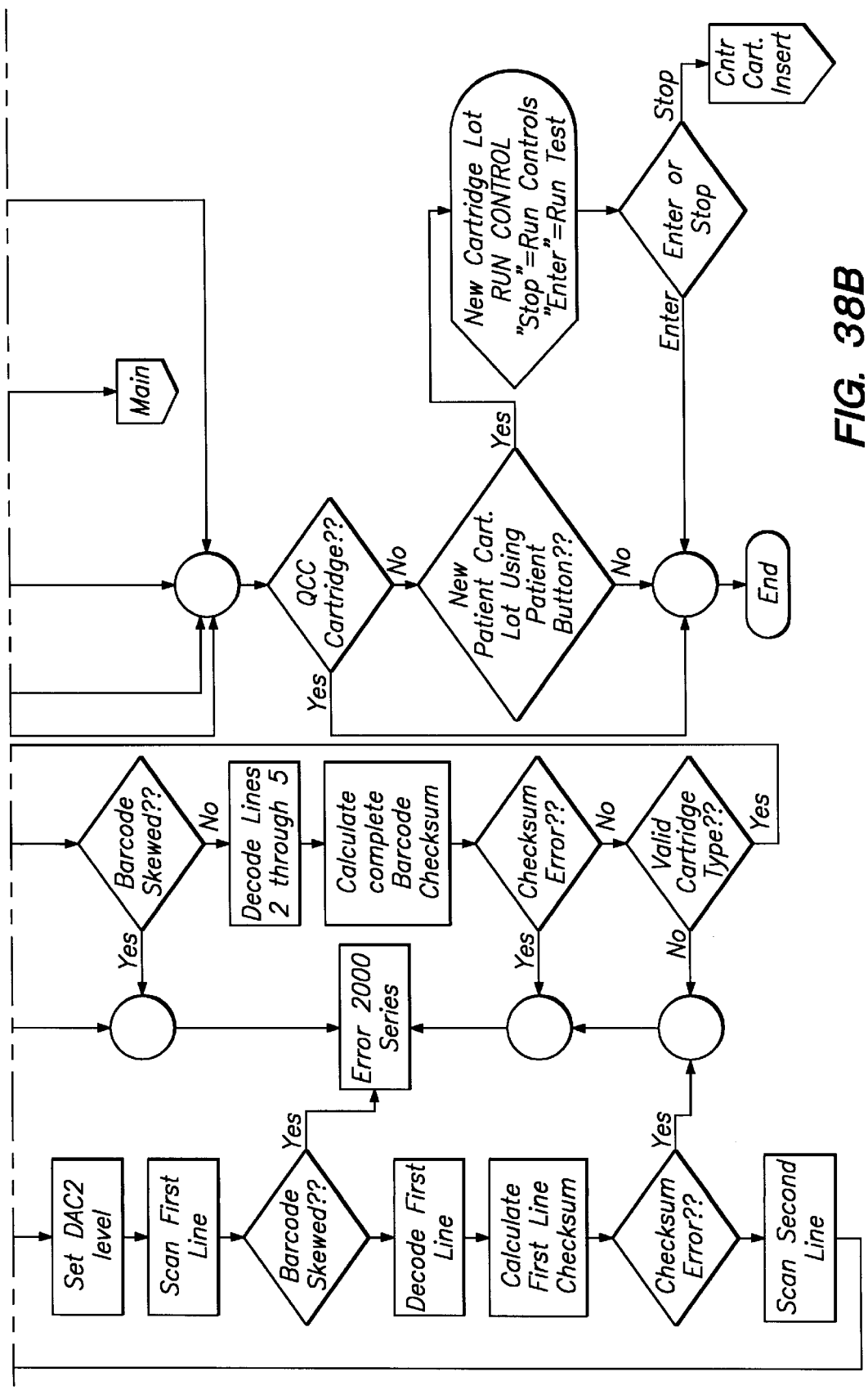
FIG. 38 is a diagrammatic flow-chart depicting the operational sequence in an alternative embodiment of the inventive methodology corresponding to the Read Barcode Process.
Figure 39:
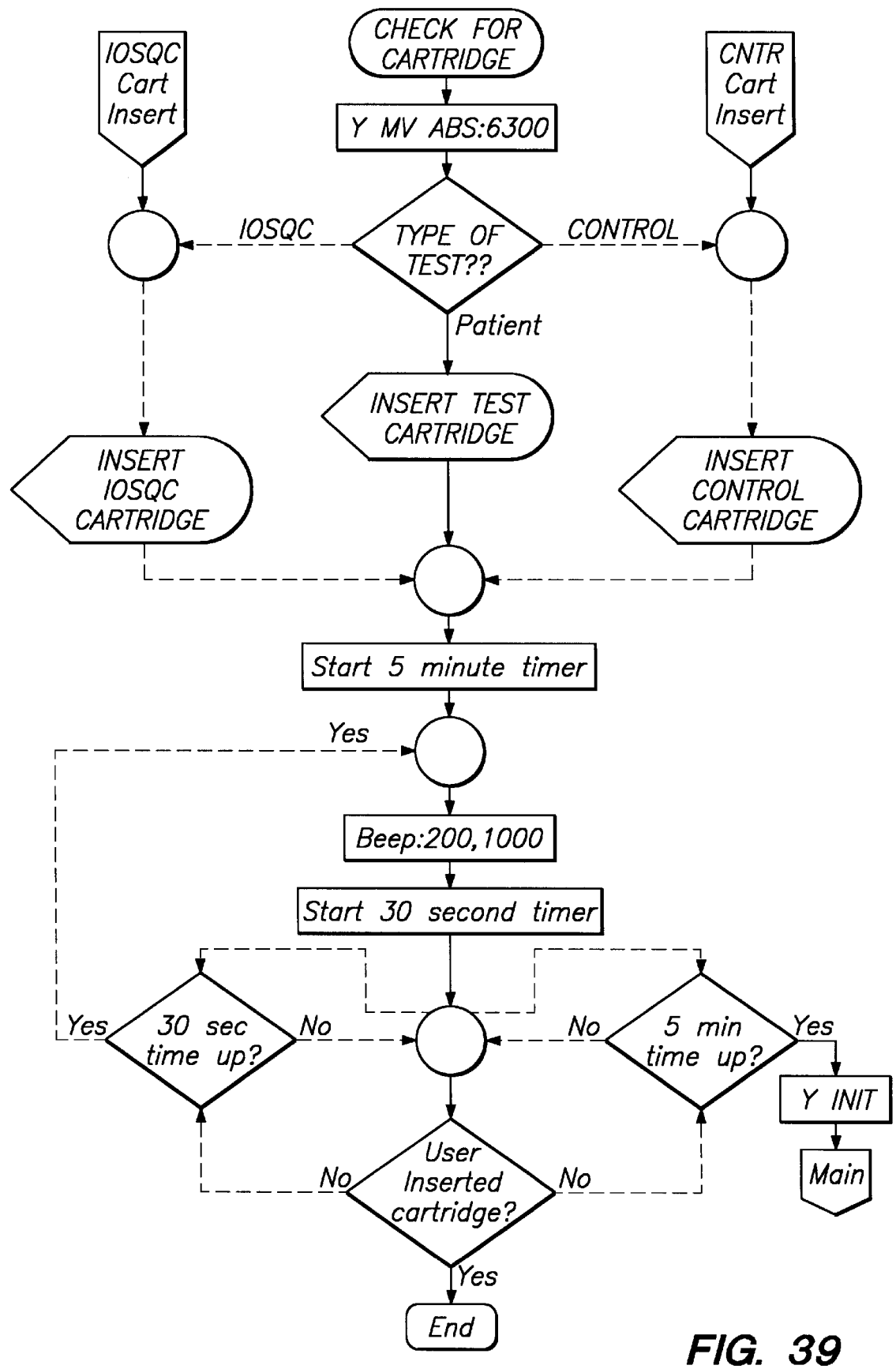
FIG. 39 is a diagrammatic flow-chart depicting the operational sequence in an alternative embodiment of the inventive methodology corresponding to the Check for Cartridge Process.
Figure 40:
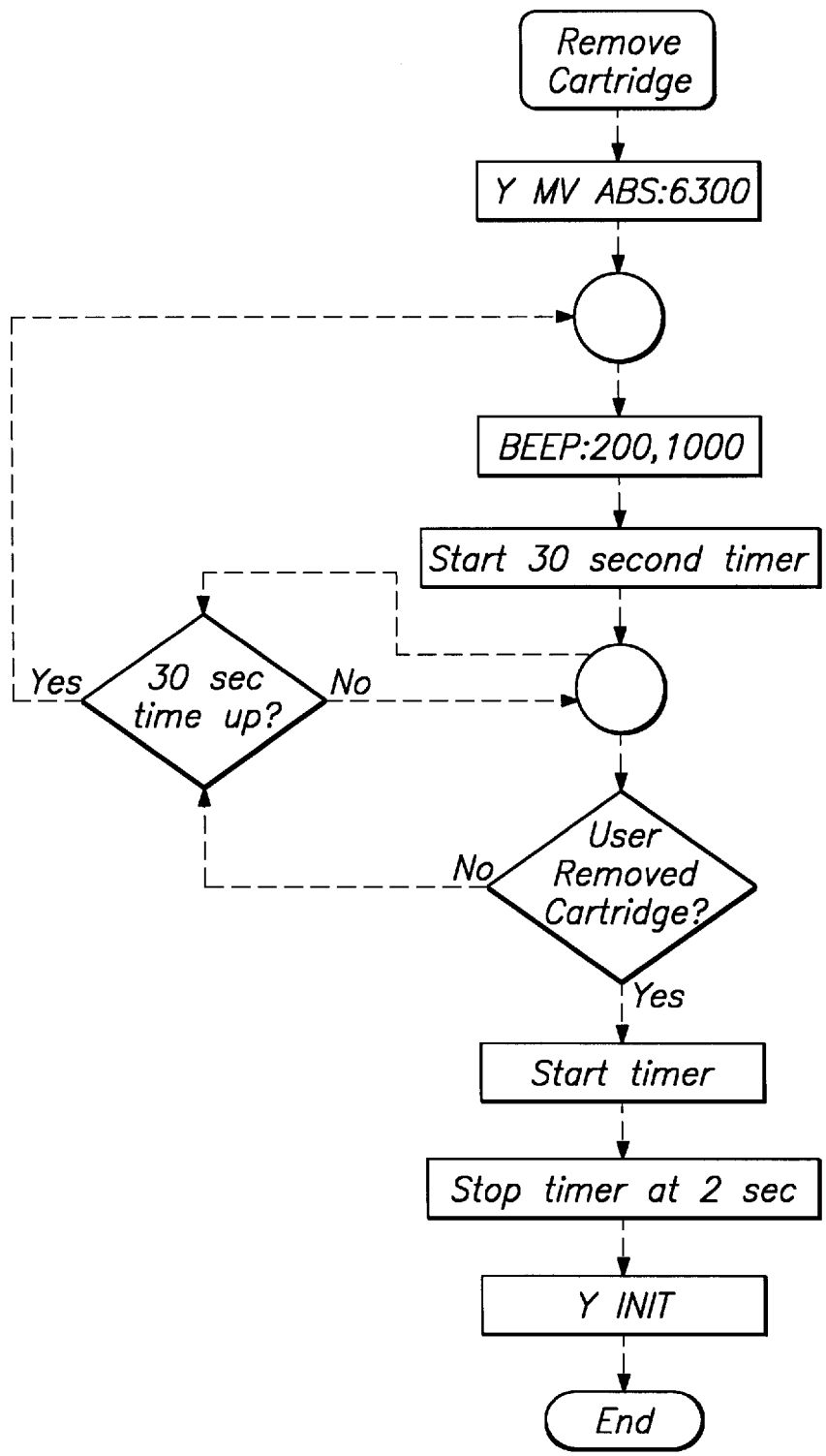
FIG. 40 is a diagrammatic flow-chart depicting the operational sequence in an alternative embodiment of the inventive methodology corresponding to the Remove Cartridge process.

Referring now to FIGS. 27A–C, there is shown a flow chart depicting the operational sequences included within the Control procedure (step 620). The Control procedure is initiated by prompting the user (step 690) to insert a sample cartridge 24 into port 20. Upon cartridge insertion (step 691) the bar code identifying label affixed to the cartridge 24 is scanned (step 622) and parameters defining control ranges associated with a control sample substance to be analyzed are stored at a predefined memory location (step 693). As is indicated by FIG. 28, the Control procedure is continued upon operator removal of the control cartridge and insertion of a first test cartridge (steps 695–698).

The coefficients associated with a first control sample are then read from the first test cartridge during a subsequent bar code scan (step 699), and are stored within system memory (steps 694A, 694B). The first test cartridge is warmed by heater plate 54 (steps 701–703). After reaching a predetermined temperature the cartridge is presented (step 704) to the operator, and a prompt is issued via LCD 14 instructing the operator to add the first control sample, i.e., Control A, to the first test cartridge (step 705). If this is not done within a predefined timeout period the operator is prompted to remove the cartridge from the instrument (steps 706, 707) and the operator is again prompted to insert the first test cartridge (step 697). Assuming that Control A is added to the cartridge in a timely manner, execution of a Control Assay is commenced and a "Test Running" message is provided to the operator (steps 710–712). The specific sequence of operations executed during the Control Assay will be dependent upon the type of the associated diagnostic test, but will generally involve the performance of operations of the type described above in connection with the Patient Assay script.

As is indicated in FIGS. 27A–C the curve coefficients associated with the Control A sample are utilized during performance of the Control Assay (step 673) in order to calculate an amount provided to numerical analysis data store (step 714). Testing of Control A is concluded upon removal of the first test cartridge from the instrument 10 (steps 715, 716), at which time the operator is prompted to insert a second test cartridge (step 697').

Referring to FIGS. 27A–C, a Control B sample inserted into the second test cartridge is analyzed (steps 698'–712') in the same manner as was described above with reference to testing of the sample Control A In addition, however, a set of Control Results are calculated (step 720) on the basis of:

(i) the Control Ranges obtained from the control cartridge (step 692), and (ii) a Dosage numerically determined (step 714') in accordance with the Dose measured during testing (step 712') of Control B.

As is shown in FIGS. 27A–C, the Control Results are provided to a Control History File (step 722) and are displayed to the operator together with a prompt to remove the second test cartridge (step 723). The control procedure is terminated upon removal of the second test cartridge (step 724) from the instrument 10, at which time the Main Menu is again displayed (step 725).

The operational sequences included within the Calibration procedure (step 622) are substantially identical to those described with reference to the Control procedure (FIGS. 27A–C), with the exception that calibration cartridges rather than control cartridges provide the subjects for analysis. In this regard the bar code identifier for each calibration cartridge will include information relating to Calibration Values associated with a particular calibration substance. After each calibration substance has been tested, the Calibration Values are used in conjunction with a numerically determined calibration dosage to determine a set of Calibration Results. Referring again to FIG. 26, (selection 632) of the Menu procedure (step 624) results in a menu being displayed on the LCD.

FIGS. 28, 29A–C, 30, 31A–C, 32, 33, 34A–B, 35A–C, 36, 37A–D, 38, 39, and 40 provide descriptions of alternative embodiments of the inventive procedures for use with an instrument 10 according to the present invention. These procedures are rather self-explanatory to those having ordinary skill in the art in light of the other descriptions provided herein. The IOS instrument 10 is adaptable to a variety of assay determinations and tests, significant among them is a FTI test approved by the United States Food and Drug Administration (FDA); however, the instrument is not limited either to particular tests, assays, or procedures described herein, not to particular regression or coorelation equations or techniques. The programmability of the instrument provides means for adapting to a great variety of procedures.

While the present inventive instrument, system, apparatus, and method has been described with reference to a few specific embodiments, the description is illustrative of the invention and is not to be construed as limiting the invention. Various modifications may occur to those skilled in the art without departing from the true spirit and scope of the invention as defined by the appended claims. All references cited herein are hereby incorporated by reference.

What is claimed is:

1. An electro-optical instrument for measuring a quantitative physical parameter of a sample in a diagnostic cartridge, comprising:

a light source configured to project an excitation light upon the sample and upon a reference detector, the excitation light having an excitation spectrum and being capable of stimulating fluorescence of a component within the sample, the fluorescence having an emission spectrum noncoincident with the excitation spectrum;

a first optical path alone which a first portion of the excitation light can be directed toward the reference detector;

a second optical path along which a second portion of the excitation light can be directed toward the sample and along which the fluorescence can be directed toward an emission detector positioned to receive the fluorescence;

a fluid supply adapted to dispense a predetermined amount of a fluid into the cartridge;

a cartridge carriage adapted to receive the cartridge and to position it in optical alignment with the excitation light and in fluid receiving alignment with the fluid supply;

a synchronous detector capable of generating a first detection signal in response to the fluorescence directed toward the emission detector and a second detection signal in response to the first portion of the excitation light directed toward the reference detector; and a differential converter configured to receive the first and second detection signals and produce an output signal representative of the quantitative physical parameter.

2. The instrument of claim 1, wherein the sample is tagged with a fluorophore, and wherein the second optical path includes an optical filter positioned in optical alignment between the fluorescence and the emission detector, the optical filter having a passband selected in accordance with the absorption spectrum of the fluorophore.

3. The instrument of claim 1, further comprising a heater, in contact with the cartridge, capable of selectively controlling the temperature of the sample.

4. The instrument of claim 1, further including at least one stage reference patch on the carriage used to calibrate the instrument.

5. The instrument of claim 1, further comprising an air puffer device capable of generating and applying a puff of air into the cartridge.

6. The instrument of claim 1, wherein the fluid supply includes a mixer capable of mixing the fluid with predried reagents in the cartridge.

7. The instrument of claim 1, wherein the reference detector is configured to produce an analog reference signal indicative of the intensity of the excitation light, and wherein the emission detector is configured to produce an emission signal indicative of the intensity of the fluorescence.

8. The instrument of claim 7 wherein the synchronous detector further includes:

a first integrator, switchably connected to the emission detector and capable of generating the first detection signal by integrating the emission signal, and a second integrator, switchably connected to the reference detector and capable of generating the second detection signal by integrating the analog reference signal.

9. The instrument of claim 8, further including an excitation source, operatively coupled to the first and second integrators and to the light source, and capable of switching the light source ON and OFF at a predetermined chopping frequency to generate a plurality of light excitation pulses.

10. The instrument of claim 8, wherein the first integrator includes a first switch, also connected to the emission detector, and a first control capable of opening the first switch during each ON interval and closing the first switch during each OFF interval.

11. The instrument of claim 10, wherein the second integrator includes a second switch, also connected to the reference detector, and a second control capable of closing the second switch during each ON intervals and opening the second switch during each OFF interval.

12. The instrument of claim 11, wherein the differential converter includes an analog to digital converter having a pair of inputs connected to the first and second integrators, the analog to digital converter capable of generating a digital output signal representative of the magnitude difference between the first and second detection signals.

13. The instrument of claim 7, further comprising a dichroic beamsplitter positioned in the second optical path and configured to substantially reflect the second portion of the excitation light toward the sample and to substantially pass the fluorescence toward the emission detector.

14. The instrument of claim 13, wherein the light source includes:

a broad-band light source, and an optical excitation filter positioned to receive light from the broad-band light source and having a passband that substantially corresponds with the absorption range of a fluorescent dye used to tag a fluorophore in the sample.

15. The instrument of claim 14, wherein the second optical path further includes a lens positioned to focus the substantially reflected portion of the second portion of the excitation light upon the sample and collimate the fluorescence.

16. The instrument of claim 14 wherein the fluid supply includes a syringe to controllably dispense the fluid into the cartridge.

17. The instrument of claim 1, further including a bar code reader positioned to scan a coded identifying label of the cartridge, the coded identifying label having a plurality of light regions interspersed between a plurality of dark regions.

18. The instrument of claim 17, wherein the bar code reader includes:

a beam projector configured to project a scanning beam across the coded identifying label;

an optical sensor positioned to detect and determine the intensity of light from the scanning beam reflected by the identifying label; and a comparator capable of identifying the light and dark regions of the coded label by comparing the determined intensity of the light reflected from the identifying label with a threshold intensity.

19. The instrument of claim 18, wherein the bar code reader further includes a calibrator capable of establishing the threshold intensity based upon a peak intensity of the light reflected from the identifying label and a minimum intensity of light reflected by a maximum density region of the label.

20. The instrument of claim 19, further comprising a user interface from which an analysis program can be selected, the analysis program capable of determining the concentration of the sample based on the output signal; and a microprocessor configured to execute the program.

21. The instrument of claim 20, wherein the instrument is configured to self-calibrate to adjust the correlation between the output signal and the quantitative physical parameter in response to changes in the first and second optical paths and the synchronous detector.

22. An electro-optical instrument for measuring a quantitative physical parameter of a sample in a diagnostic cartridge, comprising:

a light source means for projecting an excitation light upon the sample and a reference detector, the excitation light having a first spectral bandwidth and being capable of stimulating fluorescence of a component within the sample, the fluorescence having a second spectral bandwidth, the first and second bandwidths having at least one non-overlapping spectral wavelength range;

first optical means for transmitting portions of the excitation light in order to produce a reference excitation light toward a reference detector;

second optical means for directing a portion of the excitation light toward the sample along a first path and for directing a portion of the fluorescence received from the sample along a different path;

a syringe means for dispensing a predetermined amount of fluid into the diagnostic cartridge;

a cartridge carriage means for accepting the diagnostic cartridge containing the sample and for positioning the cartridge in optical alignment with the excitation light and fluid receiving alignment with the syringe means;

a mixing means for mixing the fluid with predried reagents in the diagnostic cartridge;

synchronous detector means for generating a first detection signal in response to the fluorescence and a second detection signal in response to the reference excitation light; and differential conversion means for producing an output signal representative of the quantitative physical parameter based on the first and second detection signals.

* * * * *